(12) United States Patent
Bell et al.

(10) Patent No.: US 8,071,771 B2
(45) Date of Patent: *Dec. 6, 2011

(54) BICYCLIC SPIROHYDANTOIN CGRP RECEPTOR ANTAGONISTS

(75) Inventors: Ian M. Bell, Harleysville, PA (US);
Harold G. Selnick, Ambler, PA (US);
Craig A. Stump, Pottstown, PA (US);
Cory R. Theberge, King of Prussia, PA (US); C. Blair Zartman, Hatfield, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 710 days.

This patent is subject to a terminal disclaimer.

(21) Appl. No.: 12/085,005

(22) PCT Filed: Nov. 14, 2006

(86) PCT No.: PCT/US2006/044194
§ 371 (c)(1),
(2), (4) Date: May 14, 2008

(87) PCT Pub. No.: WO2007/061695
PCT Pub. Date: May 31, 2007

(65) Prior Publication Data
US 2009/0176757 A1    Jul. 9, 2009

Related U.S. Application Data

(60) Provisional application No. 60/738,333, filed on Nov. 18, 2005.

(51) Int. Cl.
*C07D 211/00* (2006.01)
*C07D 401/00* (2006.01)
(52) U.S. Cl. .......................................... 546/15; 546/18
(58) Field of Classification Search ................... 546/15, 546/18
See application file for complete search history.

(56) References Cited

U.S. PATENT DOCUMENTS

| | | |
|---|---|---|
| 5,436,261 A | 7/1995 | Cordi et al. |
| 6,057,335 A | 5/2000 | Fukami et al. |
| 6,638,942 B1 | 10/2003 | Gao et al. |
| 2004/0186155 A1 | 9/2004 | Dayno et al. |

FOREIGN PATENT DOCUMENTS

| | | |
|---|---|---|
| WO | WO 2004/082605 A2 | 9/2004 |
| WO | WO 2007/061676 A1 | 5/2007 |
| WO | WO 2007/061677 A2 | 5/2007 |
| WO | WO 2007/061692 A2 | 5/2007 |
| WO | WO 2007/061694 A2 | 5/2007 |
| WO | WO 2007/061696 A2 | 5/2007 |

OTHER PUBLICATIONS

Sarges et al., CA 108:37727, 1988.*
Khan, et al., "A Novel and Expeditious Approach to Unusual Spirolactam Building Blocks," Journal of Organic Chemistry, vol. 23, 2003, pp. 4556-4559.
International Preliminary Report on Patentability for PCT/US2006/044194.

* cited by examiner

*Primary Examiner* — Janet L. Andres
*Assistant Examiner* — Raymond Covington
(74) *Attorney, Agent, or Firm* — Gerard M. Devlin; Raynard Yuro

(57) ABSTRACT

Compounds of formula I:

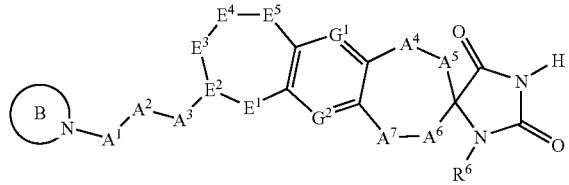

(wherein variables $A^1$, $A^2$, $A^3$, $A^4$, $A^5$, $A^6$, $A^7$, B, $E^1$, $E^2$, $E^3$, $E^4$, $E^5$, $G^1$, $G^2$ and $R^6$ are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

20 Claims, No Drawings

BICYCLIC SPIROHYDANTOIN CGRP RECEPTOR ANTAGONISTS

CROSS-REFERENCE TO RELATED APPLICATIONS

This application claims priority under 35 U.S.C. §119(e) of U.S. provisional application Ser. No. 60/738,333, filed Nov. 18, 2005.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, asthma (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

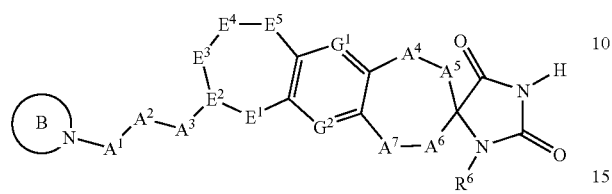

I wherein:

B is a bicycloheterocycle selected from the group consisting of:

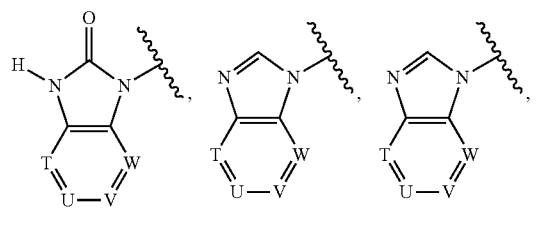

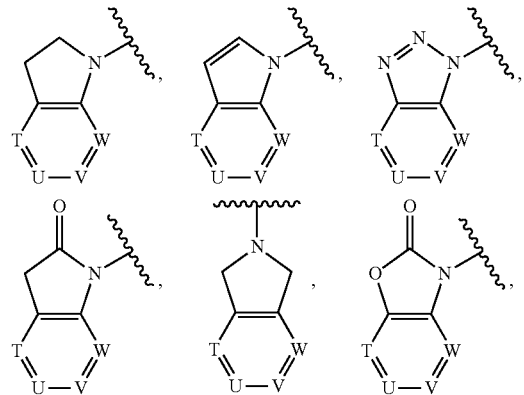

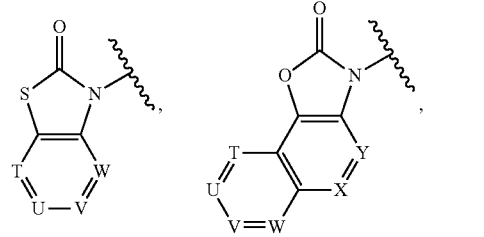

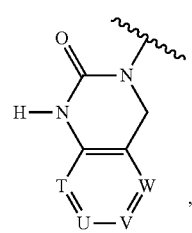

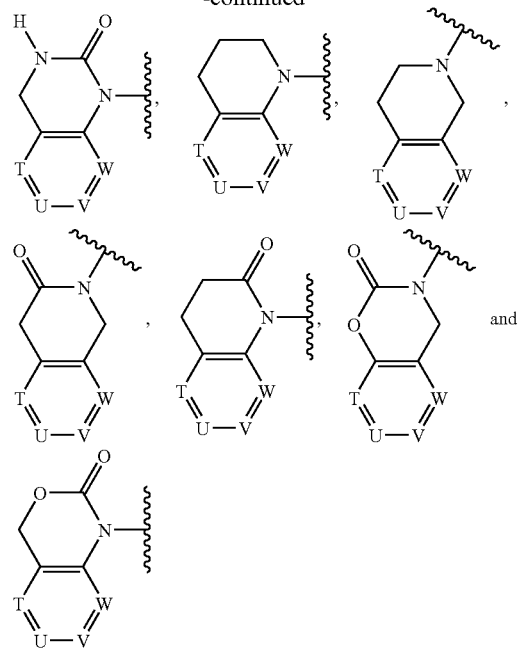

where T, U, V, W, X and Y are each independently a carbon atom or a nitrogen atom, wherein no more than two of T, U, V and W, or no more than three of T, U, V, W, X and Y, are a nitrogen atom, where B is unsubstituted or substituted with 1-5 substituents independently selected from $R^1$, $R^2$, $R^{3a}$ and $R^{3b}$, where $R^1$, $R^2$, $R^{3a}$ and $R^{3b}$ are independently selected from:

(1) —$C_{1-6}$alkyl, which is unsubstituted or substituted with 1-7 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: azetidinyl, imidazolyl, oxazolyl, pyridyl, pyrimidinyl, pyrazinyl, pyridazinyl, piperidinyl, azepanyl, azepinyl, piperazinyl, pyrazolyl, pyrrolidinyl, thiazolyl, thienyl, triazolyl, tetrazolyl, tetrahydrofuryl, and morpholinyl,
    which phenyl or heterocycle is unsubstituted or substituted with 1-5 substituents each independently selected from:
    (i) —$C_{1-6}$alkyl,
    (ii) —O—$C_{1-6}$alkyl,
    (iii) halo,
    (iv) hydroxy,
    (v) trifluoromethyl,
    (vi) —$OCF_3$,
    (vii) oxo,
    (viii) amino,
    (ix) phenyl, and
    (x) benzyl,
  (f) —$CO_2R^9$, wherein $R^9$ is independently selected from:
    (i) hydrogen,
    (ii) —$C_{1-6}$alkyl, which is unsubstituted or substituted with 1-6 substituents, substituents each independently selected from:
      (I) halo,
      (II) hydroxy, (III) —O—$C_{1-6}$alkyl, which is unsubstituted or substituted with 1-5 halo,
(IV) —$C_{3-6}$cycloalkyl,
(V) phenyl, which is unsubstituted or substituted with 1-5 substituents each independently selected from:
  (1) —$C_{1-4}$alkyl,
  (2) —O—$C_{1-6}$alkyl,
  (3) halo,
  (4) trifluoromethyl, and
  (5) —$OCF_3$,
(iii) —$C_{3-6}$cycloalkyl, which is unsubstituted or substituted with 1-5 halo, and
(iv) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:
  (I) halo,
  (II) —$C_{1-6}$alkyl, which is unsubstituted or substituted with 1-5 halo
  (III) —O—$C_{1-6}$alkyl, which is unsubstituted or substituted with 1-5 halo
  (IV) —$C_{3-6}$cycloalkyl,
  (V) oxo,
  (VI) —CN,
  (VII) hydroxy, and
  (VII) phenyl,
(g) —$NR^{10}R^{11}$, wherein $R^{10}$ and $R^{11}$ are each independently selected from:
  (i) hydrogen,
  (ii) —$C_{1-6}$alkyl, which is unsubstituted or substituted with 1-6 substituents each independently selected from:
    (I) —O—$C_{1-6}$alkyl,
    (II) halo,
    (III) hydroxy,
    (IV) —$OCF_3$,
    (V) —$C_{3-6}$cycloalkyl, and
    (VI) phenyl,
  (iii) —$C_{4-6}$cycloalkyl,
  (iv) phenyl, which is unsubstituted or substituted with 1-5 substituents each independently selected from:
    (I) —$C_{1-6}$alkyl,
    (II) —O—$C_{1-6}$alkyl,
    (III) halo,
    (IV) hydroxy,
    (V) trifluoromethyl,
    (VI) —$OCF_3$, and
    (VII) CN, and
  (v) benzyl, which is unsubstituted or substituted with 1-5 substituents each independently selected from:
    (I) —$C_{1-6}$alkyl,
    (II) —O—$C_{1-6}$alkyl,
    (III) halo, and
    (IV) trifluoromethyl,
  (vi) —$COR^9$, and
  (vii) —$SO_2R^{12}$,
(h) —$SO_2R^{12}$, wherein $R^{12}$ is selected from:
  (i) —$C_{1-6}$alkyl, which is unsubstituted or substituted with 1-6 fluoro,
  (ii) —$C_{3-6}$cycloalkyl,
  (iii) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl,
    which phenyl or heterocycle is unsubstituted or substituted with 1-5 substituents each independently selected from:
    (I) —$C_{1-6}$alkyl,
    (II) —O—$C_{1-6}$alkyl,
    (III) halo,
    (IV) hydroxy,
    (V) trifluoromethyl,
    (VI) —$OCF_3$, and
    (VII) CN, and
  (iv) benzyl, which is unsubstituted or substituted with 1-5 substituents each independently selected from:
    (I) —$C_{1-6}$alkyl,
    (II) —O—$C_{1-6}$alkyl,
    (III) halo, and
    (IV) trifluoromethyl,
(i) —$CONR^{10a}R^{11a}$, wherein $R^{10a}$ and $R^{11a}$ are each independently selected from:
  (i) hydrogen,
  (ii) —$C_{1-6}$alkyl, which is unsubstituted or substituted with 1-6 substituents each independently selected from:
    (I) —O—$C_{1-6}$alkyl,
    (II) halo,
    (III) hydroxy,
    (IV) —$OCF_3$,
    (V) —$C_{3-6}$cycloalkyl, and
    (VI) phenyl,
  (iii) —$C_{5-6}$cycloalkyl,
  (iv) phenyl, which is unsubstituted or substituted with 1-5 substituents each independently selected from:
    (I) —$C_{1-6}$alkyl,
    (II) —O—$C_{1-6}$alkyl,
    (III) halo,
    (IV) hydroxy,
    (V) trifluoromethyl,
    (VI) —$OCF_3$, and
    (VII) CN, and
  (v) benzyl, which is unsubstituted or substituted with 1-5 substituents each independently selected from:
    (I) —$C_{1-6}$alkyl,
    (II) —O—$C_{1-6}$alkyl,
    (III) halo, and
    (IV) trifluoromethyl,
  or where $R^{10a}$ and $R^{11a}$ join to form a ring selected from azetidinyl, pyrrolidinyl, piperidinyl, azepanyl, piperazinyl, and morpholinyl, which ring is unsubstituted or substituted with 1-5 substituents each independently selected from:
    (I) —$C_{1-6}$alkyl
    (II) —O—$C_{1-6}$alkyl
    (III) halo
    (IV) hydroxy
    (V) phenyl,
    (VI) benzyl,
    (VII) —$COR^9$, and
    (VIII) —$SO_2R^{12}$,
(j) trifluoromethyl,
(k) —$OCO_2R^9$, (l) —(NR$^{10a}$)CO$_2$R$^9$,
(m) —O(CO)NR$^{10a}$R$^{11a}$,
(n) —(NR$^9$)(CO)NR$^{10a}$R$^{11a}$,
(o) —SO$_2$NR$^{10a}$R$^{11a}$, and
(p) —O—C$_{3-6}$cycloalkyl,
(2) —C$_{3-6}$cycloalkyl, which is unsubstituted or substituted with 1-7 substituents each independently selected from:
(a) halo,
(b) hydroxy,
(c) —O—C$_{1-6}$alkyl,
(d) trifluoromethyl,
(e) phenyl, which is unsubstituted or substituted with 1-5 substituents each independently selected from:
(i) —C$_{1-6}$alkyl,
(ii) —O—C$_{1-6}$alkyl,
(iii) halo,
(iv) hydroxy, and
(v) trifluoromethyl,
(3) phenyl or heterocycle, wherein heterocycle is selected from: pyridyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, 1,3-dioxolanyl, oxadiazolyl, piperidinyl, tetrahydropyranyl, tetrahydrothienyl, tetrahydrothiopyranyl, and morpholinyl, which phenyl or heterocycle is unsubstituted or substituted with 1-5 substituents each independently selected from:
(a) —C$_{1-6}$alkyl, which is unsubstituted or substituted with 1-5 substituents each independently selected from:
(a) halo,
(b) hydroxy,
(c) —O—C$_{1-6}$alkyl,
(d) —C$_{3-6}$cycloalkyl,
(e) phenyl,
(f) —CO$_2$R$^9$, and
(g) —NR$^{10}$R$^{11}$,
(b) halo,
(c) hydroxy,
(d) —O—C$_{1-6}$alkyl, which is unsubstituted or substituted with 1-6 fluoro,
(e) —C$_{3-6}$cycloalkyl,
(f) phenyl or heterocycle, wherein heterocycle is selected from: pyrrolidinyl, piperidinyl, piperazinyl, pyridyl, pyrimidinyl, pyrazinyl, thienyl, and morpholinyl, which phenyl or heterocycle is unsubstituted or substituted with 1-5 substituents each independently selected from:
(i) —C$_{1-6}$alkyl,
(ii) —O—C$_{1-6}$alkyl,
(iii) halo,
(iv) hydroxy, and
(v) trifluoromethyl,
(g) —CO$_2$R$^9$,
(h) —(CO)R$^9$,
(i) —NR$^{10}$R$^{11}$,
(j) —CONR$^{10a}$R$^{11a}$,
(k) oxo
(l) —SR$^{12}$,
(m) —S(O)R$^{12}$,
(n) —SO$_2$R$^{12}$,
(o) —SO$_2$NR$^{10a}$R$^{11a}$, and
(p) —CN,
(4) halo,
(5) oxo,
(6) hydroxy,
(7) —O—C$_{1-6}$alkyl, which is unsubstituted or substituted with 1-5 substituents where the substituents are each independently selected from:
(a) halo,
(b) hydroxy,
(c) —C$_{3-6}$cycloalkyl,
(d) phenyl,
(e) —CO$_2$R$^9$, and
(f) —NR$^{10}$R$^{11}$,
(8) —CN,
(9) —CO$_2$R$^9$,
(10) —NR$^{10}$R$^{11}$,
(11) —SR$^{12}$,
(12) —S(O)R$^{12}$,
(13) —SO$_2$R$^{12}$,
(14) —SO$_2$NR$^{10a}$R$^{11a}$,
(15) —CONR$^{10a}$R$^{11a}$,
(16) —OCO$_2$R$^9$,
(17) —(NR$^{10a}$)CO$_2$R$^9$,
(18) —O(CO)NR$^{10a}$R$^{11a}$,
(19) —(NR$^9$)(CO)NR$^{10a}$R$^{11a}$,
(20) —(CO)—(CO)NR$^{10a}$R$^{11a}$, and
(21) —(CO)—(CO)OR$^9$;
or where R$^{3a}$ and R$^{3b}$ and the carbon atom(s) to which they are attached join to form a ring selected from cyclobutyl, cyclopentyl, cyclohexyl, cyclopentenyl, cyclohexenyl, azetidinyl, pyrrolidinyl, piperidinyl, azepanyl, tetrahydrofuranyl, tetrahydropyranyl, furanyl, dihydrofuranyl, dihydropyranyl, thienyl, dihydrothienyl, tetrahydrothienyl, dihydrothiopyranyl, tetrahydrothiopyranyl, imidazolyl, imidazolinyl, and piperazinyl, which ring is unsubstituted or substituted with 1-5 substituents independently selected from:
(a) —C$_{1-6}$alkyl, which is unsubstituted or substituted with 1-3 substituents independently selected from:
(i) halo,
(ii) hydroxy,
(iii) —O—C$_{1-6}$alkyl,
(iv) —C$_{3-6}$cycloalkyl,
(v) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl, which phenyl or heterocycle is unsubstituted or substituted with 1-5 substituents each independently selected from:
(I) —C$_{1-6}$alkyl,
(II) —O—C$_{1-6}$alkyl,
(III) halo,
(IV) hydroxy,
(V) trifluoromethyl, and
(VI) —OCF$_3$,
(vi) —CO$_2$R$^9$,
(vii) —NR$^{10}$R$^{11}$,
(viii) —SO$_2$R$^{12}$,
(ix) —CONR$^{10a}$R$^{11a}$, and
(x) —(NR$^{10a}$)CO$_2$R$^9$,
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:
(i) —$C_{1-6}$alkyl, which is unsubstituted or substituted with 1-6 fluoro,
(ii) halo,
(iii) hydroxy,
(iv) —O—$C_{1-6}$alkyl, which is unsubstituted or substituted with 1-6 fluoro, and
(v) —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo;
$A^1$, $A^2$ and $A^3$ are each independently selected from:
(1) a bond,
(2) —$CR^{13}R^{14}$—, wherein $R^{13}$ and $R^{14}$ are each independently selected from:
(a) hydrogen,
(b) $C_{1-6}$ alkyl, which is unsubstituted or substituted with 1-5 substituents each independently selected from:
(i) —$C_{3-6}$cycloalkyl,
(ii) —O—$C_{1-6}$alkyl,
(iii) halo,
(iv) hydroxy, and
(v) phenyl,
(c) hydroxy, and
(d) halo,
(3) —$NR^{10}$—,
(4) —$CR^{13}R^{14}$—$NR^{10}$—,
(5) —$CR^{13}R^{14}$—$CH_2$—,
(6) —$CH_2$—$CR^{13}R^{14}$—,
(7) —O—$CR^{13}R^{14}$—,
(8) —$CR^{13}R^{14}$—O—,
(9) —C≡C—,
(10) —$C(R^{13})$=$C(R^{14})$—, and
(11) —C(=O)—,
or where one or two of $A^1$, $A^2$ and $A^3$ are optionally absent;
0-1 of $A^4$, $A^5$, $A^6$ and $A^7$ is selected from:
(1) —O—,
(2) —C(=O)—
(3) —$N(R^{15})$—, wherein $R^{15}$ is selected from:
(i) hydrogen,
(ii) $C_{1-6}$ alkyl, which is unsubstituted or substituted with 1-5 substituents where the substituents are each independently selected from:
(a) hydroxy,
(b) —O—$C_{1-6}$alkyl,
(c) halo,
(d) —$C_{3-6}$cycloalkyl,
(e) trifluoromethyl, and
(i) phenyl, where the remainder of $A^4$, $A^5$, $A^6$ and $A^7$ are each independently selected from:
(1) a bond, and
(2) —$CR^{13}R^{14}$—,
where one or both of $A^4$ and $A^7$ are optionally absent;
$E^1$ and $E^5$ are each independently selected from:
(1) =$C(R^4)$—,
(2) —$CR^4R^5$—,
(3) —C(=O)—,
(4) —C(=S)—,
(5) =N—,
(6) =$N^+(O^-)$—,
(7) —$N(R^4)$—,
(8) —O—,
(9) —S—, and
(10) —$SO_2$—;
$E^3$ and $E^4$ are each independently selected from:
(1) a bond,
(2) =$C(R^4)$—,
(3) —$CR^4R^5$—,
(4) —C(=O)—,
(5) =N—,
(6) =$N^+(O^-)$—,
(7) —$N(R^4)$—, and
(8) —O—,
where one or both of $E^3$ and $E^4$ are optionally absent;
$E^2$ is selected from:

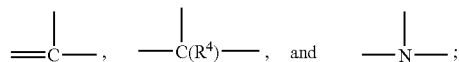

$G^1$ and $G^2$ are each independently selected from:
(1) =$C(R^4)$—,
(2) =N—, and
(3) =$N^+(O^-)$—;
$R^4$ and $R^5$ are each independently selected from:
(1) hydrogen;
(2) —$C_{1-4}$alkyl, which is unsubstituted or substituted with 1-5 substituents each independently selected from:
(a) halo,
(b) hydroxy,
(c) —O—$C_{1-6}$alkyl,
(d) —$C_{3-6}$cycloalkyl,
(e) phenyl,
(f) —$CONR^{10a}R^{11a}$,
(g) —$CO_2R^9$, and
(h) —$NR^{10}R^{11}$,
(3) —$C_{3-6}$cycloalkyl,
(4) phenyl, which is unsubstituted or substituted with 1-3 substituents each independently selected from:
(a) —$C_{1-4}$alkyl, which is unsubstituted or substituted with 1-3 fluoro,
(b) halo,
(c) hydroxy, and
(d) —O—$C_{1-6}$alkyl, which is unsubstituted or substituted with 1-6 fluoro,
(5) halo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,

(13) —OCO$_2$R$^9$, and

(14) —(NR$^{10a}$)CO$_2$R$^9$;

R$^6$ is selected from:

(1) hydrogen, (2) —C$_{1-6}$alkyl or —C$_{3-6}$cycloalkyl which are unsubstituted or substituted with 1-7 substituents each independently selected from:

(a) halo, (b) hydroxy, (c) —O—C$_{1-6}$alkyl, (d) —C$_{3-6}$cycloalkyl, (e) phenyl, which is unsubstituted or substituted with 1-5 substituents each independently selected from:

(i) —C$_{1-6}$alkyl, (ii) —O—C$_{1-6}$alkyl, (iii) halo, (iv) hydroxy, and (v) trifluoromethyl, (f) —CO$_2$R$^9$, (g) —NR$^{10}$R$^{11}$, (h) —CONR$^{10}$R$^{11}$, (i) —SO$_2$R$^{12}$, and (j) trifluoromethyl (3) phenyl or heterocycle, wherein heterocycle is selected from: pyridyl, pyrimidinyl, pyrazinyl, thienyl, and morpholinyl, which is unsubstituted or substituted with 1-5 substituents each independently selected from:

(a) —C$_{1-6}$alkyl, (b) —O—C$_{1-6}$alkyl, (c) halo, (d) hydroxy, and (e) trifluoromethyl;

and pharmaceutically acceptable salts thereof and individual enantiomers and diastereomers thereof.

An embodiment of the present invention includes compounds of the formula Ia:

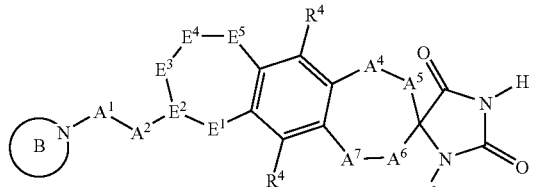

Ia wherein A$^1$, A$^2$, A$^4$, A$^5$, A$^6$, A$^7$, B, E$^1$, E$^2$, E$^3$, E$^4$, E$^5$, R$^4$ and R$^6$ are defined herein;

and pharmaceutically acceptable salts thereof and individual enantiomers and diastereomers thereof.

Another embodiment of the present invention includes compounds of the formula Ib:

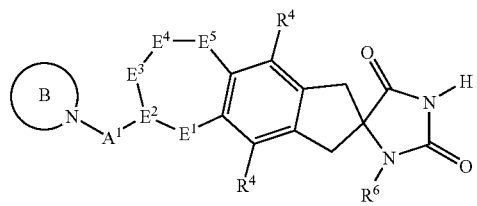

Ib wherein A$^1$, B, E$^1$, E$^2$, E$^3$, E$^4$, E$^5$, R$^4$ and R$^6$ are defined herein;

and pharmaceutically acceptable salts thereof and individual enantiomers and diastereomers thereof.

Another embodiment of the present invention includes compounds of the formula Ic:

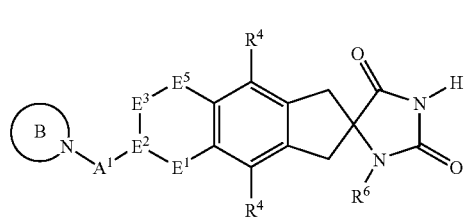

Ic wherein A$^1$, B, E$^1$, E$^2$, E$^3$, E$^5$, R$^4$ and R$^6$ are defined herein;

and pharmaceutically acceptable salts thereof and individual enantiomers and diastereomers thereof.

Another embodiment of the present invention includes compounds of the formula Id:

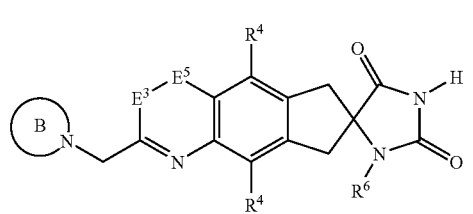

Id wherein B, E$^3$, E$^5$, R$^4$ and R$^6$ are defined herein;

and pharmaceutically acceptable salts thereof and individual enantiomers and diastereomers thereof.

In an embodiment of the present invention B is selected from the group consisting of:

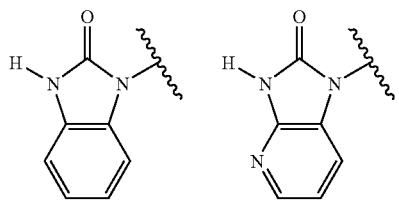

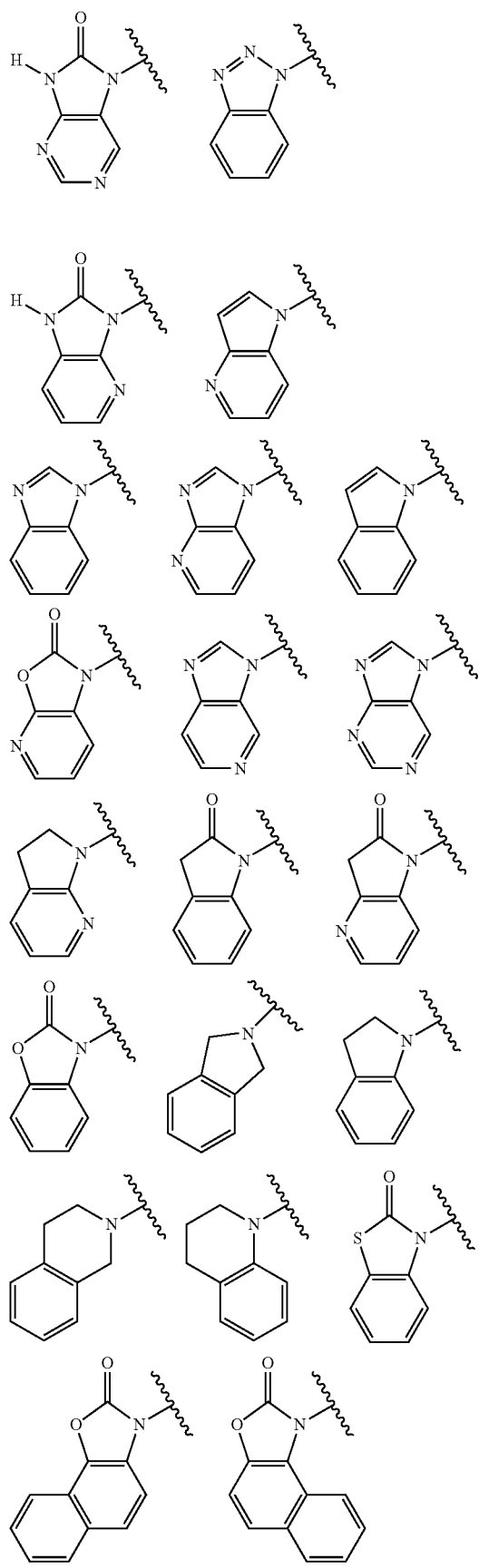
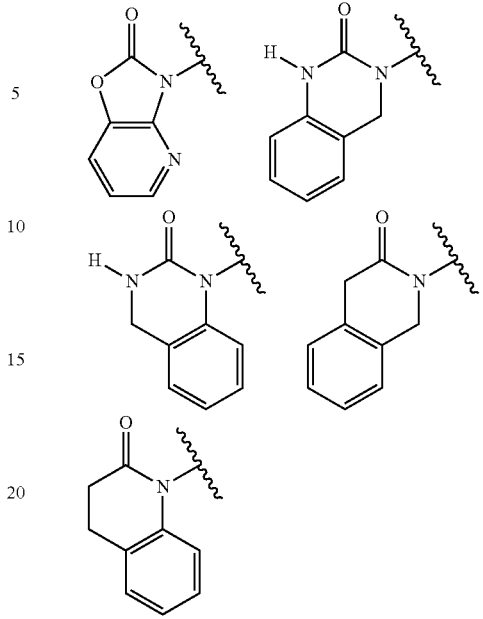

where B is unsubstituted or substituted with 1-5 substituents each independently selected from $R^1$, $R^2$, $R^{3a}$ and $R^{3b}$, where $R^1$, $R^2$, $R^{3a}$ and $R^{3b}$ are defined herein.

In an embodiment of the present invention B is 2-oxobenzimidazolinyl.

In an embodiment of the present invention B is indolyl.

In an embodiment of the present invention B is indolinyl.

In an embodiment of the present invention B is isoindolinyl.

In an embodiment of the present invention B is tetrahydroquinolinyl.

In an embodiment of the present invention B is tetrahydroisoquinolinyl.

In an embodiment of the present invention B is 2-oxoindolinyl.

In an embodiment of the present invention B is 2-oxobenzoxazolinyl.

In an embodiment of the present invention B is azaindolinyl.

In an embodiment of the present invention B is 2-oxoazabenzimidazolinyl.

In an embodiment of the present invention B is phthalimidyl.

In an embodiment of the present invention B is 2-oxotetrahydroquinolinyl.

In an embodiment of the present invention B is benzimidazolyl.

In an embodiment of the present invention $R^1$, $R^2$, $R^{3a}$ and $R^{3b}$ are each independently selected from:
  (1) —$C_{1-6}$alkyl, which is unsubstituted or substituted with 1-5 substituents each independently selected from:
    (a) fluoro,
    (b) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl,
    (c) —$CO_2R^9$, wherein $R^9$ is defined herein,
    (d) —$CONR^{10a}R^{11a}$, wherein $R^{10a}$ and $R^{11a}$ are defined herein, (e) —O—$C_{1-6}$alkyl,
(f) —O—$C_{3-6}$cycloalkyl, and
(g) hydroxy.
(2) phenyl or heterocycle, wherein heterocycle is selected from: pyridinyl, pyrimidinyl, pyrazinyl, thienyl, pyridazinyl, pyrrolidinyl, thiazolyl, isothiazolyl, 2-oxopyrrolidinyl, tetrahydrofuryl, piperidinyl, tetrahydrothienyl, and tetrahydrothiopyranyl, which phenyl or heterocycle is unsubstituted or substituted with 1-5 substituents each independently selected from:
(a) —$C_{1-6}$alkyl, which is unsubstituted or substituted with 1-3 fluoro
(b) halo,
(c) —$CO_2R^9$, wherein $R^9$ is defined herein,
(d) —(CO)$R^9$,
(e) —$CONR^{10a}R^{11a}$, wherein $R^{10a}$ and $R^{11a}$ are defined herein,
(f) —O—$C_{1-6}$alkyl, which is unsubstituted or substituted with 1-3 fluoro,
(g) hydroxy,
(h) oxo,
(i) —S—$C_{1-4}$alkyl,
(j) —S(O)—$C_{1-4}$alkyl, and
(k) —$SO_2$—$C_{1-4}$alkyl,
(3) halo,
(4) hydroxy,
(5) —O—$C_{1-6}$alkyl, which is unsubstituted or substituted with 1-3 fluoro,
(6) —$NH_2$,
(7) —$C_{3-6}$cycloalkyl,
(8) —(CO)—(CO)$NR^{10a}R^{11a}$, wherein $R^{10a}$ and $R^{11a}$ are defined herein,
(9) —CN, and
(10) —$SO_2NR^{10a}R^{11a}$, wherein $R^{10a}$ and $R^{11a}$ are defined herein.

In an embodiment of the present invention $R^1$ and $R^2$ are each independently selected from:
(1) —$C_{1-4}$alkyl, which is unsubstituted or substituted with 1-5 substituents each independently selected from:
(a) fluoro,
(b) phenyl,
(c) —$CO_2R^9$, wherein $R^9$ is defined herein,
(d) —$CONR^{10a}R^{11a}$, wherein $R^{10a}$ and $R^{11a}$ are defined herein,
(e) —O—$C_{3-6}$cycloalkyl,
(2) phenyl or heterocycle, wherein heterocycle is selected from: pyridinyl, pyrimidinyl, pyrazinyl, pyridazinyl, pyrrolidinyl, thiazolyl, tetrahydrofuryl, piperidinyl, and tetrahydrothiopyranyl, which phenyl or heterocycle is unsubstituted or substituted with 1-5 substituents each independently selected from:
(a) —$C_{1-4}$alkyl, which is unsubstituted or substituted with 1-3 fluoro
(b) halo,
(c) —$CO_2R^9$, wherein $R^9$ is defined herein,
(d) —(CO)$R^9$, wherein $R^9$ is defined herein,
(e) —$CONR^{10a}R^{11a}$, wherein $R^{10a}$ and $R^{11a}$ are defined herein,
(f) —O—$C_{1-4}$alkyl, which is unsubstituted or substituted with 1-3 fluoro,
(g) hydroxy,
(h) oxo
(i) —S—$C_{1-4}$alkyl,
(j) —S(O)—$C_{1-4}$alkyl, and
(k) —$SO_2$—$C_{1-4}$alkyl,
(3) halo,
(4) hydroxy,
(5) —O—$C_{1-4}$alkyl, which is unsubstituted or substituted with 1-3 fluoro,
(6) —CN,
(7) —$C_{3-6}$cycloalkyl,
(8) —(CO)—(CO)$NR^{10a}R^{11a}$, wherein $R^{10a}$ and $R^{11a}$ are defined herein,
(9) —$SO_2NR^{10a}R^{11a}$, wherein $R^{10a}$ and $R^{11a}$ are defined herein.

In an embodiment of the present invention, $R^{3a}$ and $R^{3b}$ and the carbon atom(s) to which they are attached join to form a ring selected from piperidinyl, cyclohexyl, cyclopentyl, pyrrolidinyl, tetrahydrofuranyl, tetrahydropyranyl, tetrahydrothienyl, and tetrahydrothiopyranyl, which ring is unsubstituted or substituted with 1-3 substituents independently selected from:
(a) —$C_{1-6}$alkyl, which is unsubstituted or substituted with 1-3 substituents each independently selected from:
(i) halo, and
(ii) phenyl,
(b) phenyl or heterocycle, wherein heterocycle is selected from: pyridinyl, pyrimidinyl and pyrazinyl,
(c) —$CO_2R^9$, wherein $R^9$ is defined herein,
(d) hydroxy, and
(e) oxo.

In an embodiment of the present invention, $R^{3a}$ and $R^{3b}$ and the carbon atom(s) to which they are attached join to form a ring selected from piperidinyl, cyclohexyl, tetrahydropyranyl, and tetrahydrothiopyranyl, which ring is unsubstituted or substituted with 1-3 substituents independently selected from:
(a) —$C_{1-6}$alkyl, which is unsubstituted or substituted with 1-3 substituents independently selected from:
(i) fluoro, and
(ii) phenyl,
(b) —$CO_2$—$C_{1-4}$alkyl,
(c) —$CO_2$-benzyl,
(d) hydroxyl, and
(e) oxo.

In an embodiment of the present invention $A^1$ is $CH_2$.
In an embodiment of the present invention $A^1$ is a bond.
In an embodiment of the present invention $A^1$ is —C(=O)—.
In an embodiment of the present invention $A^2$ is $CH_2$.
In an embodiment of the present invention $A^2$ is a bond.
In an embodiment of the present invention $A^3$ is a bond.
In an embodiment of the present invention $A^4$ is selected from: $CH_2$; and a bond.
In an embodiment of the present invention $A^4$ is a bond.
In an embodiment of the present invention $A^5$ is $CH_2$.
In an embodiment of the present invention $A^6$ is $CH_2$.
In an embodiment of the present invention $A^7$ is selected from: $CH_2$; and a bond.
In an embodiment of the present invention $A^7$ is a bond.
In an embodiment of the present invention $E^1$ is selected from: =C($R^4$)—; —$CR^4R^5$—; =N—; and —N($R^4$)—; wherein $R^4$ and $R^5$ are defined herein.
In an embodiment of the present invention $E^1$ is selected from: —N—; and —N(H)—.
In an embodiment of the present invention $E^5$ is selected from: =C($R^4$)—; —$CR^4R^5$—; =N—; and —N($R^4$)—; wherein $R^4$ and $R^5$ are defined herein.
In an embodiment of the present invention $E^5$ is selected from: =C(H)—; —$CH_2$—; =N—; and —N(H)—.
In an embodiment of the present invention $E^3$ is selected from: a bond; =C($R^4$)—; —$CR^4R^5$—; =N—; and —N($R^4$)—; wherein $R^4$ and $R^5$ are defined herein.

In an embodiment of the present invention $E^3$ is selected from: a bond; =C(H)—; =N—; and —N(H)—.

In an embodiment of the present invention $E^4$ is selected from: a bond; and —CH$_2$—.

In an embodiment of the present invention $E^4$ is a bond.

In an embodiment of the present invention $E^2$ is selected from:

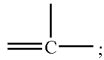

and

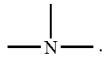

In an embodiment of the present invention $E^2$ is

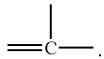

In an embodiment of the present invention $G^1$ is =C(H)—.

In an embodiment of the present invention $G^1$ is =C(R$^4$)—, wherein R$^4$ is defined herein.

In an embodiment of the present invention $G^2$ is =C(H)—.

In an embodiment of the present invention $G^2$ is =C(R$^4$)—, wherein R$^4$ is defined herein.

In an embodiment of the present invention $R^4$ and $R^5$ are independently selected from:
(1) hydrogen;
(2) —C$_{1-4}$alkyl, which is unsubstituted or substituted with 1-3 substituents each independently selected from:
  (a) halo,
  (b) hydroxy,
  (c) —O—C$_{1-6}$alkyl,
  (d) —C$_{3-6}$cycloalkyl, and
  (e) phenyl,
(3) —C$_{3-6}$cycloalkyl,
(4) phenyl, which is unsubstituted or substituted with 1-3 substituents each independently selected from:
  (a) —C$_{1-4}$alkyl, which is unsubstituted or substituted with 1-3 fluoro, and
  (b) halo,
(5) halo,
(6) hydroxy,
(7) —O—C$_{1-6}$alkyl, which is unsubstituted or substituted with 1-3 fluoro,
(8) —CN, and
(9) —NR$^{10}$R$^{11}$;

In an embodiment of the present invention $R^4$ and $R^5$ are independently selected from:
(1) hydrogen;
(2) —C$_{1-4}$alkyl, which is unsubstituted or substituted with 1-3 fluoro,
(3) phenyl,
(4) halo, and
(5) hydroxy;

In an embodiment of the present invention $R^4$ and $R^5$ are independently selected from: hydrogen, halo, and methyl.

In an embodiment of the present invention $R^4$ is hydrogen.

In an embodiment of the present invention $R^5$ is hydrogen.

In an embodiment of the present invention $R^6$ is selected from:
(1) hydrogen,
(2) —C$_{1-4}$alkyl which is unsubstituted or substituted with 1-5 substituents each independently selected from:
  (a) halo,
  (b) hydroxy,
  (c) —C$_{3-6}$cycloalkyl, and
  (d) phenyl,
(3) phenyl or heterocycle, wherein heterocycle is selected from: pyridyl, pyrimidinyl, and pyrazinyl, In an embodiment of the present invention $R^6$ is selected from:
(1) hydrogen,
(2) —C$_{1-4}$alkyl which is unsubstituted or substituted with 1-3 substituents each independently selected from:
  (a) halo, and
  (b) phenyl.

In an embodiment of the present invention $R^6$ is hydrogen or methyl.

In an embodiment of the present invention $R^6$ is methyl.

In an embodiment of the present invention $R^9$ is independently selected from:
(i) hydrogen,
(ii) —C$_{1-5}$alkyl, which is unsubstituted or substituted with 1-5 substituents, substituents each independently selected from:
  (I) halo,
  (II) hydroxy,
  (III) —O—C$_{1-6}$alkyl,
  (IV) —C$_{3-6}$cycloalkyl,
  (V) phenyl, which is unsubstituted or substituted with 1-4 substituents each independently selected from:
    (1) —C$_{1-4}$alkyl,
    (2) —O—C$_{1-4}$alkyl, and
    (3) halo,
(iii) —C$_{3-6}$cycloalkyl, and
(iv) phenyl or heterocycle, wherein heterocycle is selected from: pyridinyl, pyrimidinyl, pyrazinyl, thienyl, pyrrolidinyl, thiazolyl, oxazolyl, imidazolyl, triazolyl, tetrazolyl, indolinyl, indolyl, quinolinyl, isoquinolinyl, tetrahydroquinolinyl, isoindolinyl, tetrahydroisoquinolinyl, tetrahydrofuryl, piperidinyl, piperazinyl, and morpholinyl, which phenyl or heterocycle is unsubstituted or substituted with 1-5 substituents each independently selected from:
  (I) halo,
  (II) —C$_{1-4}$alkyl, which is unsubstituted or substituted with 1-3 halo,
  (III) —O—C$_{1-4}$alkyl, which is unsubstituted or substituted with 1-3 halo,
  (IV) —C$_{3-6}$cycloalkyl,
  (V) oxo,
  (VI) —CN, and
  (VII) hydroxy.

In an embodiment of the present invention $R^9$ is independently selected from:
(i) hydrogen,
(ii) —C$_{1-4}$alkyl, which is unsubstituted or substituted with 1-3 substituents, substituents each independently selected from:
  (I) halo,
  (II) hydroxy, (III) —O—$C_{1-4}$alkyl, and
(IV) phenyl, which is unsubstituted or substituted with 1-4 substituents each independently selected from:
  (1) —$C_{1-4}$alkyl,
  (2) —O—$C_{1-4}$alkyl, and
  (3) halo,
(iii) —$C_{3-6}$cycloalkyl, and
(iv) phenyl or heterocycle, wherein heterocycle is selected from: pyridinyl, pyrimidinyl, pyrazinyl, thienyl, pyrrolidinyl, indolinyl, indolyl, quinolinyl, isoquinolinyl, tetrahydroquinolinyl, isoindolinyl, tetrahydroisoquinolinyl, piperidinyl, piperazinyl, and morpholinyl, which phenyl or heterocycle is unsubstituted or substituted with 1-4 substituents each independently selected from:
  (I) halo,
  (II) —$C_{1-4}$alkyl, which is unsubstituted or substituted with 1-3 fluoro, and
  (III) —O—$C_{1-4}$alkyl.

In an embodiment of the present invention $R^{10}$ and $R^{11}$ are each independently selected from:
(i) hydrogen,
(ii) —$C_{1-5}$alkyl, which is unsubstituted or substituted with 1-5 substituents each independently selected from:
  (I) —O—$C_{1-4}$alkyl,
  (II) halo,
  (III) hydroxy, and
  (IV) —$OCF_3$,
(iii) —$C_{4-6}$cycloalkyl,
(iv) phenyl, which is unsubstituted or substituted with 1-4 substituents each independently selected from:
  (I) —$C_{1-4}$alkyl,
  (II) —O—$C_{1-4}$alkyl,
  (III) halo,
  (IV) trifluoromethyl, and
  (v) —$OCF_3$, and
(v) benzyl, which is unsubstituted or substituted with 1-4 substituents each independently selected from:
  (I) —$C_{1-4}$alkyl,
  (II) —O—$C_{1-4}$alkyl,
  (III) halo, and
  (IV) trifluoromethyl,
(vi) —$COR^9$, and
(vii) —$SO_2R^{12}$.

In an embodiment of the present invention $R^{10}$ and $R^{11}$ are each independently selected from:
(i) hydrogen,
(ii) —$C_{1-4}$alkyl,
(iii) phenyl,
(iv) benzyl, and
(v) —$COR^9$.

In an embodiment of the present invention $R^{10a}$ and $R^{11a}$ are each independently selected from:
(i) hydrogen,
(ii) —$C_{1-4}$alkyl, which is unsubstituted or substituted with 1-4 substituents each independently selected from:
  (I) halo, and
  (II) hydroxy,
(iii) —$C_{5-6}$cycloalkyl,
(iv) phenyl, which is unsubstituted or substituted with 1-4 substituents each independently selected from:
  (I) —$C_{1-4}$alkyl,
  (II) —O—$C_{1-4}$alkyl,
  (III) halo, and
  (V) trifluoromethyl,
(v) benzyl, which is unsubstituted or substituted with 1-4 substituents each independently selected from:
  (I) —$C_{1-4}$alkyl,
  (II) —O—$C_{1-4}$alkyl,
  (III) halo, and
  (IV) trifluoromethyl,
or where $R^{10a}$ and $R^{11a}$ join to form a ring selected from azetidinyl, pyrrolidinyl, piperidinyl, piperazinyl, and morpholinyl, which ring is unsubstituted or substituted with 1-3 substituents each independently selected from:
  (I) —$C_{1-4}$alkyl
  (II) —O—$C_{1-4}$alkyl
  (III) halo
  (IV) hydroxy,
  (V) phenyl,
  (VI) benzyl, and
  (VII) —$COR^9$.

In an embodiment of the present invention $R^{10a}$ and $R^{11a}$ are each independently selected from:
(i) hydrogen,
(ii) —$C_{1-4}$alkyl,
(iii) phenyl, and
(iv) benzyl,
or where $R^{10a}$ and $R^{11a}$ join to form a ring selected from pyrrolidinyl, piperidinyl, piperazinyl, and morpholinyl, which ring is unsubstituted or substituted with 1-3 substituents each independently selected from:
  (I) —$C_{1-4}$alkyl
  (II) halo
  (III) hydroxy, and
  (IV) phenyl.

In an embodiment of the present invention $R^{12}$ is selected from:
(i) —$C_{1-4}$alkyl, which is unsubstituted or substituted with 1-3 fluoro,
(ii) —$C_{3-6}$cycloalkyl,
(iii) phenyl which is unsubstituted or substituted with 1-3 substituents each independently selected from:
  (I) —$C_{1-4}$alkyl,
  (II) —O—$C_{1-14}$alkyl,
  (III) halo, and
  (IV) trifluoromethyl,
(iv) benzyl, which is unsubstituted or substituted with 1-3 substituents each independently selected from:
  (I) —$C_{1-4}$alkyl,
  (II) —O—$C_{1-4}$alkyl,
  (III) halo, and
  (IV) trifluoromethyl In embodiments of the invention where $R^6$ is —$CH_3$, $A^4$ and $A^7$ are absent, $A^5$ and $A^6$ are —$CH_2$—, $G^1$ and $G^2$ are —C(H)—, $E^1$ is =N—, $E^2$ is

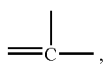

$E^3$ is =C(H)—, $E^4$ is absent, $E^5$ is —C(H)—, $A^1$ is —$CH_2$— and $A^2$ and $A^3$ are absent, the following structure forms:

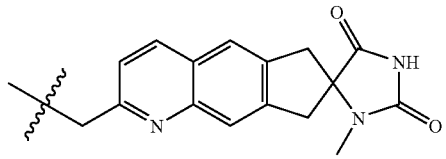

In embodiments of the invention where $R^6$ is —$CH_3$, $A^4$ and $A^7$ are absent, $A^5$ and $A^6$ are —$CH_2$—, $G^1$ and $G^2$ are =C(H)—, $E^1$ is —N(H)—, $E^2$ is

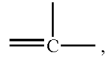

$E^3$ and $E^4$ are absent, $E^5$ is =N—, $A^1$ is —$CH_2$— and $A^2$ and $A^3$ are absent, the following structure forms:

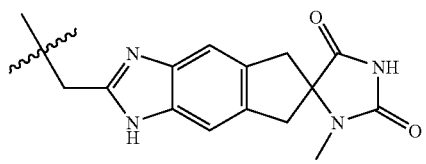

In embodiments of the invention where $R^6$ is —$CH_3$, $A^4$ and $A^7$ are absent, $A^5$ and $A^6$ are —$CH_2$—, $G^1$ and $G^2$ are =C(H)—, $E^1$ is =N—, $E^3$ and $E^4$ are absent, $E^2$ is

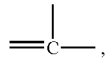

$E^5$ is —O—, $A^1$ is —$CH_2$— and $A^2$ and $A^3$ are absent, the following structure forms:

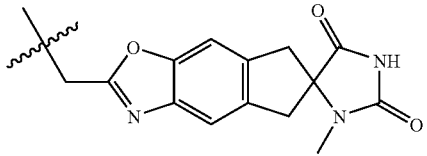

In embodiments of the invention where $R^6$ is —$CH_3$, $A^4$ and $A^7$ are absent, $A^5$ and $A^6$ are —$CH_2$—, $G^1$ and $G^2$ are =C(H)—, $E^1$ is =N—, $E^2$ is

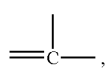

$E^3$ is =C(H)—, $E^4$ is absent, $E^5$ is =N—, $A^1$ is —$CH_2$— and $A^2$ and $A^3$ are absent, the following structure forms:

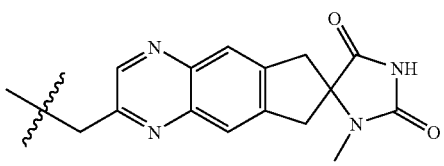

In embodiments of the invention where $R^6$ is —$C_3$, $A^4$ and $A^7$ are absent, $A^5$ and $A^6$ are —$CH_2$—, $G^1$ and $G^2$ are =C(H)—, $E^1$ is =N—, $E^2$ is

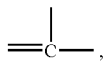

$E^3$ is =C(H)—, $E^4$ is absent, $E^5$ is =C(H)—, $A^1$ is —C(=O)—, and $A^2$ and $A^3$ are absent, the following structure forms:

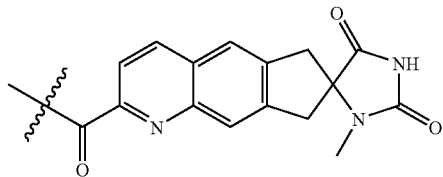

In embodiments of the invention where $R^6$ is —$CH_3$, $A^4$ and $A^7$ are absent, $A^5$ and $A^6$ are —$CH_2$—, $G^1$ and $G^2$ are =C(H)—, $E^1$ is —N(H)—, $E^2$ is

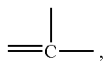

$E^3$ and $E^4$ are absent, $E^5$ is =N—, $A^1$ and $A^2$ are —$CH_2$—, and $A^3$ is absent, the following structure forms:

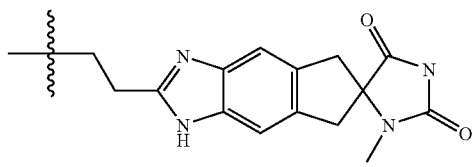

In certain embodiments of the invention where B is:

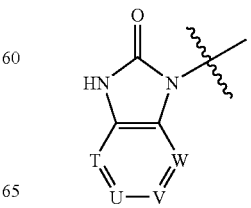

and T and V are each carbon substituted with methyl, and U and W are each carbon, the following structure forms:

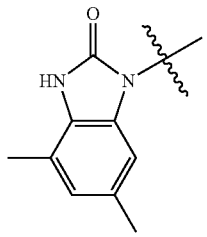

In certain embodiments of the invention where B is:

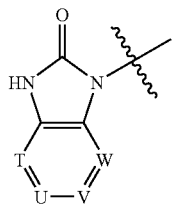

and is substituted with —CH$_2$C(O)N(CH$_3$)$_3$, and T and V are each carbon substituted with methyl, and U and W are each carbon, the following structure forms:

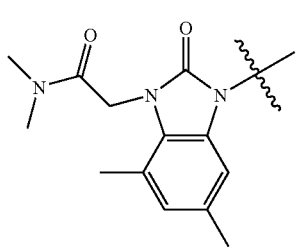

In certain embodiments of the invention where B is:

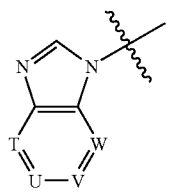

and T, U, V and W are each carbon, the following structure forms:

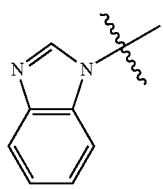

In certain embodiments of the invention where B is:

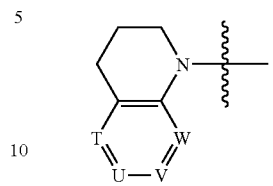

and T, U, V and W are each carbon, the following structure forms:

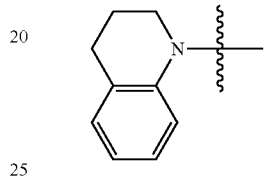

In certain embodiments of the invention where B is:

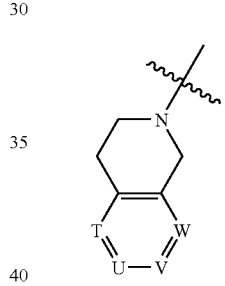

and T, U, V and W are each carbon, the following structure forms:

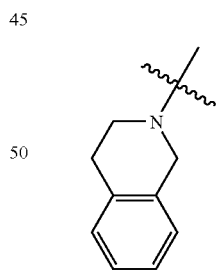

In certain embodiments of the invention where B is:

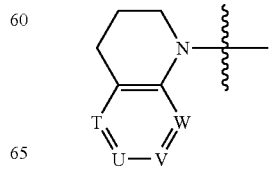

substituted with —CH₃ and T, U, V and W are each carbon, the following structure forms:

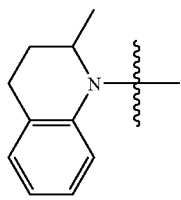

In certain embodiments of the invention where B is:

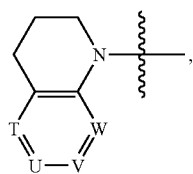

U is carbon substituted with —OCH₃ and T, V and W are each carbon, the following structure forms:

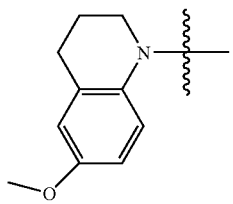

In certain embodiments of the invention where B is:

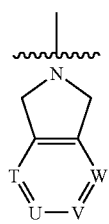

and T, U, V and W are each carbon, the following structure forms:

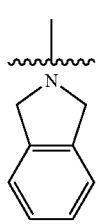

In certain embodiments of the invention where B is:

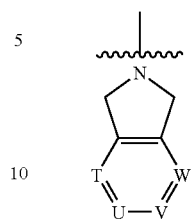

substituted twice with oxo, and T, U, V and W are are each carbon, the following structure forms:

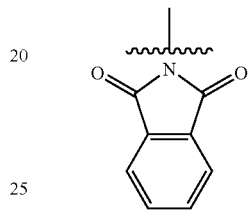

In certain embodiments of the invention where B is:

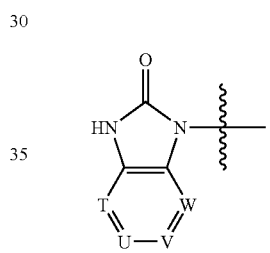

and T, U, V and W are each carbon, the following structure forms:

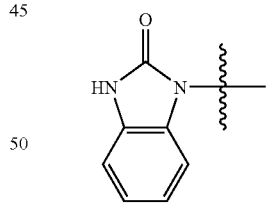

In certain embodiments of the invention where B is:

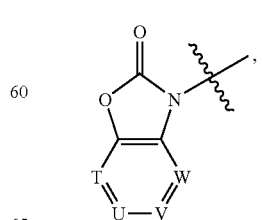

T is carbon substituted with bromine, and, U, V and W are each carbon, the following structure forms:

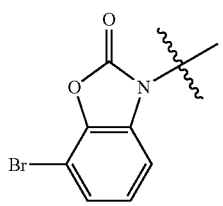

In certain embodiments of the invention where B is:

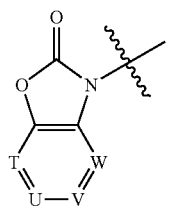

U and W are each carbon, and T and V are each carbon substituted with methyl, the following structure forms:

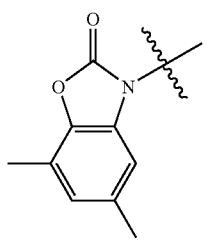

In certain embodiments of the invention where B is:

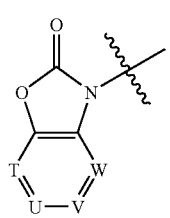

and T, U, V and W are each carbon, the following structure forms:

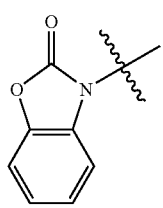

In certain embodiments of the invention where B is:

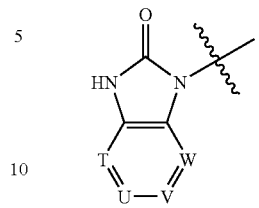

substituted with methyl, V is nitrogen and T, U and W are each carbon, the following structure forms:

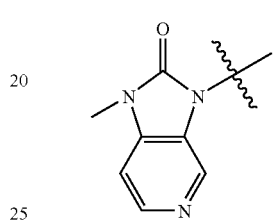

In certain embodiments of the invention where B is:

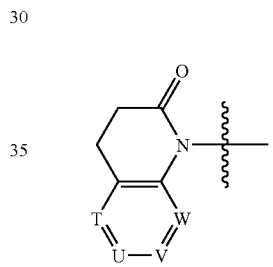

and T, U, V and W are each carbon, the following structure forms:

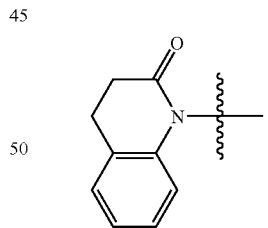

In certain embodiments of the invention where B is:

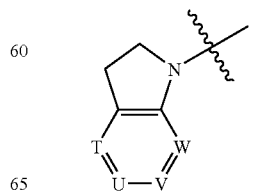

W is nitrogen and T, U and V are each carbon, the following structure forms:

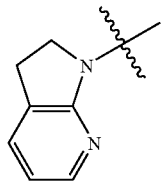

In certain embodiments of the invention where B is:

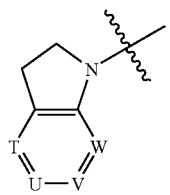

where B is substituted with benzyl, and T, U, V and W are each carbon, the following structure forms:

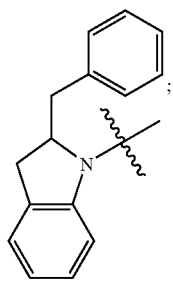

where W is carbon substituted with —SO₂N(CH₃)₂, and T, U and V are each carbon, the following structure forms:

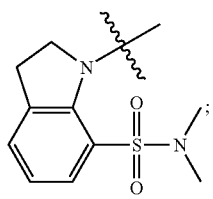

where U is substituted with cyano and T, V and W are each carbon, the following structure forms:

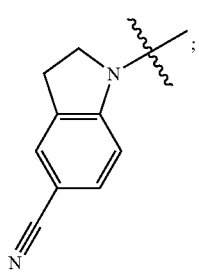

where B is substituted with —CH(OH)-(phenyl), and T, U, V and W are each carbon, the following structure forms:

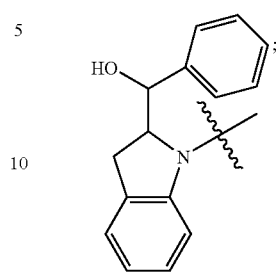

where U is carbon substituted with fluorine and T, V and W are each carbon, the following structure forms:

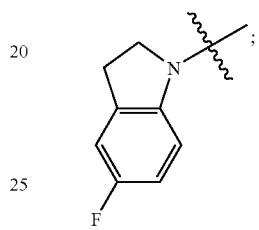

where V is carbon substituted with —CF₃, and T, U and W are each carbon, the following structure forms:

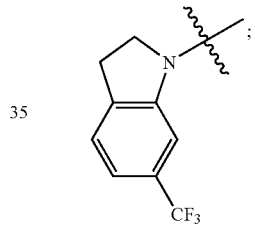

where U is carbon substituted with chlorine and T, V and W are each carbon, the following structure forms:

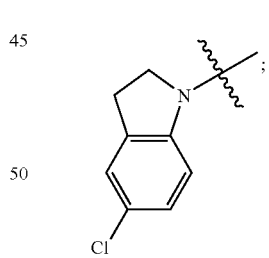

where B is substituted with —CH₂(OH), and T, U, V and W are each carbon, the following structure forms:

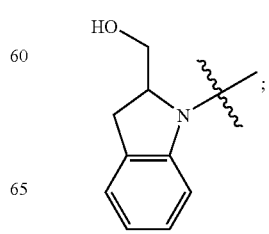

where T, U, V and W are each carbon, the following structure forms:

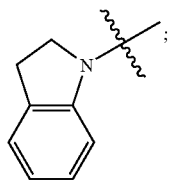

and
where B is substituted with piperidinyl, where piperidinyl is substituted with —C(O)OR$^9$ and R$^9$ is benzyl, and T, U, V and W are each carbon, the following structure forms:

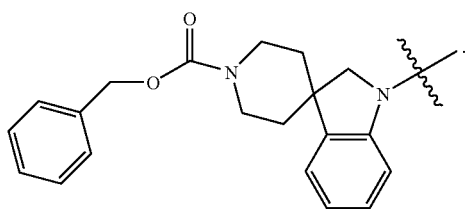

It is to be understood that where one or more of the above recited structures or substructures recite multiple substituents having the same designation each such variable may be the same or different from each similarly designated variable. For example, R$^4$ is recited twice in each of formulae Ia through Ie above, and each R$^4$ in formula I may independently be any of the substructures defined under R$^4$. The invention is not limited to structures and substructures wherein each R$^4$ must be the same for a given structure. The same is true with respect to any variable appearing multiple times in a structure or substructure.

It is also to be understood with reference to the preceeding embodiments that additional embodiments are contemplated wherein a moiety is substituted at position other than as depicted above. As examples of such positional isomers, the invention contemplates not only the moiety:

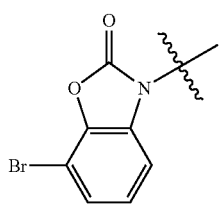

but also the moieties:

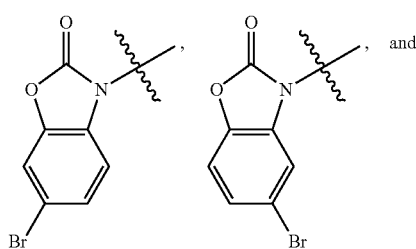

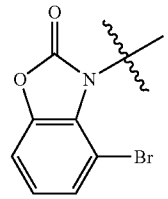

Similarly, the invention contemplates not only the moiety:

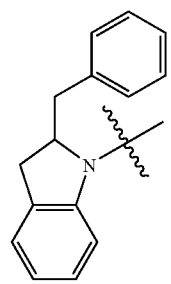

but also the moieties:

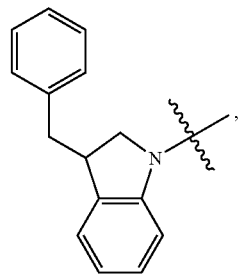

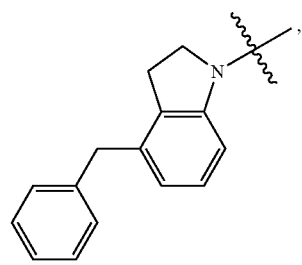

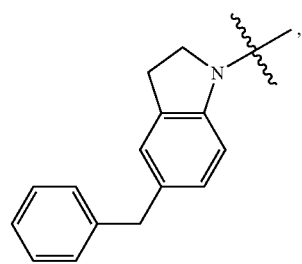

-continued

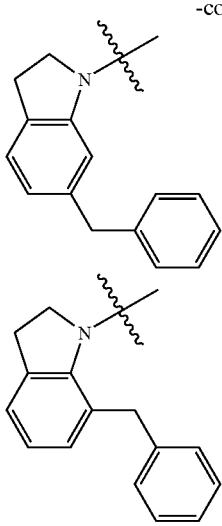

and

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronaphthyl, indanyl, or biphenyl.

The term "heterocycle" or "heterocyclic", as used herein except where noted, represents a stable 4- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The terms "bond" and "absent" are in certain instances herein used interchangeably to refer to an atom (or chemical moiety) which is not present in a particular embodiment of the invention. In such embodiments, the atoms adjacent the "bond" or "absent" atom are simply bonded to one another. For example, in certain embodiments of the invention described and claimed herein, where $-A^1-A^2-A^3$-links B to $E^2$, $A^1$ is defined as $CR^{13}R^{14}$ while $A^2$ and $A^3$ are described as "absent". In such a molecule, it is understood that $A^1$ is bonded directly to the moiety adjacent $A^3$, i.e. the moiety $E^2$, resulting in the sub-structure $B-A^1-E^2$. The absence of a specific atom or moiety, particularly an atom or moiety which serves to link or connect other atoms or moieties, does not imply that such other atoms or moieties are not linked.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 0.1 ml of binding buffer [10 mM HEPES, pH 7.4, 5 mM $MgCl_2$ and 0.2% bovine serum albumin (BSA)] containing 10 µM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 µl) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 µg/ml streptomycin at 37° C., 95% humidity, and 5% $CO_2$. For cAMP assays, cells were plated at $5\times10^5$ cells/well in 96-well poly-D-lysine-coated plates (Becton-Dickinson) and cultured for ~18 h before assay. Cells were washed with phosphate-buffered saline (PBS, Sigma) then pre-incubated with 300 µM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMPS (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 $cm^2$ flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM $MgCl_2$, and 0.2% BSA) for 3 hours at room temperature containing 10 µM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% I_{max}/100)}{1 + ([\text{Drug}]/K_i(1 + [\text{Radiolabel}]/K_d)^{nH}}$$

Where Y is observed CPM bound, $Y_{max}$ is total bound counts, Y min is non specific bound counts, (Y max−Y min) is specific bound counts, % I max is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After (X-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lomoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sulfentanil, methadone, acetyl methanol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a brakykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a rennin inhibitor; a granzyme B inhibitor; a substance P antagonist; an endothelin antagonist; a norepinephrine precursor; anti-anxiety agents such as diazepam, alprazolam, chlordiazepoxide and chlorazepate; serotonin 5$HT_2$ receptor antagonists; opiod agonists such as codeine, hydrocodone, tramadol, dextropropoxyphene and fentanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example miontelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propranolol, atenolol, metoprolol or nadolol, and the like; a MAO inhibitor, for example phenelzine; a calcium channel blocker, for example flunarizine, diltiazem, amlodipine, felodipine, nisoldipine, isradipine, nimodipine, lomerizine, verapamil, nifedipine, or prochlorperazine; neuroleptics such as olanzapine, droperidol, prochlorperazine, chlorpromazine and quetiapene; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1-0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 10 milligrams to about 1000 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of spirohydantoin intermediates may be conducted as described in Schemes 1-9. Spirohydantoin intermediates bearing $R^4$, $R^5$, $R^{13}$, $R^{14}$ and $R^{15}$ may be prepared by employing appropriately substituted starting materials or by derivatization of any intermediates and/or final products as desired by methods known in the art.

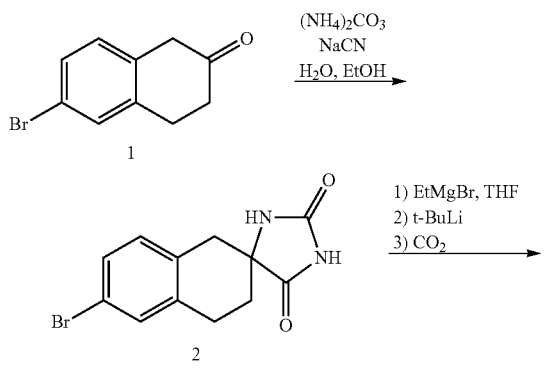

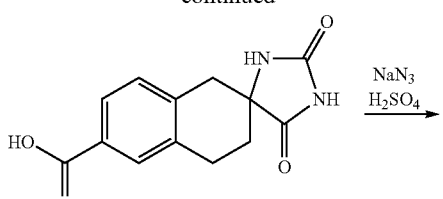

3

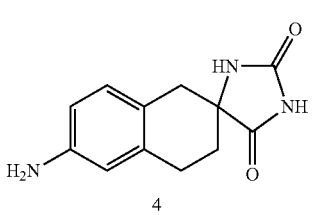

4

Commercially available 6-bromo-2-tetralone 1 may be readily converted to the spirohydantoin 2 under Bucherer-Bergs conditions, using ammonium carbonate and either sodium cyanide or potassium cyanide. Other 2-tetralones may be readily accessed using a variety of literature methods, such as the Friedel-Crafts reaction of arylacetyl chlorides with ethene as described by Burckhalter and Campbell (*J. Org Chem.* 1961, 26, 4232) and converted to the corresponding spirohydantoins analogously. In Scheme 1, treatment of spirohydantoin 2 with ethyl magnesium bromide followed by tert-butyllithium effects metal-halogen exchange and the resulting aryllithium species is quenched with carbon dioxide to give acid 3. A Schmidt reaction of 3 with hydrazoic acid may be used to provide aniline 4, as reviewed by Wolff (*Org. React,* 1946, 3, 307). Alternatively, a modified Curtius rearrangement using 3 and diphenylphosphoryl azide according to the procedure of Yamada and coworkers (*Tetrahedron* 1974, 30, 2151) can provide aniline 4 via either its tert-butyl or benzyl carbamate derivatives.

SCHEME 2

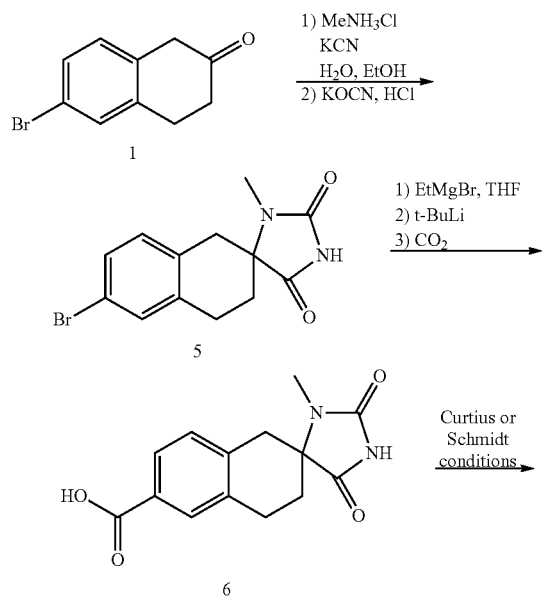

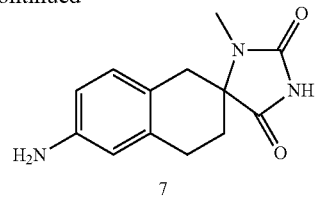

7

In Scheme 2, treatment of 6-bromo-2-tetralone 1 with methylamine hydrochloride and potassium cyanide, followed by potassium cyanate and hydrochloric acid, provides the methylated hydantoin derivative 5. Analogous procedures to those described in Scheme 1 may be used to provide acid 6 and aniline 7.

Scheme 3 illustrates a route to 7-substituted tetralin derivatives 10 and 11. 3-Bromophenylacetic acid is converted to the corresponding acid chloride and this is subjected to Friedel-Crafts reaction with ethene, affording the 7-bromo-2-tetralone 9. This intermediate may be elaborated using the procedures described in Scheme 1 to provide the acid 10 and aniline 11.

SCHEME 3

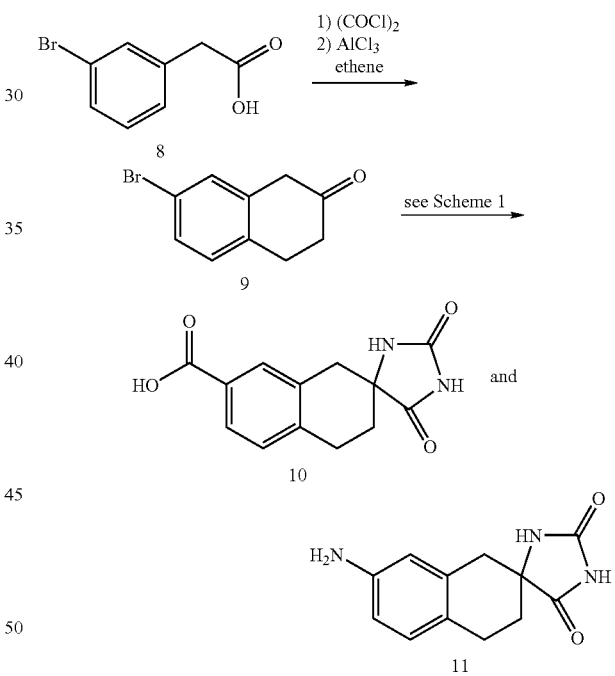

Scheme 4 details the synthesis of the key indane-based spirohydantoin intermediates. 2-Indanone 12 is converted to the spirohydantoin 13 via Bucherer-Bergs chemistry as shown. Treatment of 13 with nitric acid provides the 5-nitroindane derivative 14, which may be reduced to the corresponding aniline 15 under catalytic hydrogenation conditions. Alternatively, a two-step process can be employed to convert 2-indanone 12 into the N-methylspirohydantoin 16. Treatment of 12 with potassium cyanide and methylamine hydrochloride affords an amino nitrile which is converted to the spirohydantoin 16 using potassium cyanate and acetic acid. Subjection of 16 to the nitration-reduction sequence used for 13 leads to the corresponding aniline 18, as detailed in Scheme 4.

SCHEME 4

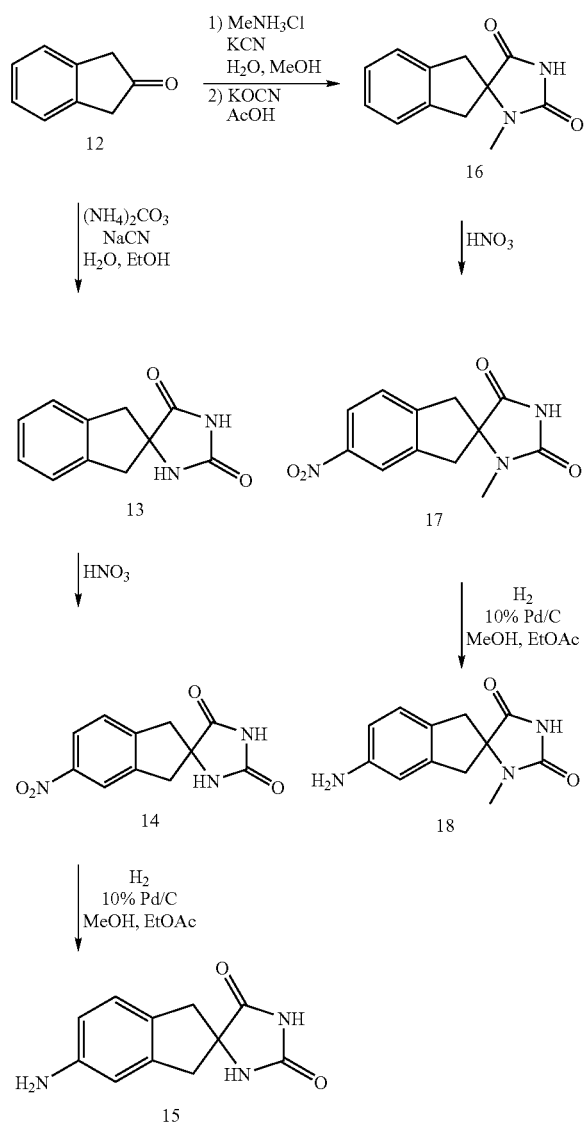

Spirohydantoin intermediates may be resolved to give pure enantiomers using techniques familiar to those skilled in the art. For example, chromatography of the nitro intermediate 17 on a Chiralpak AD column can be used to provide the individual enantiomers (R)-17 and (S)-17, and these enantiomers may be reduced to the corresponding anilines [(R)-18 and (S)-18] by catalytic hydrogenation. Use of standard coupling procedures using enantiomerically pure anilines affords the individual enantiomers of the final products. Resolution may be effected by other methodologies, such as fractional crystallization of diastereomeric salts, and it may be carried out on other synthetic intermediates or on the final products. Alternatively, an asymmetric synthesis of a key intermediate, such as an amino acid precursor of a spirohydantoin, could be used to provide an enantiomerically enriched final product.

Spirohydantoin compounds containing $R^6$ substituents other than hydrogen or methyl may be prepared by methods analogous to those for the cases where $R^6$ is methyl in Scheme 2 and Scheme 4. Alternatively, a suitably protected spirohydantoin intermediate may be derivatized as shown in Scheme 5.

SCHEME 5

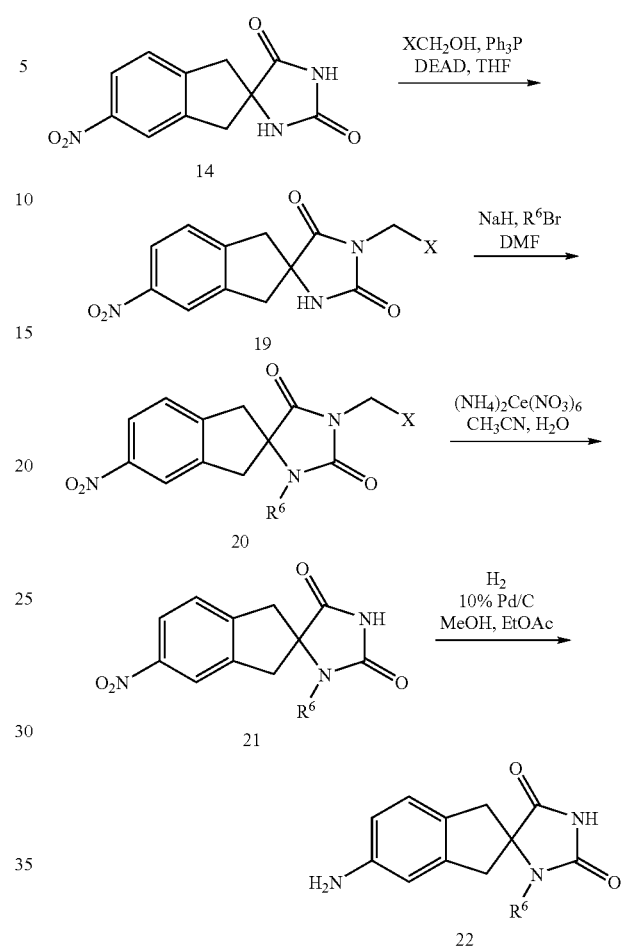

The route illustrated in Scheme 5 uses a Mitsunobu reaction to selectively protect the imide nitrogen of spirohydantoin 14 with, for example, X=4-methoxyphenyl. Other alkylation conditions may also be employed in this protection step. The protected spirohydantoin 19 may be alkylated with a variety of $R^6$ groups using sodium hydride or another base to deprotonate the spirohydantoin. In the example shown, the bromide $R^6Br$ is utilized to effect the alkylation, but a variety of other $R^6$ derivatives, such as chlorides or sulfonates may be used. Other conditions, such as copper or palladium promoted arylation or heteroarylation reactions may also be employed to install aryl or heteroaryl $R^6$ groups. The spirohydantoin product 20 is then deprotected to give 21. In Scheme 5, ammonium cerium (IV) nitrate is used to remove the 4-methoxybenzyl protecting group but the choice of deprotection conditions may vary depending on the nature of X. Finally, hydrogenation conditions may be used to provide intermediate 22, in analogy with the previous Schemes.

Aniline intermediates, such as those described in Schemes 1-5, may be converted to a variety of other key intermediates that are useful in the synthesis of the compounds of the present invention. For example, Scheme 6 illustrates methodology for conversion of a representative aniline into several quinoline intermediates.

SCHEME 6

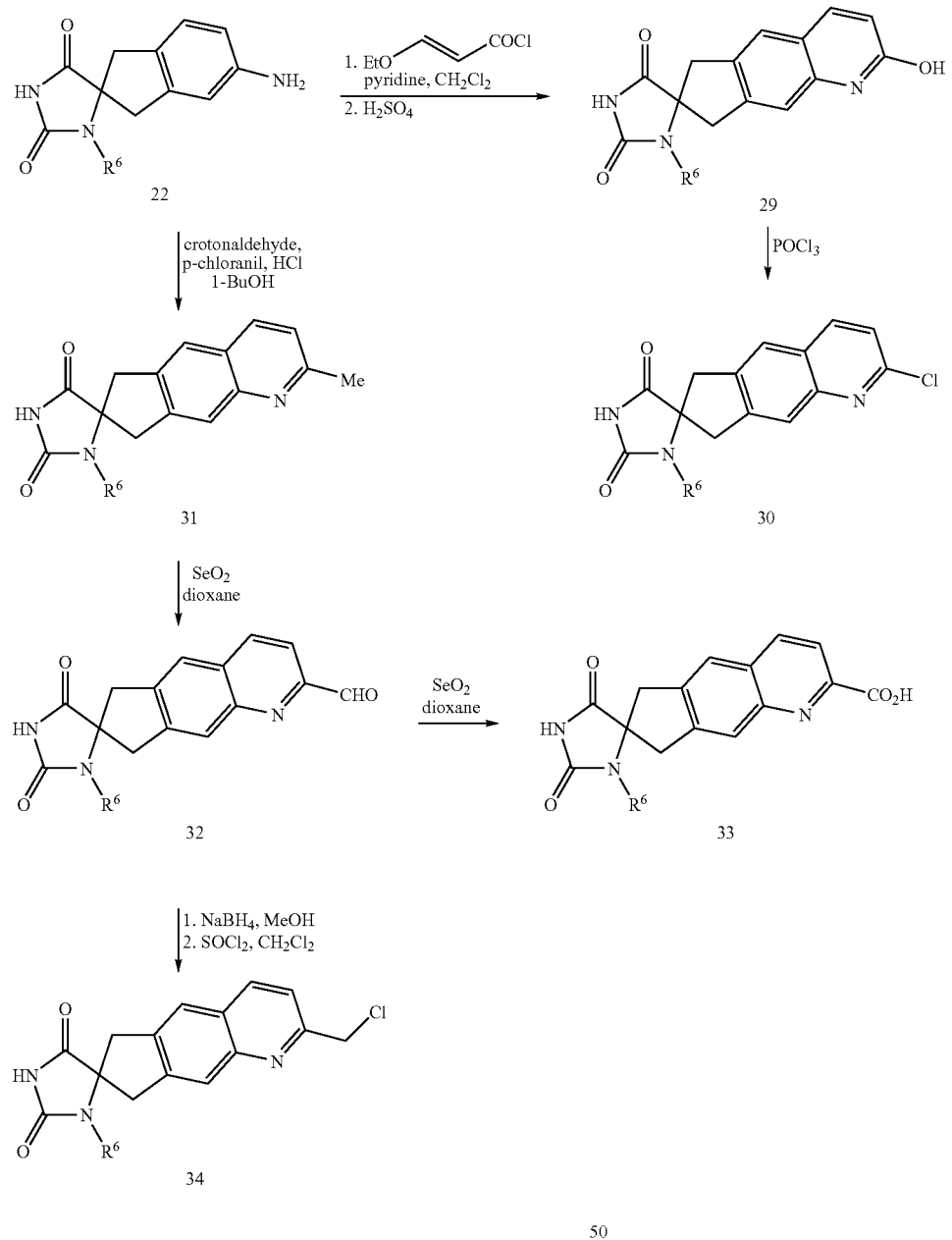

Aniline 22 may be acylated with (E)-3-ethoxyacryloyl chloride and treatment of the resulting amide with sulfuric acid leads to hydroxyquinoline 29, which can be converted to the corresponding chloride 30 by heating in phosphorus oxychloride. Condensation of aniline 24 with crotonaldehyde in the presence of acid and an oxidant affords the 2-methylquinoline 31. The use of other aldehydes under similar conditions can lead to alternatively substituted quinolines. Oxidation of quinoline 31 with selenium dioxide can provide either aldehyde 32 or carboxylic acid 33, depending on the amount of oxidant used and the duration of the reaction. Reduction of aldehyde 32 with sodium borohydride provides the corresponding alcohol, and treatment of this with thionyl chloride may be used to give the chloride 34. Intermediates such as 30, 32, 33 and 34 may be converted to compounds of the present invention using a variety of known methodology.

While the methodology shown in Scheme 6 is exemplified using aniline 22, it is understood that it may be applied to a variety of aniline substrates, such as those described herein, in order to provide various quinoline intermediates.

SCHEME 7

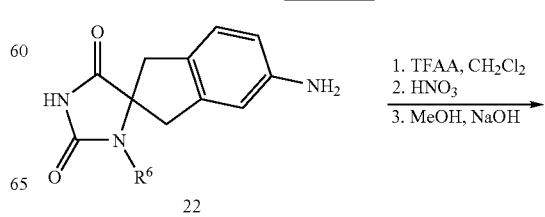

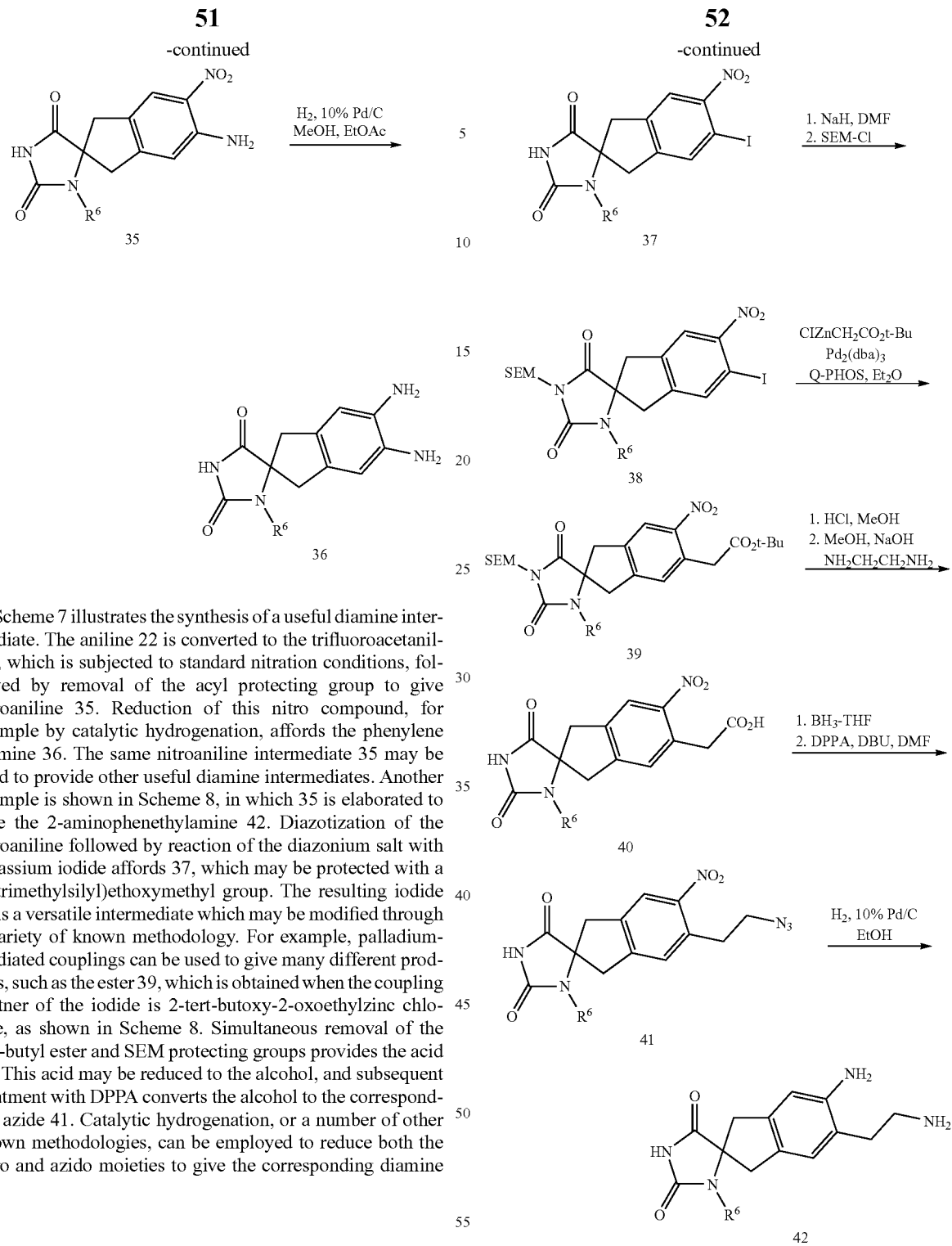

Scheme 7 illustrates the synthesis of a useful diamine intermediate. The aniline 22 is converted to the trifluoroacetanilide, which is subjected to standard nitration conditions, followed by removal of the acyl protecting group to give nitroaniline 35. Reduction of this nitro compound, for example by catalytic hydrogenation, affords the phenylene diamine 36. The same nitroaniline intermediate 35 may be used to provide other useful diamine intermediates. Another example is shown in Scheme 8, in which 35 is elaborated to give the 2-aminophenethylamine 42. Diazotization of the nitroaniline followed by reaction of the diazonium salt with potassium iodide affords 37, which may be protected with a 2-(trimethylsilyl)ethoxymethyl group. The resulting iodide 38 is a versatile intermediate which may be modified through a variety of known methodology. For example, palladium-mediated couplings can be used to give many different products, such as the ester 39, which is obtained when the coupling partner of the iodide is 2-tert-butoxy-2-oxoethylzinc chloride, as shown in Scheme 8. Simultaneous removal of the tert-butyl ester and SEM protecting groups provides the acid 40. This acid may be reduced to the alcohol, and subsequent treatment with DPPA converts the alcohol to the corresponding azide 41. Catalytic hydrogenation, or a number of other known methodologies, can be employed to reduce both the nitro and azido moieties to give the corresponding diamine 42.

SCHEME 8

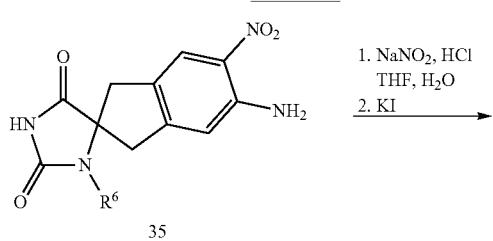

The methodology illustrated in the foregoing Schemes 6-8 describes the synthesis of some intermediates that are useful for making the compounds of the present invention. While the examples shown involve analogues of aniline 22, those skilled in the art will appreciate that such methodology may be extended to a variety of other anilines to give other useful intermediates. For example, Scheme 9 illustrates the synthesis of heterocyclic intermediates that are analogous to those in Scheme 6 but of a more general structure.

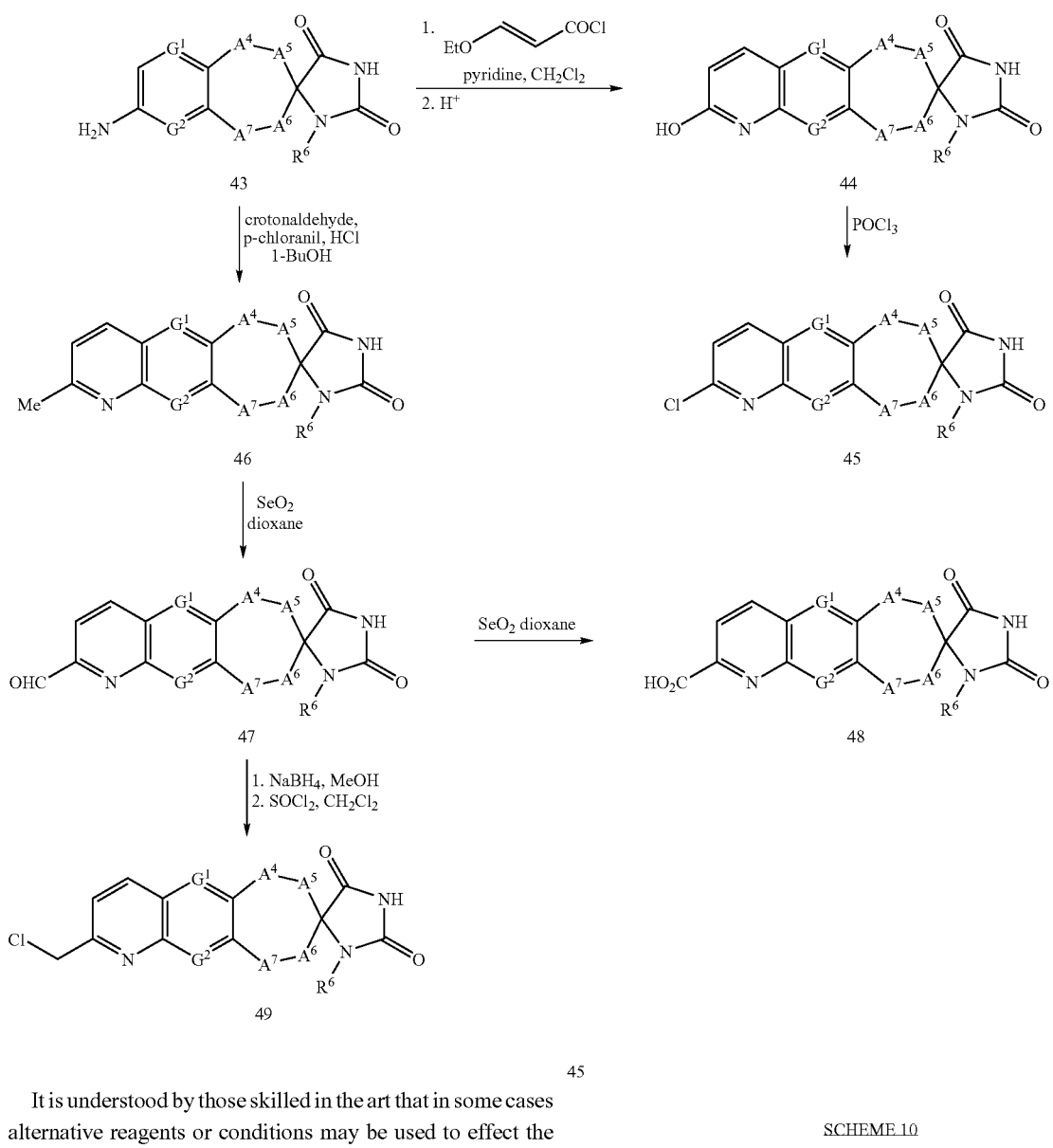

It is understood by those skilled in the art that in some cases alternative reagents or conditions may be used to effect the transformations in Scheme 9. In some cases, additional chemical steps may be required to obtain the compounds of interest, or various protecting group strategies may be employed.

The intermediates described in Schemes 6-9 may be used to synthesize the compounds of the present invention using a variety of known methodologies. Some of these methodologies are illustrated in Scheme 10. Standard reductive amination of an aldehyde like 47 with a suitable amine (RR'NH) may be used to obtain a final product of interest 50. Similarly, a standard coupling reaction may be used to convert carboxylic acid 48 to amide 51, which may be another example of the present invention when R and R' are selected appropriately.

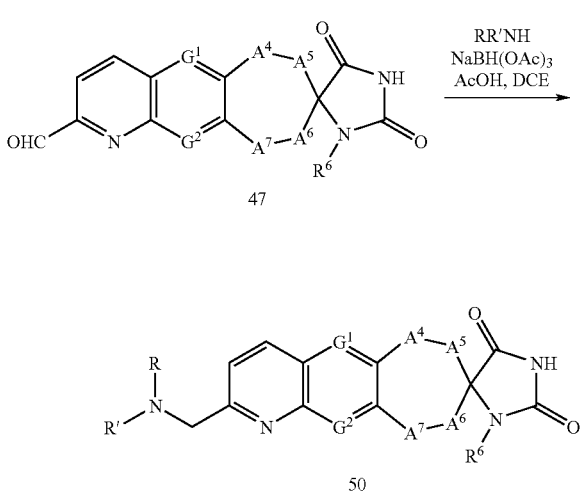

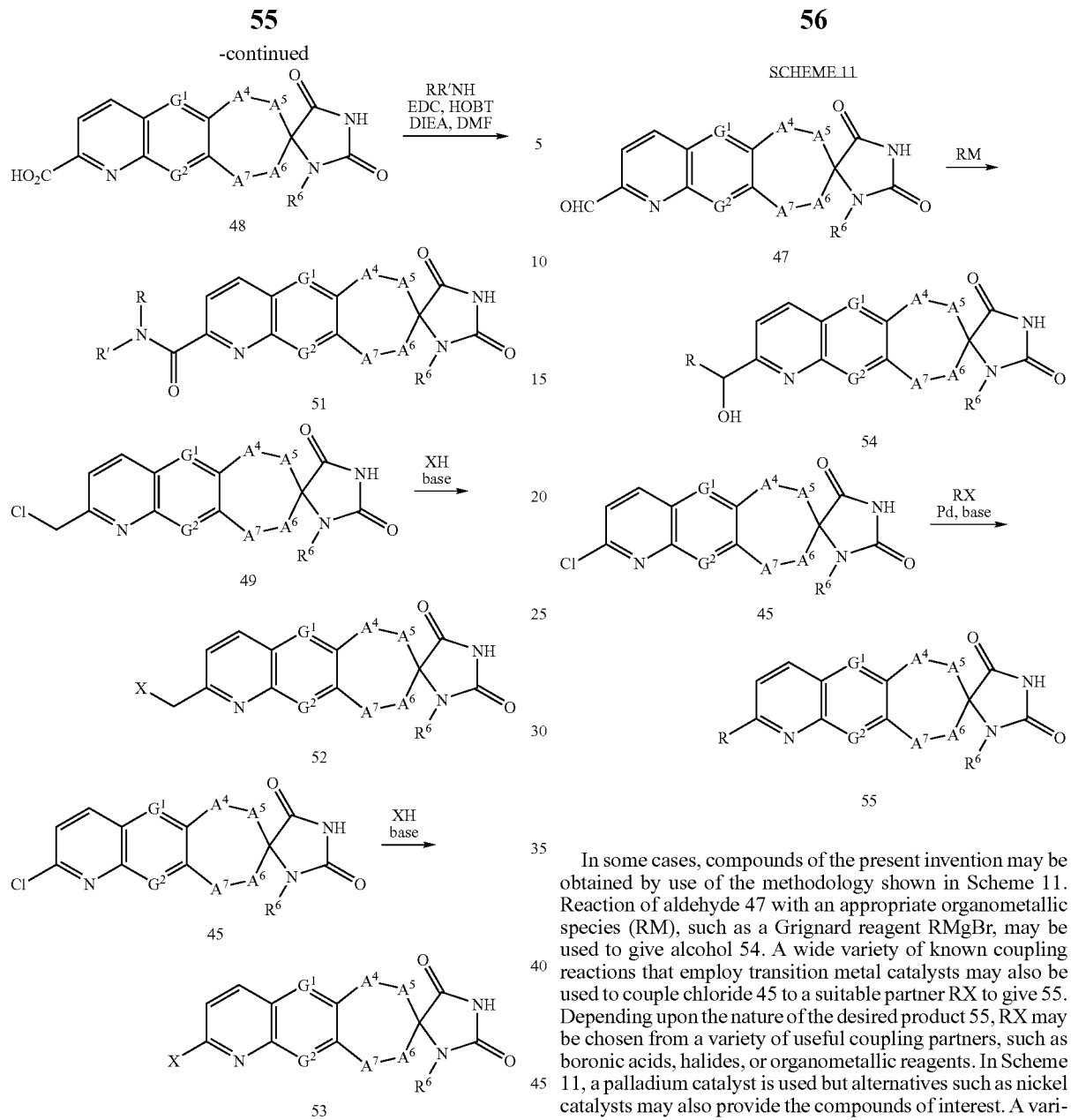

Scheme 10 also illustrates the coupling of chlorides 45 and 49 with a suitable partner (XH), usually under basic conditions, to give other compounds of the present invention (52 and 53). The precise nature of RR'NH or XH not only determines the identity of the final compound of interest, but also influences the choice of conditions under which the reaction is performed. For example, reductive amination of 47 may be performed using alternative conditions to those shown in Scheme 10, such as sodium cyanoborohydride in MeOH, depending on the exact natures of 47 and the amine. Similarly, the coupling of RR'NH and acid 48 may be carried out under a variety of known conditions, such as use of an alternative coupling reagent like PyBOP, or activation of the carboxylic acid as an acid anhydride or acid chloride. One skilled in the art will infer from precedent in the chemical literature, and from those examples given herein, suitable conditions for reaction of either 45 or 49 with XH, which is usually an amine, lactam or similar compound.

In some cases, compounds of the present invention may be obtained by use of the methodology shown in Scheme 11. Reaction of aldehyde 47 with an appropriate organometallic species (RM), such as a Grignard reagent RMgBr, may be used to give alcohol 54. A wide variety of known coupling reactions that employ transition metal catalysts may also be used to couple chloride 45 to a suitable partner RX to give 55. Depending upon the nature of the desired product 55, RX may be chosen from a variety of useful coupling partners, such as boronic acids, halides, or organometallic reagents. In Scheme 11, a palladium catalyst is used but alternatives such as nickel catalysts may also provide the compounds of interest. A variety of ligands may be utilized with such metal catalysts, as described in the literature.

Scheme 12 demonstrates how some other heterocyclic structures may be obtained from diamine precursors. The phenylenediamine 56 can be coupled to an acid $RCO_2H$ using well known coupling reagents, such as BOP, to give an anilide intermediate which may be cyclized in situ under acidic conditions to give the benzimidazole 57. The same starting material 56 can be condensed with a suitable ketoaldehyde, as shown in Scheme 12, to give the quinoxaline product 58. The required ketoaldehyde may be synthesized using known methodology. It may be a derivative of one of the coupling partners described herein, or subsequent functionalization after quinoxaline formation may be required to provide the desired compound of the present invention. Other ring sizes may also be obtained. For example, diamine 59 reacts readily with a variety of imidate esters to afford dihydrobenzodiazepine products of structure 60. The requisite imidate ester intermediate may be obtained using known methodology, such as treatment of the corresponding nitrile with an alcohol under acidic conditions.

SCHEME 12

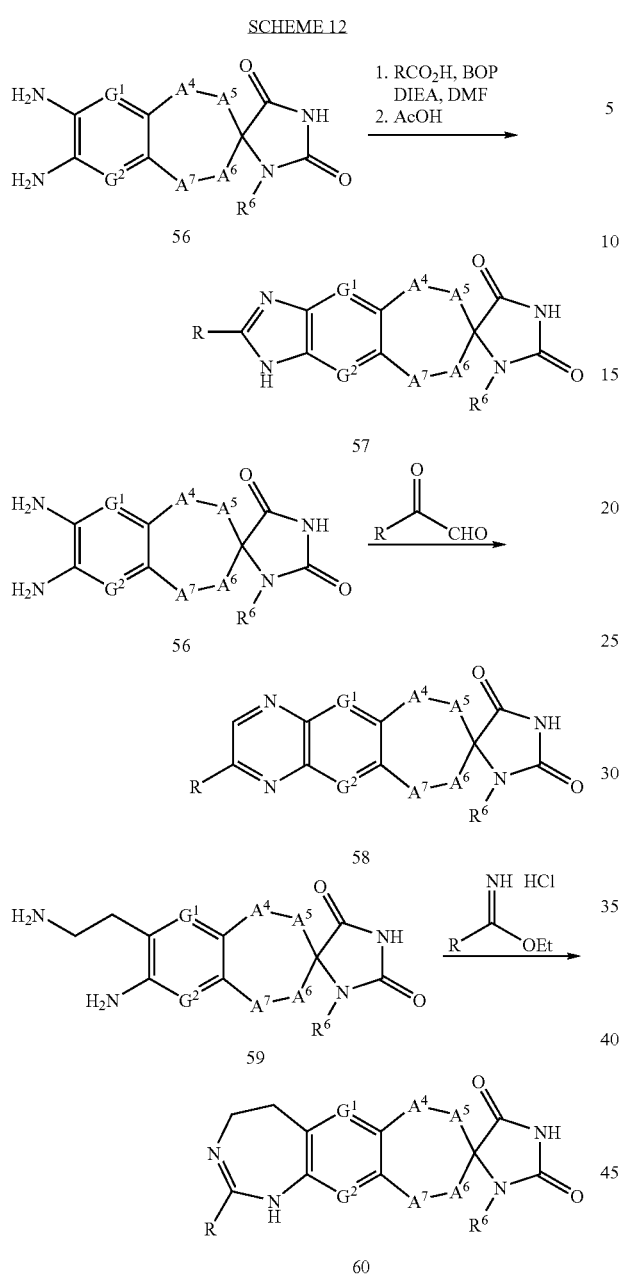

In Schemes 10-12, a number of strategies for assembling the compounds of the present invention are illustrated. It is understood that alternative methodologies may also be employed in the synthesis of compounds of interest. The exact choice of reagents, solvents, temperatures, and other reaction conditions, depends upon the nature of the intended product. In some cases, appropriate protecting group strategies may be used. In other cases, further elaboration of the product shown in Schemes 10-12 may be required to obtain the compound of the present invention. As previously stated, the identity of the coupling partner (e.g. RR'NH, XH, or RCO$_2$H) in Schemes 10-12 must be chosen appropriately to give the compounds of the present invention. Some representative examples of the synthesis of such coupling partners are shown in the following schemes. In many of the following schemes, the synthesis of a bicyclic intermediate is shown (for example, 101 in Scheme 13) and this may be used directly in couplings that lead to compounds of interest, such as those illustrated in Scheme 10. Many of the following schemes also show the further elaboration of such bicyclic intermediates to give other useful intermediates (for example, 103 in Scheme 13) that may lead to compounds of the present invention, such as those illustrated in Scheme 12.

In Scheme 13, carbonylation of a 2-aminophenol 100 with 1,1'-carbonyldiimidazole affords the benzoxazolone 101, which can be treated with sodium hydride, then tert-butyl bromoacetate, to provide ester 102. Standard deprotection using trifluoroacetic acid affords the acid intermediate 103.

SCHEME 13

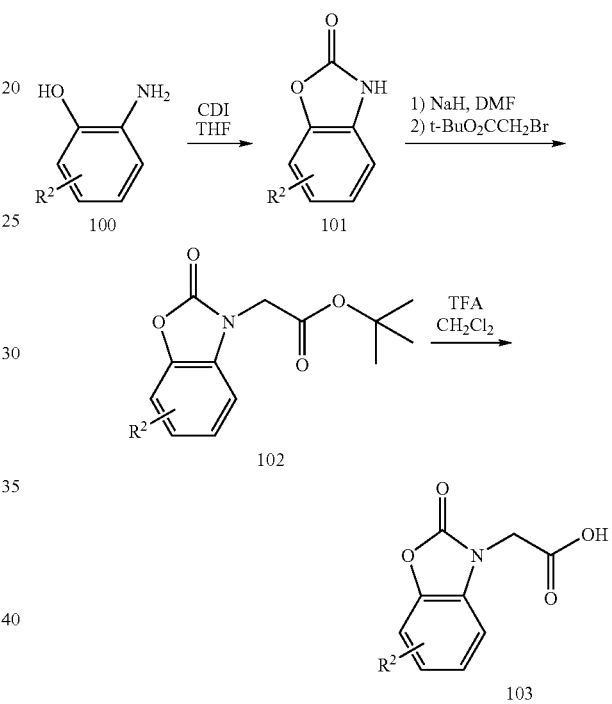

Scheme 14 illustrates a general route to substituted benzimidazolone derivatives. Simple alkylation of the benzimidazolone 104 affords the acetate derivative 105, which may be separated from any bis-alkylated material by chromatography. For a variety of aryl or heteroaryl R$^1$, reaction of the corresponding bromide (R$^1$Br) with 105 using copper catalysis provides the N,N-disubstituted intermediate 106. The tert-butyl ester 106 may be deprotected under acidic conditions to give 107, which is readily converted to the final products.

SCHEME 14

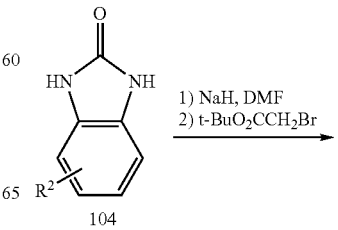

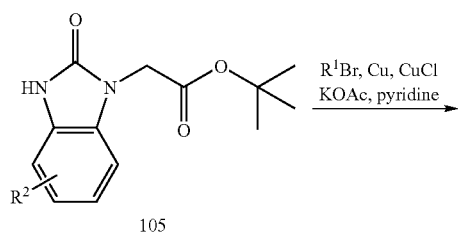

105

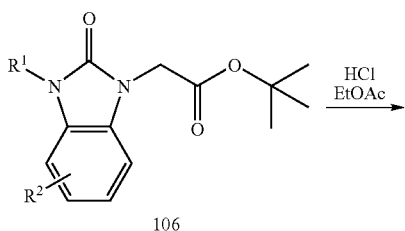

106

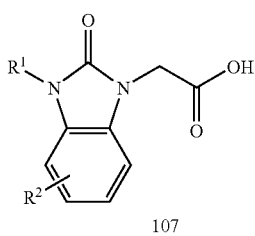

107

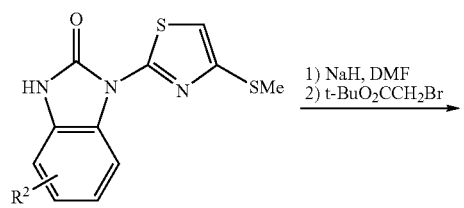

109

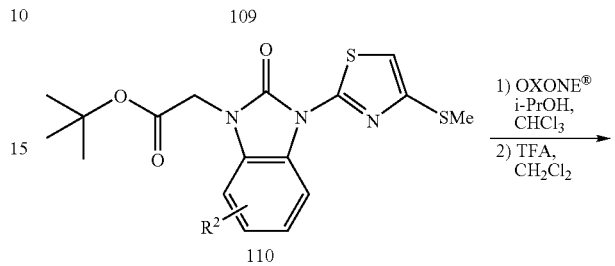

110

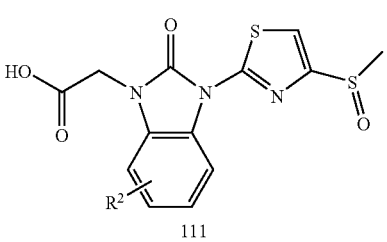

111

The chemistry in Scheme 14 may be modified in a number of ways. For example, use of alternative conditions for the key transformation of 105 to 106 can permit a variety of $R^1$ substituents to be introduced. Examples of such alternative conditions include a palladium-catalyzed coupling with 105, or an alkylation or arylation of the anion of 105 under basic conditions, for example using sodium hydride followed by $R^1Cl$. Further chemical manipulation of the substituents $R^1$ and $R^2$ is also understood to be within the scope of this invention. Either $R^1$ or $R^2$ may be modified under a variety of conditions at one or more intermediate steps in the synthetic sequence to afford a diverse group of final products. An example of this strategy is shown in Scheme 15.

In Scheme 15, benzimidazolone 104 is reacted with 2,4-dibromothiazole to give bromothiazole 108. Displacement of the bromide in 108 with thiomethoxide affords intermediate 109, which may be alkylated to give ester 110 in analogy with other schemes shown herein. Subjection of 110 to oxidative conditions, such as use of OXONE®, can provide the corresponding sulfoxide, which may be deprotected to give acid 111. Slight modifications of these conditions could be applied to afford the corresponding sulfide or sulfoxide analogues.

SCHEME 15

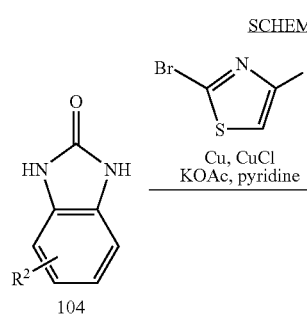

SCHEME 16

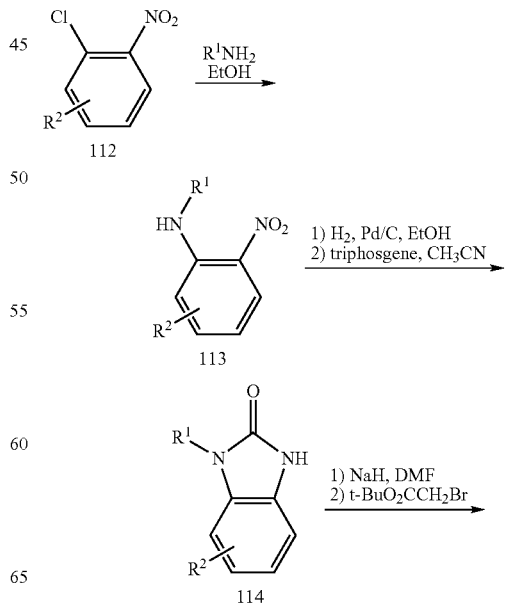

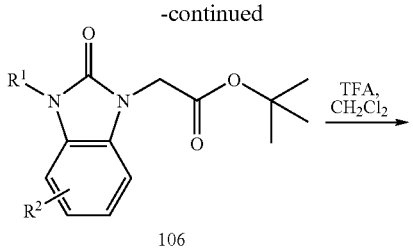

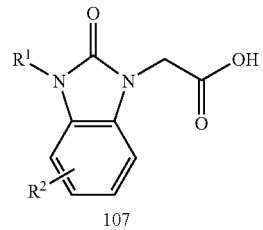

In Scheme 16, another route to the substituted benzimidazolone 107 is shown. In this route, an amine ($R^1NH_2$) is condensed with a 2-chloronitroarene derivative 112 to give amine 113. The nitro group may be reduced, for example under catalytic hydrogenation conditions, to give the corresponding aniline, and this may be treated with triphosgene to afford the benzimidazolone 114. Elaboration of 114 in analogy with the earlier Schemes leads to the desired acid intermediate 107. In a simple variation of this methodology, the arene 112 may be replaced with a heterocycle, such as 2-chloro-3-nitropyridine to afford an aza analogue of 107.

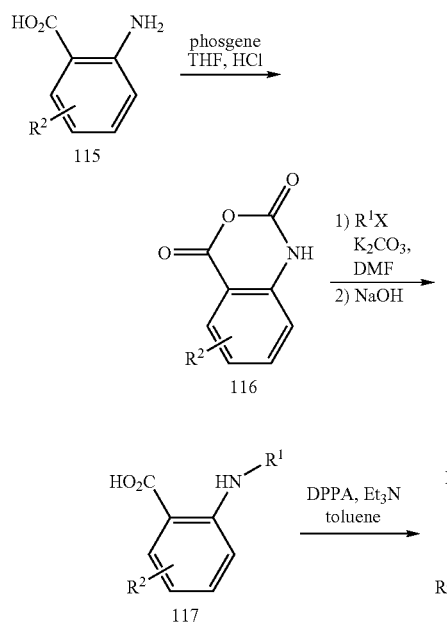

In Scheme 17, a route to regiospecifically-substituted benzimidazolone intermediate 114 from the corresponding anthranilic acid is shown. Treatment of the anthranilic acid 115 with phosgene can lead to the benzoxazinedione 116. Alkylation of 116 with a suitable bromoacetate, followed by opening of the benzoxazinedione ring with NaOH, provides the alkylated anthranilic acid 117. Treatment of acid 117 with diphenylphosphoryl azide leads to a Curtius rearrangement in which the intermediate isocyanate is trapped to give the benzimidazolone 114. This route offers a method of installing the $R^2$ substituent(s) in positions dictated by the substitution pattern of the anthranilic acid starting material.

SCHEME 18

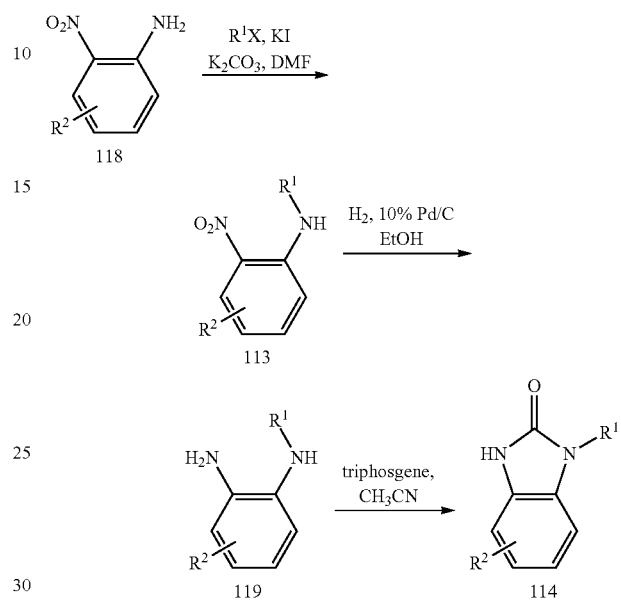

In Scheme 18, another method of constructing a regiospecifically-substituted benzimidazolone intermediate 114 is shown. Treatment of the nitroaniline 118 with a suitable alkylating agent under standard alkylation conditions can provide 113. This intermediate (previously described in Scheme 16) may be elaborated to give the benzimidazolone 114 in analogy with other schemes.

SCHEME 19

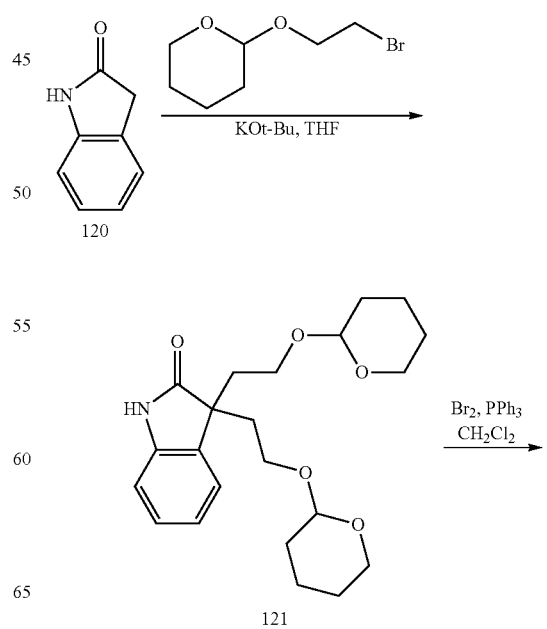

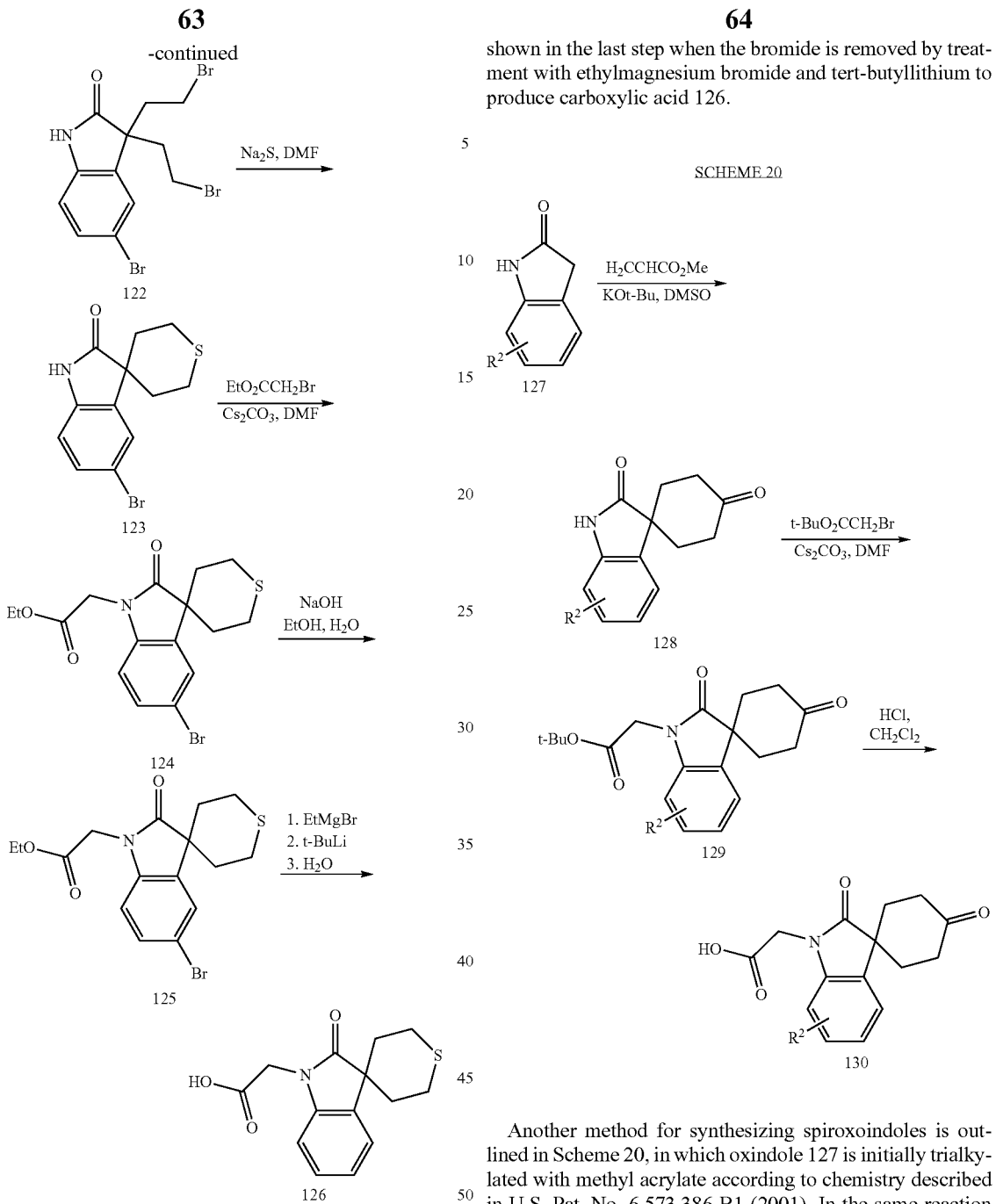

shown in the last step when the bromide is removed by treatment with ethylmagnesium bromide and tert-butyllithium to produce carboxylic acid 126.

A synthesis of N-spirooxindole acetic acids is outlined in Scheme 19. Following chemistry described in U.S. Pat. No. 5,849,780 A (1998), an example of such begins with the alkylation of oxindole 120 with a halide or its equivalent, e.g. 2-(2-bromoethoxy)tetrahydro-2H-pyran, and a base, such as potassium tert-butoxide or butyllithium, to yield intermediate 121. Treatment with bromine produces the tribromide 122, which when reacted with sodium sulfide can give the spirooxindole 123. Alternatively, 120 could be alkylated with a dihalide or other bis-alkylating agent, e.g. 2-iodoethyl ether, to produce a spirooxindole directly. Alkylation of oxindole 123 with ethyl bromoacetate followed by hydrolysis affords the desired acid intermediate 125. Further chemical manipulation of substituents on the aryl ring is understood to be within the scope of this invention. An example of this strategy is shown in the last step when the bromide is removed by treatment with ethylmagnesium bromide and tert-butyllithium to produce carboxylic acid 126.

Another method for synthesizing spiroxoindoles is outlined in Scheme 20, in which oxindole 127 is initially trialkylated with methyl acrylate according to chemistry described in U.S. Pat. No. 6,573,386 B1 (2001). In the same reaction flask, the intermediate then undergoes a Dieckmann condensation, N-dealkylation, and decarboxylation to produce spirocyclohexanone 128. Further manipulation as described in previous schemes may be used to produce carboxylic acid intermediates like 130.

SCHEME 21

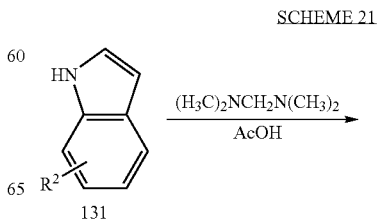

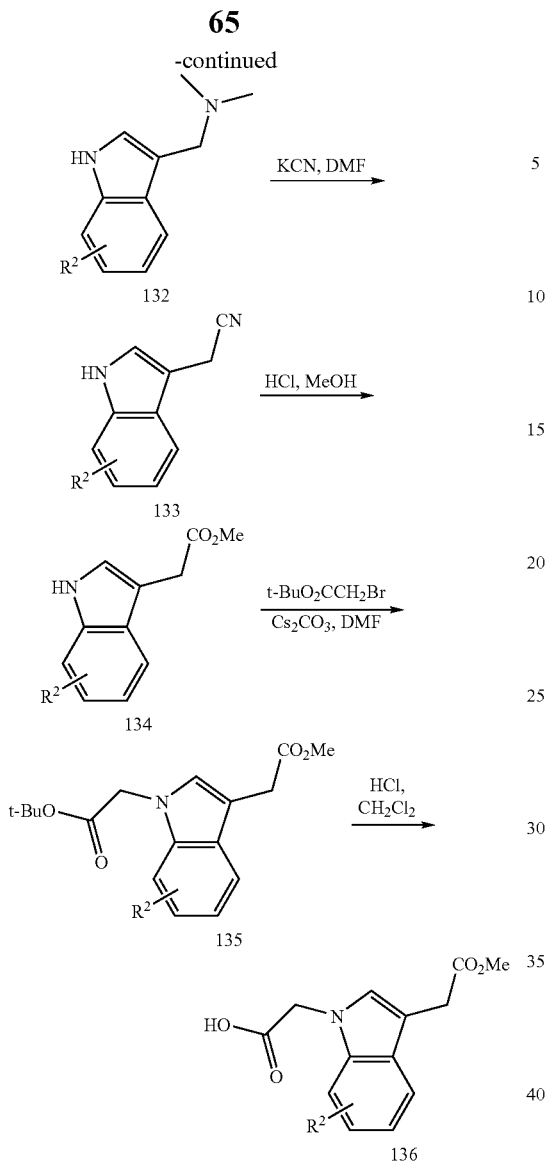

Scheme 21 illustrates a general route to substituted indole acetic acids. Substituted indoles 131 can be converted to indole acetonitriles 133 via a two step sequence: alkylation with N,N,N',N'-tetramethylmethanediamine followed by displacement with potassium cyanide. Alternatively, the first intermediate 132 can be formed by reaction of indole 131 with dimethylamine and formaldehyde in a microwave reactor. Treatment with hydrochloric acid in methanol can convert the nitrile to the methyl ester 134. Further manipulation in analogy with previous schemes can produce carboxylic acid intermediates like 136. Azaindole acetic acids may also be synthesized via a similar scheme starting with an appropriately substituted azaindole.

Simple modifications of these routes, including different protecting group strategies, application of well-precedented methodology, and the use of starting materials and reagents other than those described in the foregoing schemes, may be used to provide other acids of interest.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

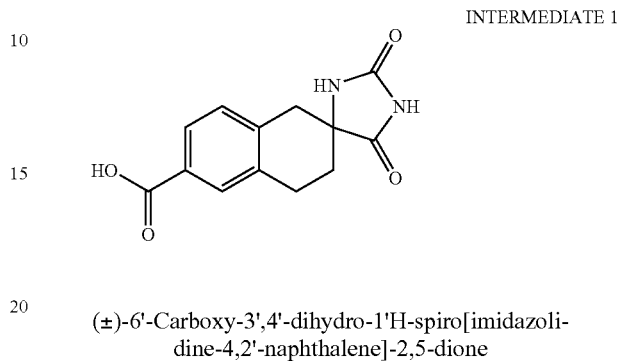

(±)-6'-Carboxy-3',4'-dihydro-1'H-spiro[imidazolidine-4,2'-naphthalene]-2,5-dione Step A. (±)-6'-Bromo-3',4'-dihydro-1'H-spiro[imidazolidine-4,2'-naphthalene]-2,5-dione A stirred mixture of 6-bromo-2-tetralone (17.6 g, 78.2 mmol), sodium cyanide (9.58 g, 195 mmol), and ammonium carbonate (97.7 g, 1.02 mol) in H2O (100 mL) and EtOH (100 mL) was heated to 70° C. for 3 h, then allowed to cool to ambient temperature. The precipitate was collected by filtration and washed with $H_2O$ (5×200 mL). Drying in vacuo afforded the title compound. MS: m/z=297 (M+1).

Step B. (±)-6'-Carboxy-3',4'-dihydro-1'H-spiro[imidazolidine-4,2'-naphthalene]-2,5-dione To a stirred suspension of (±)-6'-bromo-3',4'-dihydro-1'H-spiro[imidazolidine-4,2'-naphthalene]-2,5-dione (14.9 g, 50.5 mmol) in THF (1.2 L), at −70° C., was added dropwise ethyl magnesium bromide (3.0 M in THF, 51 mL, 152 mmol). The resulting mixture was stirred for 10 min, then tert-butyllithium (1.7 M in pentane, 180 mL, 305 mmol) was added dropwise over 30 min. Stirring was continued at −70° C. for 20 min, then additional tert-butyllithium (1.7 M in pentane, 60 mL, 102 mmol) was added dropwise over 10 min. After a further 30 min, $CO_2$ (g) was bubbled into the reaction mixture until LCMS analysis indicated complete reaction. The mixture was allowed to warm slowly to ambient temperature and the THF was removed in vacuo. The residue was suspended in $H_2O$ and the solution was adjusted to pH=1-2 by the addition of conc. hydrochloric acid, to a final volume of about 500 mL. The mixture was filtered and the isolated solid was washed with $H_2O$ (4×100 mL) then dried in vacuo. Trituration of this crude solid with EtOH provided the title compound. MS: m/z=261 (M+1).

INTERMEDIATE 2

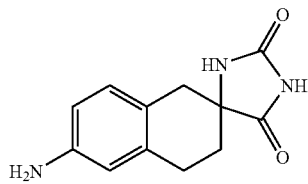

(±)-6'-Amino-3',4'-dihydro-1'H-spiro[imidazolidine-4,2'-naphthalene]-2,5-dione

Step A. (±)-6'-Amino-3',4'-dihydro-1'H-spiro[imidazolidine-4,2'-naphthalene]-2,5-dione A stirred mixture of (±)-6'-carboxy-3',4'-dihydro-1'H-spiro[imidazolidine-4,2'-naphthalene]-2,5-dione (described in Intermediate 1) (1.50 g, 5.76 mmol), and sodium azide (749 mg, 11.53 mmol) in conc. $H_2SO_4$ (30 mL) was heated to 50° C. for 2 h, then allowed to cool to ambient temperature. The mixture was adjusted to pH 8 by addition of 6 N aqueous NaOH and concentrated in vacuo to precipitate a solid. The precipitate was collected by filtration and washed extensively with $H_2O$. Drying in vacuo afforded the title compound. MS: m/z=232 (M+1).

INTERMEDIATE 3

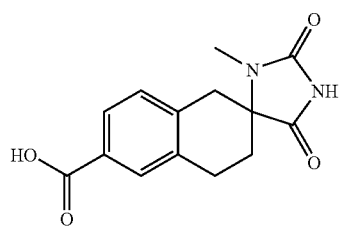

(±)-6'-Carboxy-3-methyl-3',4'-dihydro-1'H-spiro[imidazolidine-4,2'-naphthalene]-2,5-dione

Step A (±)-6'-Bromo-3-methyl-3',4'-dihydro-1'H-spiro[imidazolidine-4,2'-naphthalene]-2,5-dione A mixture of 6-bromo-2-tetralone (1.00 g, 4.44 mmol) and methylamine hydrochloride (300 mg, 4.44 mol) in $H_2O$ (1 mL) and EtOH (1.5 mL) was stirred at ambient temperature for 20 min. Potassium cyanide (289 mg, 4.44 mmol) was added and stirring was continued for 18 h. The mixture was added dropwise to a stirred solution of 1.0 N aqueous HCl (4.5 mL) at 0° C., then potassium cyanate (360 mg, 4.44 mmol) was added portionwise. The stirred mixture was heated to 95° C. and conc. hydrochloric acid (0.44 mL) was added dropwise. The reaction mixture was heated at this temperature for 1 h, allowed to cool, and extracted with $CH_2Cl_2$ (80 mL). The organic extract was dried over $Na_2SO_4$, filtered, and concentrated to dryness. The crude product was purified by silica gel chromatography, eluting with a gradient of $CH_2Cl_2$:MeOH—100:0 to 90:10, to provide a crude sample of the title compound (ca. 70% pure). Trituration with EtOH afforded the title compound. MS: m/z=311 (M+1).

Step B. (±)-6'-Carboxy-3-methyl-3',4'-dihydro-1'H-spiro[imidazolidine-4,2'-naphthalene]-2,5-dione To a stirred suspension of (±)-6'-bromo-3-methyl-3',4'-dihydro-1'H-spiro[imidazolidine-4,2'-naphthalene]-2,5-dione (211 mg, 0.682 mmol) in THF (30 mL), at −70° C., was added dropwise ethyl magnesium bromide (1.0 M in THF, 1.37 mL, 1.37 mmol). The resulting mixture was stirred for 15 min, then tert-butyllithium (1.7 M in pentane, 1.61 mL, 2.73 mmol) was added dropwise. After a further 30 min, $CO_2$ (g) was bubbled into the reaction mixture until LCMS analysis indicated complete reaction. The mixture was allowed to warm slowly to ambient temperature and the THF was removed in vacuo. The residue was suspended in $H_2O$ (20 mL) and the solution was adjusted to pH=1-2 by the addition of 1.0 N hydrochloric acid, then it was saturated with NaCl (s). The mixture was filtered and the isolated solid was washed with $H_2O$ then dried in vacuo. Trituration of this crude solid with EtOH provided the title compound. MS: m/z=275 (M+1).

INTERMEDIATE 4

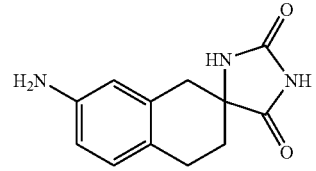

(±)-7'-Amino-3',4'-dihydro-1'H-spiro[imidazolidine-4,2'-naphthalene]-2,5-dione

Step A 7-Bromo-2-tetralone

A solution of 3-bromophenylacetic acid (10.4 g, 48.4 mmol) in oxalyl chloride (50 mL, 0.57 mol) was stirred at ambient temperature for 5 min then at reflux for 5 h. The oxalyl chloride was removed in vacuo and the residue was dissolved in anhydrous $CH_2Cl_2$ (100 mL). This solution was added dropwise to a rapidly stirred, ice-cooled solution of $AlCl_3$ (23.2 g, 174.2 mmol) in $CH_2Cl_2$ (500 mL). A stream of ethylene gas was blown into the vortex of the stirred solution during the addition and the reaction temperature was kept at <5° C. The reaction mixture was allowed to warm to ambient temperature and then poured onto ice and stirred vigorously. The organic portion was removed and the aqueous layer extracted with $CH_2Cl_2$ (2×200 mL). The combined $CH_2Cl_2$ fractions were passed through a 2" pad of silica and concentrated to give a thick, red oil. The crude product was purified by silica gel chromatography, eluting with a gradient of hexane:EtOAc—100:0 to 75:25, to provide the title compound. MS: m/z=226 (M+1).

(±)-7'-Amino-3',4'-dihydro-1'H-spiro[imidazolidine-4,2'-naphthalene]-2,5-dione Essentially following the procedures described for Intermediate 1 and Intermediate 2, but using 7-bromo-2-tetralone in place of 6-bromo-2-tetralone, (±)-7'-amino-3',4'-dihydro-1'H-spiro[imidazolidine-4,2'-naphthalene]-2,5-dione was prepared. MS: m/z=232 (M+1).

INTERMEDIATE 5

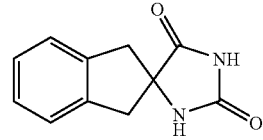

(±)-Spiro[imidazolidine-4,2'-indane]-2,5-dione

Step A. (±)-Spiro[imidazolidine-4,2'-indane]-2,5-dione

A stirred mixture of 2-indanone (3.0 g, 22.6 mmol), sodium cyanide (3.3 g, 67.3 mmol), and ammonium carbonate (22 g, 228 mol) in H$_2$O (50 mL) and EtOH (50 mL) was heated to 70° C. for 3 h, then allowed to cool to ambient temperature. The precipitate was collected by filtration and washed with H$_2$O (5×100 mL). Drying in vacuo afforded the title compound. MS: m/z=202 (M+1).

INTERMEDIATE 6

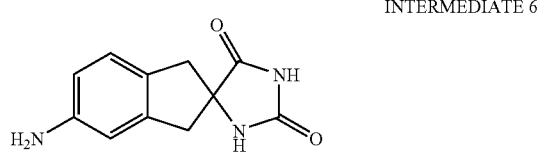

(±)-5'-Amino-spiro[imidazolidine-4,2'-indane]-2,5-dione

Step A. (±)-5'-Nitro-spiro[imidazolidine-4,2'-indane]-2,5-dione

A solution of (±)-spiro[imidazolidine-4,2'-indane]-2,5-dione (3.0 g, 14.8 mmol, described in Intermediate 5) in conc. nitric acid (33 mL) was stirred at ambient temperature for 1 h. The reaction was then poured onto crushed ice and the resultant solid was isolated by filtration. The crude material was recrystallized from ethanol to give the title compound. MS: m/z=248 (M+1).

Step B. (±)-5'-Amino-spiro[imidazolidine-4,2'-indane]-2,5-dione

To a suspension of (±)-5'-nitro-spiro[imidazolidine-4,2'-indane]-2,5-dione (1.77 g, 7.16 mmol) in EtOAc (100 mL) and MeOH (100 mL) was added 10% Pd/C (400 mg) and the reaction stirred vigorously under hydrogen (ca. 1 atm). After 1 h, the catalyst was filtered off and the filtrate was concentrated to yield the title compound. MS: m/z=218 (M+1).

INTERMEDIATE 7

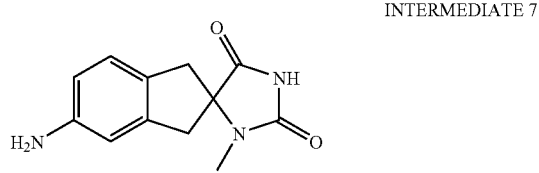

(±)-5'-Amino-3-methyl-spiro[imidazolidine-4,2'-indane]-2,5-dione

Step A. 2-(Methylamino)indane-2-carbonitrile hydrochloride

To a mixture of 2-indanone (20.0 g, 151 mmol) in MeOH (20 mL) was added methylamine hydrochloride (10.2 g, 151 mmol). To the stirred mixture was added H$_2$O (20 mL) and a fine homogenous slurry developed. The reaction mixture was cooled to 0° C. and KCN (9.84 g, 151 mmol) in H$_2$O (20 mL) was added slowly over 30 min, such that the temperature did not exceed 10° C., then stirring was continued at ambient temperature for 18 h. The reaction mixture was extracted with Et$_2$O (250 mL) and the organic extract was washed with brine (50 mL) then dried over MgSO$_4$. HCl (g) was bubbled through the vigorously stirred solution for 10 minutes and a white solid precipitated. The solid was filtered, washed with Et$_2$O, and dried to yield the title compound. MS: m/z=173 (M+1).

Step B. (±)-3-Methyl-spiro[imidazolidine-4,2'-indane]-2,5-dione

To a stirred mixture of 2-(methylamino)indane-2-carbonitrile hydrochloride from Step A (6.0 g, 28.8 mmol) in AcOH (45 mL) was added a solution of potassium cyanate (4.65 g, 57 mmol) in H$_2$O (6 mL) and the reaction mixture was stirred for 1 h. The mixture was poured into cold H$_2$O (150 mL) and the precipitate was isolated by filtration, washed with H$_2$O and air dried. The crude solid was suspended in 1 N HCl (30 mL) and stirred to 50° C. for 2 h. The reaction mixture was cooled, filtered, and the isolated solid washed with H$_2$O and dried in vacuo to yield the title compound. MS: m/z=217 (M+1).

Step C. (±)-3-Methyl-5'-nitro-spiro[imidazolidine-4,2'-indane]-2,5-dione

To stirred fuming (90%) nitric acid (100 mL) was slowly added (±)-3-methyl-spiro[imidazolidine-4,2'-indane]-2,5-dione (4.5 g, 20.9 mmol) in portions over 30 min. The reaction mixture was diluted with H$_2$O (200 mL) and the precipitate was collected by filtration, washed with H$_2$O and dried in vacuo to give the title compound. MS: m/z=262 (M+1).

(±)-5'-Amino-3-methyl-spiro[imidazolidine-4,2'-indane]-2,5-dione

Essentially following the procedures described for Intermediate 6, but using (±)-3-methyl-5'-nitro-spiro[imidazolidine-4,2'-indane]-2,5-dione in place of (±)-5'-nitro-spiro[imidazolidine-4,2'-indane]-2,5-dione, the title compound was prepared. MS: m/z=232 (M+1).

INTERMEDIATE 8

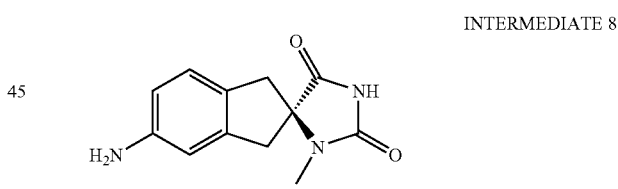

(R)-5'-Amino-3-methyl-spiro[imidazolidine-4,2'-indane]-2,5-dione

Step A. (R)-3-Methyl-5'-nitro-spiro[imidazolidine-4,2'-indane]-2,5-dione (±)-3-Methyl-5'-nitro-spiro[imidazolidine-4,2'-indane]-2,5-dione (described in Intermediate 7) was dissolved in a mixture of MeOH, CH$_3$CN and diethylamine and the enantiomers were resolved by HPLC, utilizing a Chiralpak AD column and eluting with CH$_3$CN:MeOH—90:10. The first major peak to elute was (S)-3-methyl-5'-nitro-spiro[imidazolidine-4,2'-indane]-2,5-dione and the second major peak to elute was (R)-3-methyl-5'-nitro-spiro[imidazolidine-4,2'-indane]-2,5-dione, the title compound. MS: m/z=262 (M+1).

(R)-5'-Amino-3-methyl-spiro[imidazolidine-4,2'-indane]-2,5-dione

Essentially following the procedures described for Intermediate 6, but using (R)-3-methyl-5'-nitro-spiro[imidazolidine-4,2'-indane]-2,5-dione in place of (±)-5'-nitro-spiro[imidazolidine-4,2'-indane]-2,5-dione, the title compound was prepared. MS: m/z=232 (M+1).

INTERMEDIATE 9

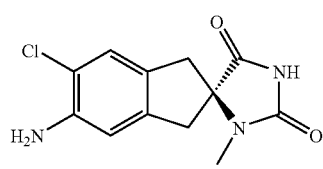

(S)-5'-Amino-6'-chloro-3-methyl-spiro[imidazolidine-4,2'-indane]-2,5-dione

Step A. (S)-5'-Amino-6'-chloro-3-methyl-spiro[imidazolidine-4,2'-indane]-2,5-dione (R)-5'-Amino-3-methyl-spiro[imidazolidine-4,2'-indane]-2,5-dione (265 mg, 1.15 mmol, described in Intermediate 8) was dissolved in AcOH (7 mL) and N-chlorosuccinimide (145 mg, 1.09 mmol) was added in one portion. The mixture was stirred at ambient temperature for 5 h, then the solvent was removed in vacuo. The residue was partitioned between saturated aqueous NaHCO₃ (20 mL) and CH₂Cl₂ (70 mL). The organic layer was dried (Na₂SO₄), filtered, and concentrated under reduced pressure. The crude product was purified by silica gel chromatography, eluting with a gradient of CH₂Cl₂:EtOAc—100:0 to 0:100, to give (R)-5'-amino-4'-chloro-3-methyl-spiro[imidazolidine-4,2'-indane]-2,5-dione, which eluted first, and the title compound, which eluted second. MS: m/z=266 (M+1).

INTERMEDIATE 10

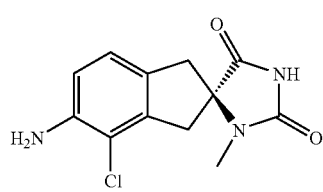

(R)-5'-Amino-4'-chloro-3-methyl-spiro[imidazolidine-4,2'-indane]-2,5-dione

Step A. (R)-5'-Amino-4'-chloro-3-methyl-spiro[imidazolidine-4,2'-indane]-2,5-dione The title compound was obtained from the same reaction as Intermediate 9. The crude product was purified by silica gel chromatography, eluting with a gradient of CH₂Cl₂:EtOAc—100:0 to 0:100, to give the title compound, which eluted first, and (s)-5'-amino-6'-chloro-3-methyl-spiro[imidazolidine-4,2'-indane]-2,5-dione, which eluted second. MS: m/z=266 (M+1).

INTERMEDIATE 11

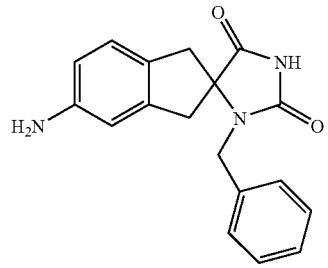

(±)-5'-Amino-3-(benzyl)-spiro[imidazolidine-4,2'-indane]-2,5-dione

Step A. (±)-1-(4-Methoxybenzyl)-5'-nitro-spiro[imidazolidine-4,2'-indane]-2,5-dione A mixture of (±)-5'-nitro-spiro[imidazolidine-4,2'-indane]-2,5-dione (1.4 g, 5.66 mmol, described in Intermediate 6), 4-methoxybenzyl alcohol (0.94 g, 6.80 mmol), diethyl azodicarboxylate (1.48 g, 8.49 mmol), and triphenylphosphine (2.23 g, 8.49 mmol) in THF (15 mL) was stirred at ambient temperature for 3 days. The solvent was removed under reduced pressure and the residue was partitioned between saturated aqueous NaHCO₃ (15 mL) and CH₂Cl₂ (50 mL). The organic layer was dried (Na₂SO₄), filtered, and concentrated under reduced pressure. The crude product was purified by silica gel chromatography, eluting with a gradient of hexane:EtOAc—90:10 to 60:40, to give the title compound. MS: m/z=368 (M+1).

Step B. (±)-3-Benzyl-1-(4-methoxybenzyl)-5'-nitro-spiro[imidazolidine-4,2'-indane]-2,5-dione To a solution of (±)-1-(4-methoxybenzyl)-5'-nitro-spiro[imidazolidine-4,2'-indane]-2,5-dione from Step A (165 mg, 0.45 mmol) in DMF (1 mL) was added sodium hydride (18 mg of a 60% dispersion in mineral oil, 0.45 mmol). The mixture was stirred for 5 min at ambient temperature and benzyl bromide (230 mg, 1.35 mmol) was added. After 30 min, the mixture was partitioned between saturated aqueous NaHCO₃ (3 mL) and CHCl₃ (5 mL). The aqueous phase was extracted further with CHCl₃ (5 mL) and the combined organic layers were dried (Na₂SO₄), filtered, and concentrated under reduced pressure. The crude product was purified by silica gel chromatography, eluting with hexane:EtOAc—75:25, to give the title compound. MS: m/z=458 (M+1).

Step C. (±)-3-Benzyl-5'-nitro-spiro[imidazolidine-4,2'-indane]-2,5-dione

To a stirred solution of (±)-3-benzyl-1-(4-methoxybenzyl)-5'-nitro-spiro[imidazolidine-4,2'-indane]-2,5-dione from Step B (110 mg, 0.24 mmol) in acetonitrile (1.5 mL) was added dropwise a solution of ammonium cerium (IV) nitrate (395 mg, 0.72 mmol) in H₂O (1 mL). After 3 h at ambient temperature, the precipitate was isolated by filtration and dried in vacuo to afford the title compound. MS: m/z=338 (M+1).

Step D. (±)-5'-Amino-3-benzyl-spiro[imidazolidine-4,2'-indane]-2,5-dione

To a solution of (±)-3-benzyl-5'-nitro-spiro[imidazolidine-4,2'-indane]-2,5-dione from Step C (80 mg, 0.24 mmol) in EtOAc (1.5 mL) and MeOH (1.5 mL) was added 10% Pd/C (5 mg) and the reaction mixture was stirred vigorously under hydrogen (ca. 1 atm). After 18 h, the catalyst was filtered off and the filtrate was concentrated to yield the title compound. MS: m/z=308 (M+1).

INTERMEDIATE 12

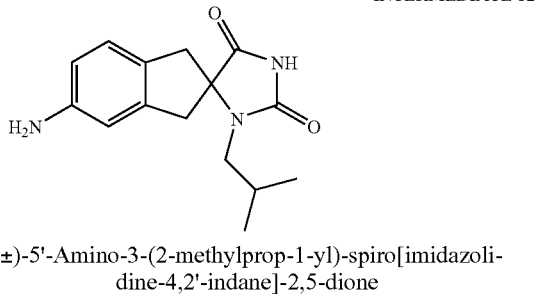

(±)-5'-Amino-3-(2-methylprop-1-yl)-spiro[imidazolidine-4,2'-indane]-2,5-dione

Essentially following the procedures described for Intermediate 11, but using 1-bromo-2-methylpropane in place of benzyl bromide, the title compound was prepared. MS: m/z=274 (M+1).

INTERMEDIATE 13

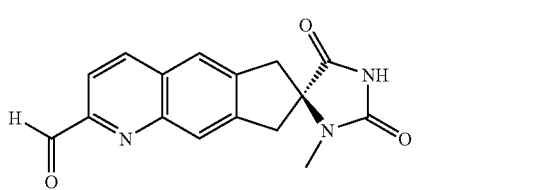

(7R)-3'-Methyl-2',5'-dioxo-6,8-dihydrospiro[cyclopenta[g]quinoline-7,4'-imidazolidine]-2-carbaldehyde Step A. (7R)-2,3'-Dimethyl-6,8-dihydro-2'H,5'H-spiro[cyclopenta[g]quinoline-74'-imidazolidine]-2',5'-dione (R)-5'-Amino-3-methyl-spiro[imidazolidine-4,2'-indane]-2,5-dione (3.00 g, 13.0 mmol, described in Intermediate 8) and p-chloranil (3.19 g, 13.0 mmol) were suspended in a mixture of 1-BuOH (3.2 mL) and conc. hydrochloric acid (3.2 mL, 39 mmol) and the mixture was heated to reflux. Crotonaldehyde (1.09 g, 15.6 mmol) in 1-BuOH (3 mL) was added dropwise over 20 min. After a further 20 min at reflux, the mixture was allowed to cool to ambient temperature and 10 N NaOH (3.9 mL, 39 mmol) was added and the neutralized mixture was concentrated in vacuo to give a brown residue. The crude product was purified by silica gel chromatography, eluting with a gradient of CH$_2$Cl$_2$:MeOH—100:0 to 90:10, to give the title compound. MS: m/z=282 (M+1).

Step B. (7R)-3'-Methyl-2',5'-dioxo-6,8-dihydrospiro [cyclopenta[g]quinoline-7,4'-imidazolidine]-2-carbaldehyde A mixture of (7R)-2,3'-dimethyl-6,8-dihydro-2'H,5'H-spiro[cyclopenta[g]quinoline-7,4'-imidazolidine]-2',5'-dione from Step A (1.70 g, 6.04 mmol), selenium dioxide (1.01 g, 9.06 mmol) and powdered molecular sieves, 4 Å, (680 mg) in dioxane (60 mL) was heated at reflux for 90 min. The reaction mixture was filtered through a pad of Celite, washing with CH$_2$Cl$_2$-MeOH, and the filtrate was concentrated under reduced pressure. The residue was partitioned between saturated aqueous NaHCO$_3$ (400 mL) and EtOAc (1.5 L) containing MeOH (30 mL). The organic layer was extracted and the aqueous layer was washed with EtOAc (400 mL). The combined organic layers were washed with brine, dried over Na$_2$SO$_4$, filtered, and concentrated in vacuo to give the title compound. MS: m/z=296 (M+1).

INTERMEDIATE 14

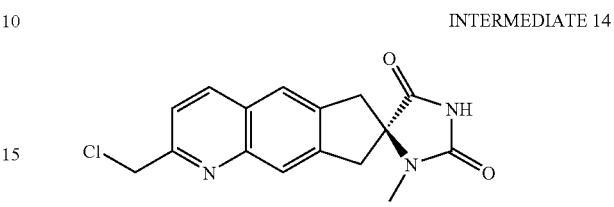

(7R)-2-(Chloromethyl)-3'-methyl-6,8-dihydro-2'H, 5'H-spiro[cyclopenta[g]quinoline-7,4'-imidazolidine]-2',5'-dione Step A. (7R)-2-(Hydroxymethyl)-3'-methyl-6,8-dihydro-2'H,5'H-spiro[cyclopenta[g]quinoline-7,4'-imidazolidine]-2',5'-dione To a stirred solution of (7R)-3'-methyl-2',5'-dioxo-6,8-dihydrospiro[cyclopenta[g]quinoline-7,4'-imidazolidine]-2-carbaldehyde (2.62 g, 8.89 mmol, described in Intermediate 13) in MeOH (20 mL) was added NaBH$_4$ (672 mg, 17.8 mmol) and the mixture was stirred at ambient temperature for 1 h, then concentrated to dryness in vacuo. The crude product was purified by silica gel chromatography, eluting with a gradient of CH$_2$Cl$_2$:MeOH:N$_4$OH—100:0:0 to 90:9:1, to give the title compound. MS: m/z=298 (M+1).

Step B. (7R)-2-(Chloromethyl)-3'-methyl-6,8-dihydro-2'H,5'H-spiro[cyclopenta[g]quinoline-7,4'-imidazolidine]-2',5'-dione To a stirred solution of (7R)-2-(hydroxymethyl)-3-methyl-6,8-dihydro-2'H,5'H-spiro[cyclopenta[g]quinoline-7,4'-imidazolidine]-2',5'-dione from Step A (200 mg, 0.67 mmol) in CH$_2$Cl$_2$ (5 mL) was added thionyl chloride (0.98 mL, 13.5 mmol) dropwise. The reaction mixture was stirred for 30 min and the precipitate was isolated by filtration. The filtrate was poured into saturated aqueous NaHCO$_3$ (20 mL) and this mixture was extracted with CH$_2$Cl$_2$ (3×30 mL). The combined organic extracts were dried over Na$_2$SO$_4$, filtered, and concentrated in vacuo to give a solid, which was combined with the filtered solid to give the title compound, which was of sufficient purity for use in subsequent steps. MS: m/z=316 (M+1).

INTERMEDIATE 15

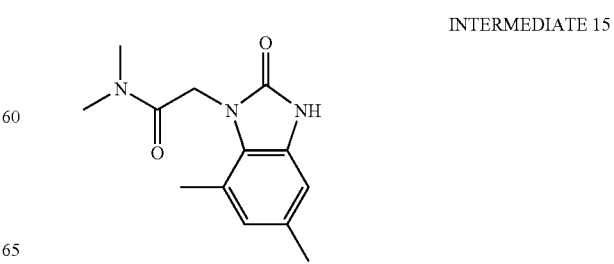

2-(5,7-Dimethyl-2-oxo-2,3-dihydro-1H-benzimidazol-1-yl)-N,N-dimethylacetamide

Step A. N²-(2,4-Dimethyl-6-nitrophenyl)-N¹,N¹-dimethyl glycinamide

A mixture of 2,4-dimethyl-6-nitroaniline (5.00 g, 30.1 mmol), 2-chloro-N,N-dimethylacetamide (18.3 g, 150 mmol), K₂CO₃ (6.24 g, 45.2 mmol), and KI (499 mg, 3.01 mmol) in DMF (100 mL) was heated at 120° C. for 7 h, then at 130° C. for 14 h. The cooled mixture was quenched with H₂O (200 mL) and extracted with CH₂Cl₂ (3×150 mL). The combined organic layers were dried over Na₂SO₄, filtered, and concentrated under reduced pressure. The crude product was purified by silica gel chromatography, eluting with a gradient of hexane:EtOAc—100:0 to 50:50, to give the title compound. MS: m/z=252 (M+1).

Step B. N²-(2-Amino-4,6-dimethylphenyl)-N¹,N¹-dimethylglycinamide

To a solution of N²-(2,4-dimethyl-6-nitrophenyl)-N¹,N¹-dimethylglycinamide from Step A (2.54 g, 10.1 mmol) in EtOH (50 mL) was added 10% Pd/C (500 mg). The reaction mixture was stirred under a hydrogen atmosphere (ca. 1 atm) for 72 h, then filtered through a Celite pad, washing with EtOH, and the filtrate was concentrated under reduced pressure. The crude product was purified by silica gel chromatography, eluting with a gradient of hexane:EtOAc—100:0 to 0:100, to give the title compound. MS: m/z=222 (M+1).

Step C. 2-(5,7-Dimethyl-2-oxo-2,3-dihydro-1H-benzimidazol-1-yl)-N,N-dimethylacetamide To a solution of N²-(2-amino-4,6-dimethylphenyl)-N¹,N¹-dimethylglycinamide from Step B (930 mg, 4.20 mmol) in CH₃CN (20 mL) at 0° C. was added triphosgene (1.25 g, 4.20 mmol). The reaction mixture was stirred for 1 h, then quenched with H₂O (50 mL) and extracted with CH₂Cl₂ (3×50 mL). The combined organic layers were dried over Na₂SO₄, filtered, and concentrated under reduced pressure. The crude product was purified by silica gel chromatography, eluting with a gradient of CH₂Cl₂:MeOH—100:0 to 95:5, to give the title compound. MS: m/z=248 (M+1).

INTERMEDIATE 16

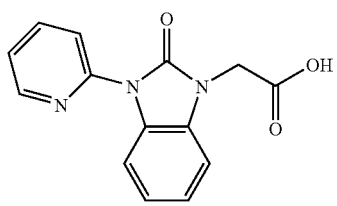

(2-Oxo-3-pyridin-2-yl-2,3-dihydro-1H-benzimidazol-1-yl)acetic Acid

Step A. tert-Butyl (2-oxo-2,3-dihydro-1H-benzimidazol-1-yl)acetate

To a stirred mixture of 2-hydroxybenzimidazole (4.00 g, 29.8 mmol) and tert-butyl bromoacetate (5.53 g, 28.3 mmol) in DMF (50 mL) at 0° C. was added sodium hydride (1.31 g of a 60% dispersion in mineral oil, 32.8 mmol). The mixture was stirred at 0° C. for 1 h, then quenched with saturated aqueous NaHCO₃ and concentrated in vacuo. The residue was partitioned between EtOAc (500 mL) and H₂O (300 mL) and the organic layer was dried over Na₂SO₄, filtered, and concentrated under reduced pressure. The crude product was purified by silica gel chromatography, eluting with a gradient of CH₂Cl₂:EtOAc—100:0 to 0:100, to give the title compound. MS: m/z=249 (M+1).

Step B. tert-Butyl (2-oxo-3-pyridin-2-yl-2,3-dihydro-1H-benzimidazol-1-yl)acetate A mixture of tert-butyl (2-oxo-2,3-dihydro-1H-benzimidazol-1-yl)acetate from Step A (1.75 g, 7.05 mmol), 2-bromopyridine (3.36 mL, 35.2 mmol), copper powder (1.57 g, 24.7 mmol), CuCl (140 mg, 1.41 mmol), and KOAc (2.08 g, 21.1 mmol) in pyridine (30 mL) was heated at 100° C. for 3 h. The cooled mixture was partitioned between EtOAc (150 mL) and 10% aqueous citric acid (100 mL) and the organic layer was dried over Na₂SO₄, filtered, and concentrated under reduced pressure. The crude product was purified by silica gel chromatography, eluting with a gradient of hexane:EtOAc—100:0 to 0:100, to give the title compound. MS: m/z=326 (M+1).

Step C. (2-Oxo-3-pyridin-2-yl-2,3-dihydro-1H-benzimidazol-1-yl)acetic Acid

A solution of tert-butyl (2-oxo-3-pyridin-2-yl-2,3-dihydro-1H-benzimidazol-1-yl)acetate from Step B (2.27 g, 6.98 mmol) in EtOAc (100 mL) at 0° C. was saturated with HCl (g). The mixture was stood at 0° C. for a total of 3 h, and was re-saturated with HCl every 30 min. The mixture was concentrated in vacuo to give the title compound. MS: m/z=270 (M+1).

INTERMEDIATE 17

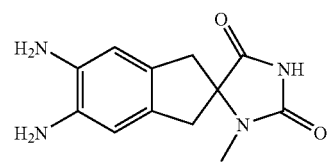

5',6'-Diamino-3-methyl-spiro[imidazolidine-4,2'-indane]-2,5-dione

Step A. (±)-5'-Amino-6'-nitro-3-methyl-spiro[imidazolidine-4,2'-indane]-2,5-dione To (±)-5'-amino-3-methyl-spiro[imidazolidine-4,2'-indane]-2,5-dione (100 mg, 0.432 mmol, described in Intermediate 7) at 0° C. were added 70% HNO₃ (1 mL) followed by conc. H₂SO₄ (1 mL). The resulting mixture was allowed to warm to ambient temperature and stirred for 18 h, then poured onto ice and the precipitate was removed by filtration. The aqueous filtrate was purified by HPLC using a reversed phase C18 column and eluting with a gradient of H₂O:CH₃CN:CF₃CO₂H—90:10:0.1 to 5:95:0.1. Lyophilization provided the title compound. MS: m/z=277 (M+1).

Step B. 5',6'-Diamino-3-methyl-spiro[imidazolidine-4,2'-indane]-2,5-dione

To a solution of (±)-5'-amino-6'-nitro-spiro[imidazolidine-4,2'-indane]-2,5-dione from Step A (15 mg, 0.054 mmol) in MeOH (5 mL) was added 10% Pd/C (5 mg) and the reaction mixture was stirred vigorously under hydrogen (ca. 1 atm). After 2 h, the catalyst was filtered off and the filtrate was concentrated in vacuo to yield the title compound. MS: m/z=247 (M+1).

INTERMEDIATE 18

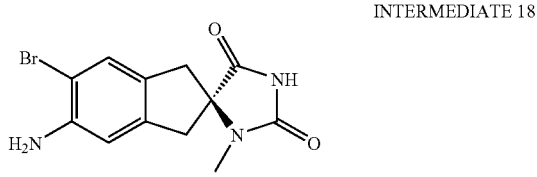

(S)-5'-Amino-6'-bromo-3-methyl-spiro[imidazolidine-4,2'-indane]-2,5-dione (R)-5'-Amino-3-methyl-spiro[imidazolidine-4,2'-indane]-2,5-dione (580 mg, 2.51 mmol, described in Intermediate 8) was suspended in CHCl$_3$ (250 mL) and N-bromosuccinimide (335 mg, 1.88 mmol) was added in one portion. The resulting mixture was stirred at ambient temperature for 40 min, then washed with dilute aqueous NaHCO$_3$ (50 mL). The organic layer was dried over Na$_2$SO$_4$, filtered, and concentrated under reduced pressure. The crude product was purified by silica gel chromatography, eluting with a gradient of CH$_2$Cl$_2$:EtOAc—100:0 to 0:100, to give (R)-5'-amino-4'-bromo-3-methyl-spiro[imidazolidine-4,2'-indane]-2,5-dione, which eluted first, and the title compound, which eluted second. MS: m/z=353 (M+1+CH$_3$CN).

INTERMEDIATE 19

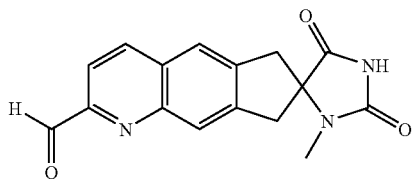

(±)-3'-Methyl-2',5'-dioxo-6,8-dihydrospiro[cyclopenta[g]quinoline-7,4'-imidazolidine]-2-carbaldehyde Essentially following the procedures described for Intermediate 13, but using (±)-5'-amino-3-methyl-spiro[imidazolidine-4,2'-indane]-2,5-dione (described in Intermediate 7) in place of (R)-5'-amino-3-methyl-spiro[imidazolidine-4,2'-indane]-2,5-dione, the title compound is prepared.

INTERMEDIATE 20

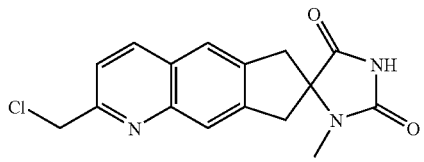

(±)-2-(Chloromethyl)-3'-methyl-6,8-dihydro-2'H,5'H-spiro[cyclopenta[g]quinoline-7,4'-imidazolidine]-2',5'-dione Essentially following the procedures described for Intermediate 14, but using (±)-3'-dimethyl-2',5'-dioxo-6,8-dihydrospiro[cyclopenta[g]quinoline-7,4'-imidazolidine]-2-carbaldehyde (described in Intermediate 19) in place of (7R)-3'-methyl-2',5'-dioxo-6,8-dihydrospiro[cyclopenta[g]quinoline-7,4'-imidazolidine]-2-carbaldehyde, the title compound is prepared.

INTERMEDIATE 21

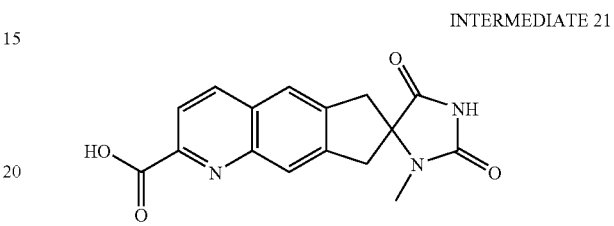

(±)-3'-Methyl-2',5'-dioxo-6,8-dihydrospiro[cyclopenta[g]quinoline-7,4'-imidazolidine]-2-carbolic acid A mixture of (±)-2,3'-dimethyl-6,8-dihydro-2'H,5'H-spiro[cyclopenta[g]quinoline-7,4'-imidazolidine]-2',5'-dione (500 mg, 1.78 mmol, described in Intermediate 19) and selenium dioxide (592 mg, 5.33 mmol) in dioxane (30 mL) and H$_2$O (3 mL) are heated at reflux for 18 h. The reaction mixture is allowed to cool, filtered through a pad of Celite, and the filtrate is concentrated in vacuo to give the title compound.

INTERMEDIATE 22

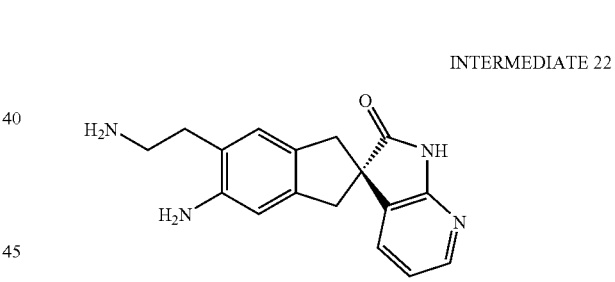

(2S)-5-Amino-6-(2-aminoethyl)-1,3-dihydrospiro[indene-2,3'-pyrrolo[2,3-b]pyridin]-2'(1'H)-one Step A. (2R)-5-Iodo-6-nitro-1,3-dihydrospiro[indene-2,3'-pyrrolo[2,3-b]pyridin]-2'(1'H)-one To a suspension of (S)-5-amino-6-nitro-1,3-dihydrospiro[indene-2,3'-pyrrolo[2,3-b]pyridin]-2'(1'H)-one (6.14 g, 20.7 mmol, described in Intermediate 13) in 3 N hydrochloric acid (50 mL) and THF (20 mL), at −5° C., was added NaNO$_2$ (1.60 g, 23.2 mmol) in H$_2$O (10 mL) dropwise at such a rate that the reaction temperature was maintained below 0° C. After a further 15 min, KI (9.2 g, 55 mmol) in H$_2$O (9 mL) was added dropwise over 30 min, keeping the reaction temperature below 0° C. After a further 15 min. the mixture was extracted with CH$_2$Cl$_2$ (3×300 mL), and the combined organic layers were dried over Na$_2$SO$_4$, decanted, and concentrated in vacuo. The crude product was purified by silica gel chromatography, eluting with a gradient of CH$_2$Cl$_2$:MeOH—100:0 to 90:10, to give the title compound, which was of sufficient purity for use in the next step. MS: m/z=408 (M+1).

Step B. (2R)-5-Iodo-6-nitro-1'-{[2-(trimethylsilyl) ethoxy]methyl}-1,3-dihydrospiro[indene-2,3'-pyrrolo[2,3-b]pyridin]-2'(1'H)-one Sodium hydride (60% dispersion in mineral oil; 525 mg, 13.1 mmol) was added to a solution of (2R)-5-iodo-6-nitro-1,3-dihydrospiro[indene-2,3'-pyrrolo[2,3-b]pyridin]-2'(1'H)-one from Step A (5.14 g, 12.6 mmol) in DMF (40 mL) at 0° C. and the mixture was stirred for 5 min. 2-(Trimethylsilyl)ethoxymethyl chloride (2.23 mL, 12.6 mmol) was then added dropwise, and the reaction mixture was stirred at 0° C. for 2 h. The reaction was quenched with dilute aqueous NaHCO₃ (200 mL) and the mixture was extracted with EtOAc (3×200 mL). The combined organic layers were washed with brine, dried over MgSO₄, filtered, and concentrated under reduced pressure. The crude product was purified by silica gel chromatography, eluting with a gradient of hexane:EtOAc—100:0 to 0:100, to give the title compound, which was of sufficient purity for use in the next step. MS: m/z=538 (M+1).

Step C. tert-Butyl ((2S)-6-nitro-2'-oxo-1'-{[2-(trimethylsilyl)ethoxy]methyl}-1,1',2',3-tetrahydrospiro [indene-2,3'-pyrrolo[2,3-b]pyridin]-5-yl)acetate To a flask containing (2R)-5-iodo-6-nitro-1'-{[2-(trimethylsilyl)ethoxy]methyl}-1,3-dihydrospiro[indene-2,3'-pyrrolo[2,3-b]pyridin]-2'(1'H)-one from Step B (4.02 g, 7.48 mmol), tris(dibenzylideneacetone)dipalladium (349 mg, 0.38 mmol), and 1,2,3,4,5-pentaphenyl-1'-(di-tert-butylphosphino)ferrocene (532 mg, 0.75 mmol) was added 2-tert-butoxy-2-oxoethylzinc chloride (Rieke, 0.5 M in Et₂O; 15.7 mL, 7.85 mmol) and the resulting solution was heated to 40° C. for 1 h. The reaction was quenched with dilute aqueous NaHCO₃ (100 mL) and the mixture was extracted with EtOAc (200 mL). The organic layer was washed with brine, dried over Na₂SO₄, filtered, and concentrated under reduced pressure. The crude product was purified by silica gel chromatography, eluting with a gradient of hexane:EtOAc—100:0 to 0:100, to give the title compound, which was of sufficient purity for use in the next step. MS: m/z=526 (M+1).

Step D. [(2S)-6-Nitro-2'-oxo-1,1',2',3-tetrahydrospiro [indene-23'-pyrrolo[2,3-b]pyridin]-5-yl]acetic Acid A solution of tert-butyl ((2S)-6-nitro-2'-oxo-1'-{[2-(trimethylsilyl)ethoxy]methyl}-1,1',2',3-tetrahydrospiro[indene-2,3'-pyrrolo[2,3-b]pyridin]-5-yl)acetate from Step C (2.01 g, 3.83 mmol) in MeOH (25 mL) was saturated with HCl (g) and stood at ambient temperature for 18 h. The mixture was concentrated to dryness in vacuo, then redissolved in MeOH (25 mL). This stirred solution was adjusted to pH 10 with 10 N NaOH and ethylene diamine (0.26 mL, 3.83 mmol) was added. The resulting mixture was stirred for 3 h, then concentrated to dryness in vacuo. The residue was dissolved in THF (25 mL) and 1 N NaOH (25 mL, 25 mmol) was added. The mixture was stirred at ambient temperature for 18 h, then the THF was removed under reduced pressure. The residual mixture was partitioned between saturated aqueous NaHCO₃ (50 mL) and EtOAc (100 mL). The organic layer was discarded and the aqueous layer was adjusted to pH 2 with aqueous HCl, then extracted with EtOAc (3×200 mL). The combined organic layers were dried over Na₂SO₄, filtered, and concentrated under reduced pressure to give the title compound. MS: m/z=340 (M+1).

Step E. (2S)-5-(2-Hydroxyethyl)-6-nitro-1,3-dihydrospiro[indene-2,3'-pyrrolo[2,3-b]pyridin]-2'(1'H)-one To a stirred solution of [(2S)-6-nitro-2'-oxo-1,1',2',3-tetrahydrospiro[indene-2,3'-pyrrolo[2,3-b]pyridin]-5-yl]acetic acid from Step D (753 mg, 2.22 mmol) in THF (15 mL), at −78° C., was added borane (1 M in THF; 9.1 mL, 9.1 mmol) dropwise. After 5 min, the mixture was warmed to 0° C. and stirring was continued at this temperature for 3 h. The reaction was quenched carefully with 1 N HCl and stirring was continued at ambient temperature. The mixture was adjusted to pH 8 with saturated aqueous NaHCO₃ and extracted with EtOAc (2×100 mL). The combined organic layers were dried over Na₂SO₄, filtered, and concentrated under reduced pressure. The crude product was purified by silica gel chromatography, eluting with a gradient of CH₂Cl₂:MeOH—100:0 to 80:20, to give the title compound. MS: m/z=326 (M+1).

Step F. (2S)-5-(2-Azidoethyl)-6-nitro-1,3-dihydrospiro[indene-2,3'-pyrrolo[2,3-b]pyridin]-2'(1'H)-one To a stirred solution of (2S)-5-(2-hydroxyethyl)-6-nitro-1,3-dihydrospiro[indene-2,3'-pyrrolo[2,3-b]pyridin]-2'(1'H)-one from Step E (174 mg, 0.54 mmol) in DMF (4 mL) were added diphenyl phosphoryl azide (177 mg, 0.64 mmol) and DBU (0.096 mL, 0.64 mmol). The mixture was heated at 100° C. for 6 h, then quenched with H₂O (20 mL) and extracted with EtOAc (50 mL). The organic layer was dried over Na₂SO₄, filtered, and concentrated under reduced pressure. The crude product was purified by silica gel chromatography, eluting with a gradient of CH₂Cl₂:MeOH—100:0 to 80:20, to give the title compound. MS: m/2=351 (M−1).

Step G. (2S)-5-Amino-6-(2-aminoethyl)-1,3-dihydrospiro[indene-2,3'-pyrrolo[2,3-b]pyridin]-2'(1'H)-one To a solution of (2S)-5-(2-azidoethyl)-6-nitro-1,3-dihydrospiro[indene-2,3'-pyrrolo[2,3-b]pyridin]-2'(1'H)-one from Step F (236 mg, 0.67 mmol) in EtOH (15 mL) was added 10% Pd/C (172 mg). The reaction mixture was stirred under a hydrogen atmosphere (ca. 1 atm) for 5 h, then filtered through a Celite pad, washing with MeOH, and the filtrate was concentrated under reduced pressure to give the title compound. MS: m/z=295 (M+1).

INTERMEDIATE 23

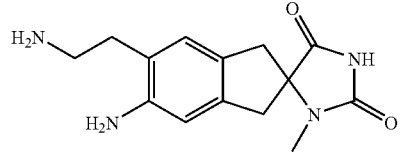

(±)-5'-Amino-6'-(2-aminoethyl)-3-methyl-1',3'-dihydro-2H,5H-spiro[imidazolidine-4,2'-indene]-2,5-dione Essentially following the procedures described for Intermediate 26, but using (±)-5'-amino-6'-nitro-spiro[imidazolidine-4,2'-indane]-2,5-dione (described in Intermediate 22) in place of (S)-5-amino-6-nitro-1,3-dihydrospiro[indene-2,3'-pyrrolo[2,3-b]pyridin]-2'(1'H)-one, the title compound is prepared.

INTERMEDIATE 24

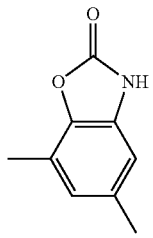

5,7-Dimethyl-2-benzoxazolinone

A mixture of 2-amino-4,6-dimethylphenol (412 mg, 3.00 mmol) and 1,1'-carbonyldiimidazole (730 mg, 4.50 mmol) in THF (15 mL) was heated at reflux for 3 h. The mixture was allowed to cool, and the solvent removed under reduced pressure. The residue was taken up in EtOAc and washed with 1.0 N aqueous HCl (2×), then brine, then the EtOAc was dried over $Na_2SO_4$, filtered, and concentrated in vacuo to give the title compound. MS: m/z=164 (M+1).

INTERMEDIATE 25

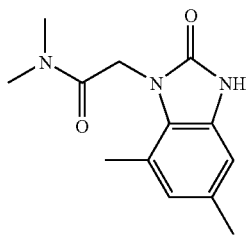

2-(5,7-Dimethyl-2-oxo-2,3-dihydro-1H-benzimidazol-1-yl)-N,N-dimethylacetamide

Step A. $N^2$-(2,4-Dimethyl-6-nitrophenyl)-$N^1,N^1$-dimethylglycinamide

A mixture of 2,4-dimethyl-6-nitroaniline (5.00 g, 30.1 mmol), 2-chloro-N,N-dimethylacetamide (18.3 g, 150 mmol), $K_2CO_3$ (6.24 g, 45.2 mmol), and KI (499 mg, 3.01 mmol) in DMF (100 mL) was heated at 120° C. for 7 h, then at 130° C. for 14 h. The cooled mixture was quenched with $H_2O$ (200 mL) and extracted with $CH_2Cl_2$ (3×150 mL). The combined organic layers were dried over $Na_2SO_4$, filtered, and concentrated under reduced pressure. The crude product was purified by silica gel chromatography, eluting with a gradient of hexane:EtOAc—100:0 to 50:50, to give the title compound. MS: m/z=252 (M+1).

Step B. $N^2$-(2-Amino-4,6-dimethylphenyl)-$N^1,N^1$-dimethylglycinamide

To a solution of $N^2$-(2,4-dimethyl-6-nitrophenyl)-$N^1,N^1$-dimethylglycinamide from Step A (2.54 g, 10.1 mmol) in EtOH (50 mL) was added 10% Pd/C (500 mg). The reaction mixture was stirred under a hydrogen atmosphere (ca. 1 atm) for 72 h, then filtered through a Celite pad, washing with EtOH, and the filtrate was concentrated under reduced pressure. The crude product was purified by silica gel chromatography, eluting with a gradient of hexane:EtOAc—100:0 to 0:100, to give the title compound. MS: m/z=222 (M+1).

Step C. 2-(5,7-Dimethyl-2-oxo-2,3-dihydro-1H-benzimidazol-1-yl)-N,N-dimethylacetamide To a solution of $N^2$-(2-amino-4,6-dimethylphenyl)-$N^1,N^1$-dimethylglycinamide from Step B (930 mg, 4.20 mmol) in $CH_3CN$ (20 mL) at 0° C. was added triphosgene (1.25 g, 4.20 mmol). The reaction mixture was stirred for 1 h, then quenched with $H_2O$ (50 mL) and extracted with $CH_2Cl_2$ (3×50 mL). The combined organic layers were dried over $Na_2SO_4$, filtered, and concentrated under reduced pressure. The crude product was purified by silica gel chromatography, eluting with a gradient of $CH_2Cl_2$:MeOH—100:0 to 95:5, to give the title compound. MS: m/z=248 (M+1).

INTERMEDIATE 26

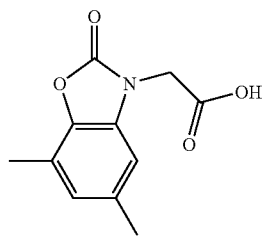

(5,7-Dimethyl-2-oxo-1,3-benzoxazol-3(2H)-yl)acetic acid

Step A. tert-Butyl (5,7-dimethyl-2-oxo-1,3-benzoxazol-3(2H)-yl)acetate

To a stirred solution of 5,7-dimethyl-2-benzoxazolinone (200 mg, 1.23 mmol, described in Intermediate 24) in DMF (2 mL) was added sodium hydride (59 mg of a 60% dispersion in mineral oil, 1.47 mmol). The mixture was stirred at ambient temperature for 10 min, then tert-butyl bromoacetate (287 mg, 1.47 mmol) was added and stirring was continued for 2 h. The reaction mixture was quenched with $H_2O$ and purified directly by HPLC using a reversed phase C18 column and eluting with a gradient of $H_2O$:$CH_3CN$:$CF_3CO_2H$—90:10:0.1 to 5:95:0.1. Lyophilization provided the title compound. MS: m/z=222 (M−$C_4H_7$).

Step B. (5,7-Dimethyl-2-oxo-1,3-benzoxazol-3(2H)-yl)acetic acid

A solution of the tert-butyl (5,7-dimethyl-2-oxo-1,3-benzoxazol-3(2H)-yl)acetate from Step A in $CH_2Cl_2$ (0.7 mL) and $CF_3CO_2H$ (0.3 mL) was stood at ambient temperature for 2 h. Toluene (5 mL) was added and the mixture was concentrated in vacuo to give the title compound as a dark solid. MS: m/z=222 (M+1).

INTERMEDIATE 27

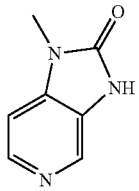

(1-Methyl-1,3-dihydro-2H-imidazo[4,5-c]pyridin-2-one

To a stirred suspension of 3-amino-4-methylaminopyridine [U.S. Pat. No. 5,371,086 (1993)] (190 mg, 1.54 mmol) in $CH_3CN$ (10 mL) was added triphosgene (458 mg, 1.54 mmol) portionwise. After 1 h, the mixture was concentrated in vacuo and the residue was converted to the free base by ion exchange chromatography on a SCX cartridge, eluting with 2 M $NH_3$ in MeOH to give the title compound. MS: m/z=150 (M+1).

Example 1

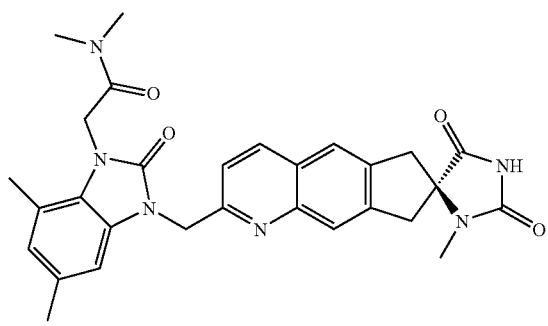

2-(5,7-Dimethyl-3-{[(7R)-3'-methyl-2',5'-dioxo-6,8-dihydrospiro[cyclopenta[g]quinoline-7,4'-imidazolidin]-2-yl]methyl}-2-oxo-2,3-dihydro-1H-benzimidazol-1-yl)-N,N-dimethylacetamide To a solution of 2-(5,7-dimethyl-2-oxo-2,3-dihydro-1H-benzimidazol-t-yl)-N,N-dimethylacetamide (157 mg, 0.633 mmol, described in Intermediate 15) in DMF (0.5 mL), at 0° C., was added sodium hydride (60% dispersion in mineral oil; 28 mg, 0.70 mmol) and the resulting mixture was stirred for 30 min. A solution of (7R)-2-(chloromethyl)-3'-methyl-6,8-dihydro-2'H,5'H-spiro[cyclopenta[g]quinoline-7,4'-imidazolidine]-2',5'-dione (100 mg, 0.32 mmol, described in Intermediate 14) in DMF (1 mL) was added dropwise and the resulting mixture was stirred at ambient temperature for 2 h. The reaction mixture was quenched with a few drops of TFA and purified directly by HPLC using a reversed phase C18 column and eluting with a gradient of $H_2O:CH_3CN:CF_3CO_2H$—90:10:0.1 to 5:95:0.1. The pure, product-containing fractions were combined and poured into saturated aqueous $NaHCO_3$ (10 mL). The mixture was extracted with $CH_2Cl_2$ (3×10 mL). The combined organic extracts were dried over $Na_2SO_4$, filtered, and concentrated in vacuo to give the title compound. MS: m/z=527 (M+1). HRMS: m/z=527.2413; calculated m/z=527.2402 for $C_{29}H_{31}N_6O_4$.

Example 2

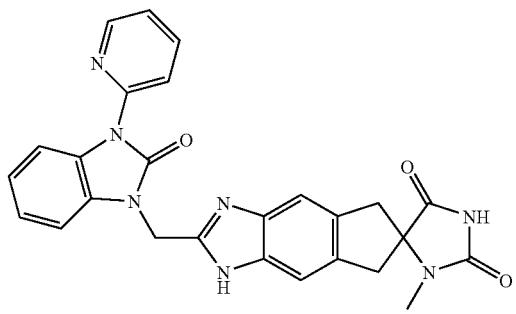

3-Methyl-2'-[(2-oxo-3-pyridin-2-yl-2,3-dihydro-1H-benzimidazol-1-yl)methyl]-5',7'-dihydro-1'H,2H,5H-spiro[imidazolidine-4,6'-indeno[5,6-d]imidazole]-2,5-dione A stirred mixture of (2-oxo-3-pyridin-2-yl-2,3-dihydro-1H-benzimidazol-1-yl)acetic acid (14 mg, 0.053 mmol, described in Intermediate 16) and 5',6'-diamino-3-methyl-spiro[imidazolidine-4,2'-indane]-2,5-dione (13 mg, 0.053 mmol, described in Intermediate 17) in 3 N HCl (1 mL) was heated at 100° C. for 26 h. The cooled mixture was purified by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound as the trifluoroacetate salt. MS: m/z=480 (M+1). HRMS: m/z=480.1782; calculated m/z=480.1779 for $C_{26}H_{21}N_7O_3$.

Example 3

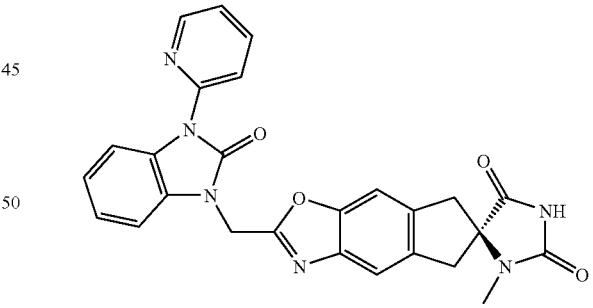

3-Methyl-2'-[(2-oxo-3-pyridin-2-yl-2,3-dihydro-1H-benzimidazol-1-yl)methyl]-5',7'-dihydro-1'H,2H,5H-spiro[imidazolidine-4,6'-indeno[5,6-d]imidazole]-2,5-dione Step A. N-[(4S)-6'-Bromo-3-methyl-2,5-dioxo-1',3'-dihydrospiro[imidazolidine-4,2'-inden]-5'-yl]-2-(2-oxo-3-pyridin-2-yl-2,3-dihydro-1H-benzimidazol-1-yl)acetamide To a stirred mixture of (S)-5'-amino-6'-bromo-3-methyl-spiro[imidazolidine-4,2'-indane]-2,5-dione (50 mg, 0.161 mmol, described in Intermediate 18) and (2-oxo-3-pyridin-2-yl-2,3-dihydro-1H-benzimidazol-1-yl)acetic acid (52 mg, 0.193 mmol, described in Intermediate 16) in DMF (1 mL) were added N,N-diisopropylethylamine (0.028 mL, 0.161 mmol), followed by PyBOP (126 mg, 0.242 mmol). The reaction mixture was heated to 40° C. for 5 h, then PyBOP (126 mg, 0.242 mmol) was added and heating was continued for 18 h. The cooled mixture was purified by HPLC using a reversed phase C18 column and eluting with a gradient of $H_2O:CH_3CN:CF_3CO_2H$-90:10:0.1 to 5:95:0.1. The pure, product-containing fractions were combined and concentrated to give the title compound. MS: m/z=563 (M+1).

Step B. (4S)-3-Methyl-2'-[(2-oxo-3-pyridin-2-yl-2,3-dihydro-1H-benzimidazol-1-yl)methyl]-5',7'-dihydro-2H,5H-spiro[imidazolidine-4,6'-indeno[5,6-d][1,3]oxazole]-2,5-dione A stirred mixture of N-[(4S)-6'-bromo-3-methyl-2,5-dioxo-1',3'-dihydrospiro[imidazolidine-4,2'-inden]-5'-yl]-2-(2-oxo-3-pyridin-2-yl-2,3-dihydro-1H-benzimidazol-1-yl)acetamide from Step A (16 mg, 0.029 mmol), $K_2CO_3$ (6 mg, 0.043 mmol), and CuBr (8 mg, 0.057 mmol) in DMF (1 mL) and pyridine (0.1 mL) was heated to 140° C. for 6 h. The cooled mixture was partitioned between EtOAc (20 mL) and saturated aqueous $NaHCO_3$ (10 mL) and the organic layer was dried over $Na_2SO_4$, filtered, and concentrated under reduced pressure. The residue was triturated with MeOH to give a pale solid. This solid was further purified by silica gel chromatography, eluting with a gradient of $CH_2Cl_2$:MeOH—100:0 to 90:10, to give the title compound. MS: m/z=481 (M+1). HRMS: m/z=481.1598; calculated m/z=481.1619 for $C_{26}H_{21}N_6O_4$.

Example 4

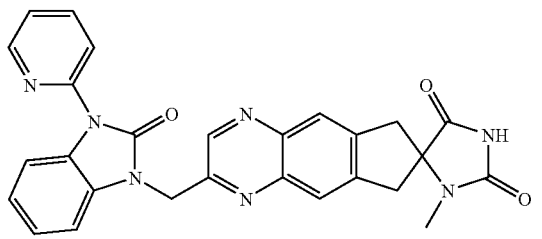

(±)-3'-Methyl-2-[(2-oxo-3-pyridin-2-yl-2,3-dihydro-1H-benzimidazol-1-yl)methyl]-6,8-dihydro-2'H,5'H-spiro[cyclopenta[g]quinoxaline-7,4'-imidazolidine]-2',5'-dione Step A. 1-(3-Imino-2-oxopropyl)-3-pyridin-2-yl-1,3-dihydro-2H-benzimidazol-2-one To a stirred solution of (2-oxo-3-pyridin-2-yl-2,3-dihydro-1H-benzimidazol-1-yl)acetic acid (144 mg, 0.535 mmol, described in Intermediate 16) in THF (5 mL) at −10° C. was added triethylamine (0.097 mL, 0.695 mmol), followed by isobutyl chloroformate (0.090 mL, 0.695 mmol) and the resulting mixture was stirred at −10° C. for 3 h. A cold solution of diazomethane (ca. 1.0 mmol) in $Et_2O$ (3 mL) was added, and stirring was continued for 16 h, allowing the mixture to warm slowly to ambient temperature. The mixture was cooled to −10° C. and a cold solution of diazomethane (ca. 1.5 mmol) in $Et_2O$ (5 mL) was added, and the resulting mixture was allowed to warm to ambient temperature and stirred for 3 h. The solvent was removed in vacuo and the residue was partitioned between $Et_2O$ (20 mL) and saturated aqueous $NaHCO_3$ (10 mL). The aqueous layer was extracted further with $Et_2O$ (2×10 mL) and the combined organic layers were dried over $Na_2SO_4$, filtered, and concentrated under reduced pressure. The residue was triturated with MeOH to give a pale solid. This solid was further purified by silica gel chromatography, eluting with a gradient of hexane:EtOAc—100:0 to 50:50, to give the title compound. MS: m/z=266 (M−N).

Step B. 2-Oxo-3-(2-oxo-3-pyridin-2-yl-2,3-dihydro-1H-benzimidazol-1-yl)propanal

To a stirred solution of 1-(3-imino-2-oxopropyl)-3-pyridin-2-yl-1,3-dihydro-2H-benzimidazol-2-one from Step A (54 mg, 0.19 mmol) in acetone (2 mL) at 0° C. was added a solution of dimethyldioxirane (0.02 M in acetone, 9.6 mL, 0.19 mmol). The reaction mixture was stirred for 90 min then concentrated in vacuo to give the title compound in sufficient purity for use in the next step.

Step C. (±)-3'-Methyl-2-[(2-oxo-3-pyridin-2-yl-2,3-dihydro-1H-benzimidazol-1-yl)methyl]-6,8-dihydro-2'H,5'H-spiro[cyclopenta[g]quinoxaline-7,4'-imidazolidine]-2',5'-dione A mixture of 2-oxo-3-(2-oxo-3-pyridin-2-yl-2,3-dihydro-1H-benzimidazol-1-yl)propanal from Step B (54 mg, 0.19 mmol), 5',6'-diamino-3-methyl-spiro[imidazolidine-4,2'-indane]-2,5-dione (47 mg, 0.19 mmol, described in Intermediate 17), and $MgSO_4$ (ca. 5 g) was stirred in $CH_2Cl_2$ (10 mL) and MeOH (10 mL) at ambient temperature for 13 h. The mixture was filtered and concentrated under reduced pressure. The residue was purified by silica gel chromatography, eluting with a gradient of $CH_2Cl_2$:MeOH:$NH_4OH$—100:0:0 to 90:9:1, to give the title compound. MS: m/z=492 (M+1). HRMS: m/z=492.1781; calculated m/z=492.1779 for $C_{27}H_{22}N_7O_3$.

Example 5

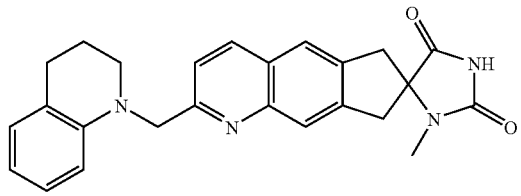

(±)-2-(3,4-Dihydroquinolin-1(2H)-ylmethyl)-3'-methyl-6,8-dihydro-2'H,5'H-spiro[cyclopenta[g]quinoline-7,4'-imidazolidine]-2',5'-dione To a stirred solution of (±)-3'-methyl-2',5'-dioxo-6,8-dihydrospiro[cyclopenta[g]quinoline-7,4'-imidazolidine]-2-carbaldehyde (19 mg, 0.063 mmol, described in Intermediate 19), 1,2,3,4-tetrahydroquinoline (13 mg, 0.095 mmol), and AcOH (0.0054 mL, 0.095 mmol) in MeOH (1 mL) is added $NaCNBH_3$ (6 mg, 0.095 mmol). The mixture is quenched with TFA and concentrated to dryness in vacuo. The residue is purified by HPLC using a reversed phase C18 column and eluting with a gradient of H₂O:CH₃CN:CF₃CO₂H—90:10:0.1 to 5:95:0.1. The pure, product-containing fractions are combined and concentrated to give the title compound.

Example 6

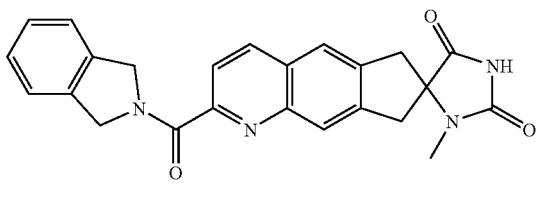

(±)-2-(1,3-Dihydro-2H-isoindol-2-ylcarbonyl)-3'-methyl-6,8-dihydro-2'H,5'H-spiro[cyclopenta[g]quinoline-7,4'-imidazolidine]-2',5'-dione A mixture of (±)-3'-methyl-2',5'-dioxo-6,8-dihydrospiro[cyclopenta[g]quinoline-7,4'-imidazolidine]-2-carboxylic acid (9 mg, 0.030 mmol, described in Intermediate 21), isoindoline (7 mg, 0.060 mmol), EDC (9 mg, 0.045 mmol), HOBT (7 mg, 0.045 mmol), and N,N-diisopropylethylamine (0.026 mL, 0.151 mmol) is stirred in DMF (1 mL) at ambient temperature for 18 h. The reaction mixture is purified directly by HPLC using a reversed phase C18 column and eluting with a gradient of H₂O:CH₃CN:CF₃CO₂H—90:10:0.1 to 5:95:0.1. The pure, product-containing fractions are combined and concentrated to give the title compound.

Example 7

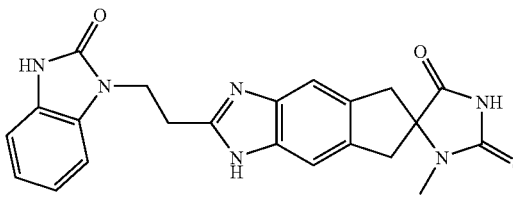

3-Methyl-2'-[2-(2-oxo-2,3-dihydro-1H-benzimidazol-1-yl)ethyl]-5',7'-dihydro-1'H,2'H,5H-spiro[imidazolidine-4,6'-indeno[5,6-d]imidazole]-2,5-dione A mixture of 5',6'-diamino-3-methyl-spiro[imidazolidine-4,2'-indane]-2,5-dione (27 mg, 0.11 mmol, described in intermediate 17), 3-(2-oxo-2,3-dihydro-1H-benzimidazol-1-yl)propanoic acid [Mitskyavichyus & Sapiyanskaite, *Chem. Heterocycl. Compd.*, 1985, 21, 1251-1254] (21 mg, 0.10 mmol), BOP (50 mg, 0.11 mmol), and N,N-diisopropylethylamine (0.019 mL, 0.11 mmol) is stirred in DMF (0.4 mL) at ambient temperature for 1 h, then AcOH (0.4 mL) is added and the resulting mixture is heated to 60° C. for 6 h. The reaction mixture is purified directly by HPLC using a reversed phase C18 column and eluting with a gradient of H₂O:CH₃CN:CF₃CO₂H—90:10:0.1 to 5:95:0.1. The pure, product-containing fractions are combined and concentrated to give the title compound.

Examples 8-13

Essentially following the procedures outlined for Example 1 the compounds listed in Table 1 are prepared. The requisite starting materials are commercially available, described in the literature, synthesized according to methodology described herein (vide supra), or readily synthesized by one skilled in the art of organic synthesis. In some cases, straightforward protecting group strategies are applied.

TABLE 1

| Example | $R^b$ |
|---|---|
| 8 | Br-benzoxazol-2(3H)-one |
| 9 | 4,6-dimethylbenzoxazol-2(3H)-one |
| 10 | benzoxazol-2(3H)-one |
| 11 | 1H-benzimidazol-2(3H)-one |
| 12 | 1-methyl-1H-imidazo[4,5-b]pyridin-2(3H)-one |
| 13 | 3,3-dimethyl-1,3-dihydro-2H-indol-2-one |

Examples 14-28

Essentially following the procedures outlined for Example 5 the compounds listed in Table 2 are prepared. The requisite amines are commercially available, described in the literature, synthesized according to methodology described herein (vide supra), or readily synthesized by one skilled in the art of organic synthesis. In some cases, straightforward protecting group strategies are applied.
TABLE 2
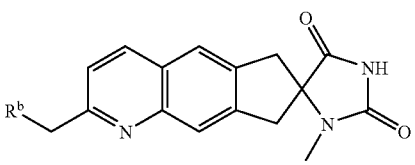
| Example | $R^b$ |
|---|---|
| 14 | 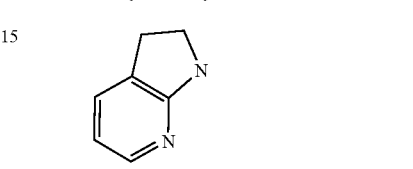 |
| 15 | 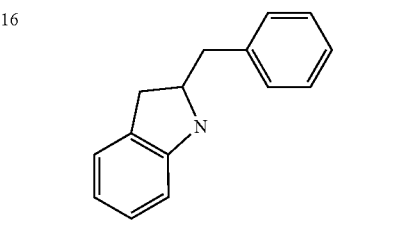 |
| 16 | 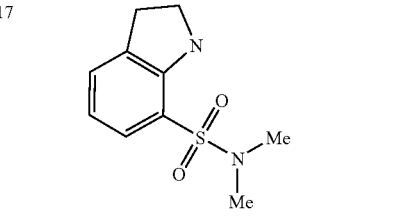 |
| 17 | 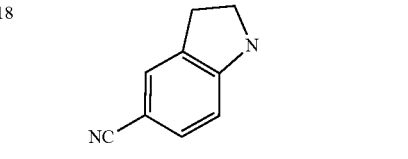 |
| 18 | 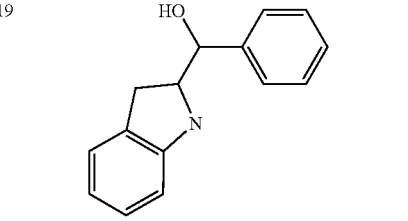 |
| 19 | 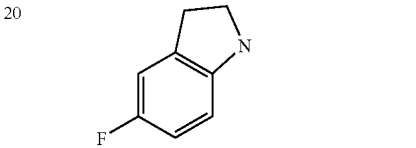 |
| 20 | 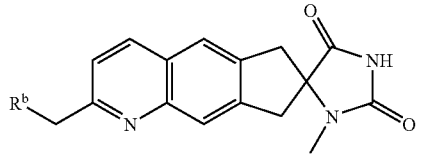 |
TABLE 2-continued
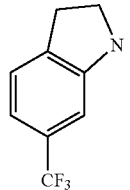
| Example | $R^b$ |
|---|---|
| 21 | 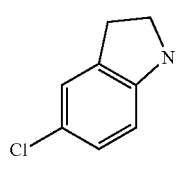 |
| 22 | 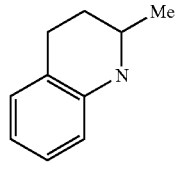 |
| 23 | 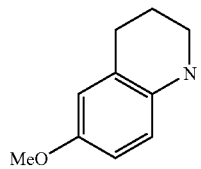 |
| 24 | 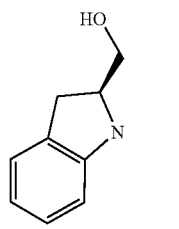 |
| 25 | 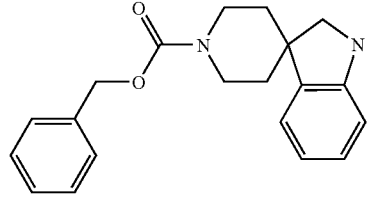 |
| 26 | 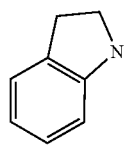 |
| 27 |  |

TABLE 2-continued

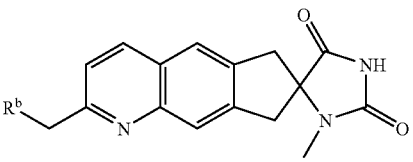

| Example | $R^b$ |
|---|---|
| 28 | 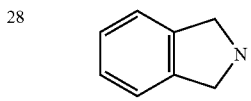 |

Examples 29-34

Essentially following the procedures outlined for Example 7 the compounds listed in Table 3 are prepared. The requisite carboxylic acids are commercially available, described in the literature, synthesized according to methodology described herein (vide supra), or readily synthesized by one skilled in the art of organic synthesis. In some cases, straightforward protecting group strategies are applied.

TABLE 3

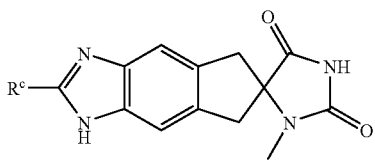

| Example | $R^c$ |
|---|---|
| 29 | 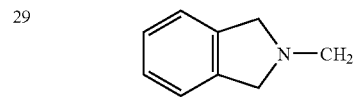 |
| 30 | 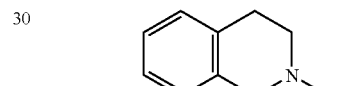 |
| 31 | 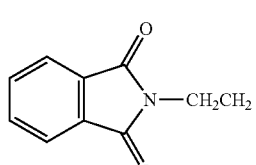 |
| 32 | 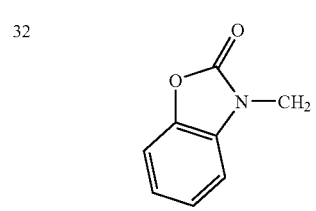 |

TABLE 3-continued

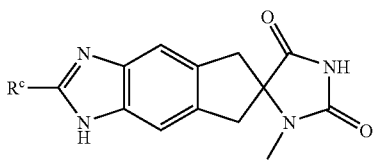

| Example | $R^c$ |
|---|---|
| 33 | 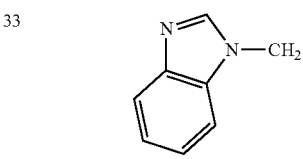 |
| 34 | 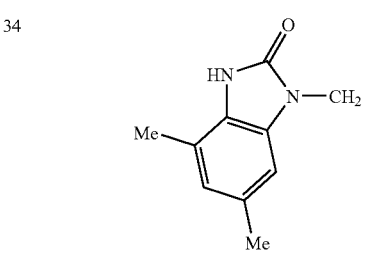 |

Example 35

Essentially following the procedures outlined for Example 1 the compounds listed in Table 4 were prepared. The requisite starting materials were commercially available, described in the literature, synthesized according to methodology described herein (vide supra), or readily synthesized by one skilled in the art of organic synthesis. In some cases, straightforward protecting group strategies were applied.

TABLE 4

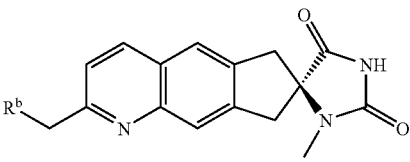

| Example | $R^b$ | M + 1 |
|---|---|---|
| 35 | 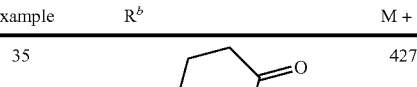 | 427 |
| 36 | 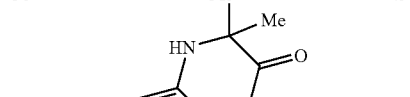 | 456 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

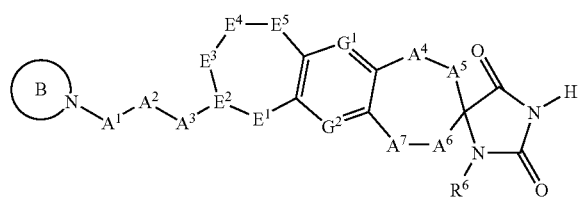

I wherein:

B is a bicycloheterocycle selected from the group consisting of:

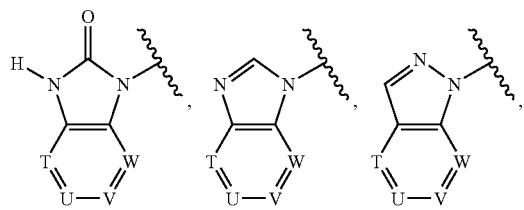

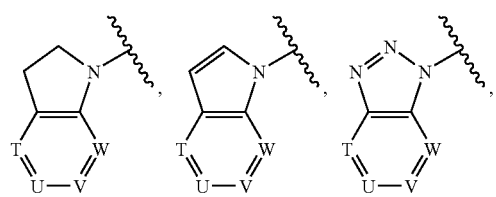

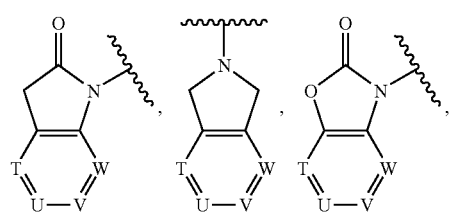

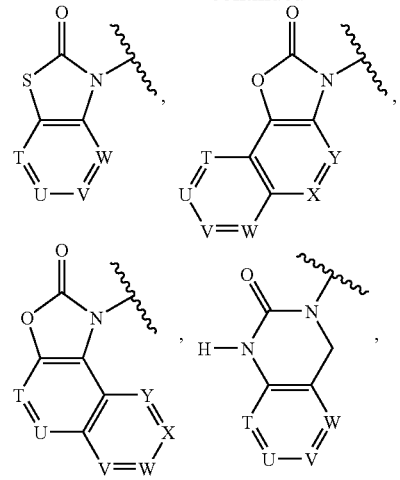

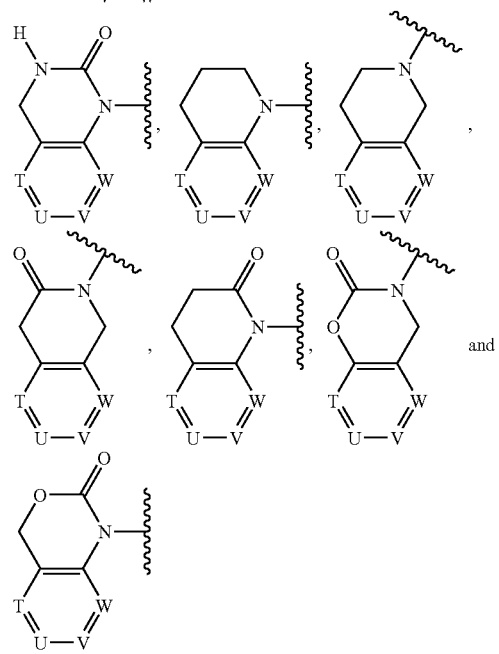

and where T, U, V, W, X and Y are each independently a carbon atom or a nitrogen atom, wherein no more than two of T, U, V and W, or no more than three of T, U, V, W, X and Y, are a nitrogen atom, where B is unsubstituted or substituted with 1-5 substituents independently selected from $R^1$, $R^2$, $R^{3a}$ and $R^{3b}$, where $R^1$, $R^2$, $R^{3a}$ and $R^{3b}$ are independently selected from:

(1) —$C_{1-6}$alkyl, which is unsubstituted or substituted with 1-7 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: azetidinyl, imidazolyl, oxazolyl, pyridyl, pyrimidinyl, pyrazinyl, pyridazinyl, piperidinyl, azepanyl, azepinyl, piperazinyl, pyrazolyl, pyrrolidinyl, thiazolyl, thienyl, triazolyl, tetrazolyl, tetrahydrofuryl, and morpholinyl,
    which phenyl or heterocycle is unsubstituted or substituted with 1-5 substituents each independently selected from:

(i) —$C_{1-6}$alkyl,
(ii) —O—$C_{1-6}$alkyl,
(iii) halo,
(iv) hydroxy,
(v) trifluoromethyl,
(vi) —$OCF_3$,
(vii) oxo,
(viii) amino,
(ix) phenyl, and
(x) benzyl,
(f) —$CO_2R^9$, wherein $R^9$ is independently selected from:
(i) hydrogen,
(ii) —$C_{1-6}$alkyl, which is unsubstituted or substituted with 1-6 substituents, substituents each independently selected from:
(I) halo,
(II) hydroxy,
(III) —O—$C_{1-6}$alkyl, which is unsubstituted or substituted with 1-5 halo,
(IV) —$C_{3-6}$cycloalkyl,
(V) phenyl, which is unsubstituted or substituted with 1-5 substituents each independently selected from:
(1) —$C_{1-4}$alkyl,
(2) —O—$C_{1-6}$alkyl,
(3) halo,
(4) trifluoromethyl, and
(5) —$OCF_3$,
(iii) —$C_{3-6}$cycloalkyl, which is unsubstituted or substituted with 1-5 halo, and
(iv) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:
(I) halo,
(II) —$C_{1-6}$alkyl, which is unsubstituted or substituted with 1-5 halo
(III) —O—$C_{1-6}$alkyl, which is unsubstituted or substituted with 1-5 halo
(IV) —$C_{3-6}$cycloalkyl,
(V) oxo,
(VI) —CN,
(VII) hydroxy, and
(VIII) phenyl,
(g) —$NR^{10}R^{11}$, wherein $R^{10}$ and $R^{11}$ are each independently selected from:
(i) hydrogen,
(ii) —$C_{1-6}$alkyl, which is unsubstituted or substituted with 1-6 substituents each independently selected from:
(I) —O—$C_{1-6}$alkyl,
(II) halo,
(III) hydroxy,
(IV) —$OCF_3$,
(V) —$C_{3-6}$cycloalkyl, and
(VI) phenyl,
(iii) —$C_{4-6}$cycloalkyl,
(iv) phenyl, which is unsubstituted or substituted with 1-5 substituents each independently selected from:
(I) —$C_{1-6}$alkyl,
(II) —O—$C_{1-6}$alkyl,
(III) halo,
(IV) hydroxy,
(V) trifluoromethyl,
(VI) —$OCF_3$, and
(VII) CN, and
(v) benzyl, which is unsubstituted or substituted with 1-5 substituents each independently selected from:
(I) —$C_{1-6}$alkyl,
(II) —O—$C_{1-6}$alkyl,
(III) halo, and
(IV) trifluoromethyl,
(vi) —$COR^9$, and
(vii) —$SO_2R^{12}$,
(h) —$SO_2R^{12}$, wherein $R^{12}$ is selected from:
(i) —$C_{1-6}$alkyl, which is unsubstituted or substituted with 1-6 fluoro,
(ii) —$C_{3-6}$cycloalkyl,
(iii) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl,
which phenyl or heterocycle is unsubstituted or substituted with 1-5 substituents each independently selected from:
(I) —$C_{1-6}$alkyl,
(II) —O—$C_{1-6}$alkyl,
(III) halo,
(IV) hydroxy,
(V) trifluoromethyl,
(VI) —$OCF_3$, and
(VII) CN, and
(iv) benzyl, which is unsubstituted or substituted with 1-5 substituents each independently selected from:
(I) —$C_{1-6}$alkyl,
(II) —O—$C_{1-6}$alkyl,
(III) halo, and
(IV) trifluoromethyl,
(i) —$CONR^{10a}R^{11a}$, wherein $R^{10a}$ and $R^{11a}$ are each independently selected from:
(i) hydrogen,
(ii) —$C_{1-6}$alkyl, which is unsubstituted or substituted with 1-6 substituents each independently selected from:
(I) —O—$C_{1-6}$alkyl,
(II) halo,
(III) hydroxy,
(IV) —$OCF_3$,
(V) —$C_{3-6}$cycloalkyl, and
(VI) phenyl,
(iii) —$C_{5-6}$cycloalkyl,
(iv) phenyl, which is unsubstituted or substituted with 1-5 substituents each independently selected from:
(I) —$C_{1-6}$alkyl,
(II) —O—$C_{1-6}$alkyl,
(III) halo,
(IV) hydroxy,
(V) trifluoromethyl,
(VI) —$OCF_3$, and
(VII) CN, and
(v) benzyl, which is unsubstituted or substituted with 1-5 substituents each independently selected from:
(I) —$C_{1-6}$alkyl,
(II) —O—$C_{1-6}$alkyl,
(III) halo, and
(IV) trifluoromethyl, or where $R^{10a}$ and $R^{11a}$ join to form a ring selected from azetidinyl, pyrrolidinyl, piperidinyl, azepanyl, piperazinyl, and morpholinyl, which ring is unsubstituted or substituted with 1-5 substituents each independently selected from:
- (I) —$C_{1-6}$alkyl
- (II) —O—$C_{1-6}$alkyl
- (III) halo
- (IV) hydroxy
- (V) phenyl,
- (VI) benzyl,
- (VII) —$COR^9$, and
- (VIII) —$SO_2R^{12}$, (j) trifluoromethyl,
(k) —$OCO_2R^9$,
(l) —$(NR^{10a})CO_2R^9$,
(m) —$O(CO)NR^{10a}R^{11a}$,
(n) —$(NR^9)(CO)NR^{10a}R^{11a}$,
(o) —$SO_2NR^{10a}R^{11a}$, and
(p) —O—$C_{3-6}$cycloalkyl, (2) —$C_{3-6}$cycloalkyl, which is unsubstituted or substituted with 1-7 substituents each independently selected from:
- (a) halo,
- (b) hydroxy,
- (c) —O—$C_{1-6}$alkyl,
- (d) trifluoromethyl,
- (e) phenyl, which is unsubstituted or substituted with 1-5 substituents each independently selected from:
  - (i) —$C_{1-6}$alkyl,
  - (ii) —O—$C_{1-6}$alkyl,
  - (iii) halo,
  - (iv) hydroxy, and
  - (v) trifluoromethyl, (3) phenyl or heterocycle, wherein heterocycle is selected from: pyridyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, 1,3-dioxolanyl, oxadiazolyl, piperidinyl, tetrahydropyranyl, tetrahydrothienyl, tetrahydrothiopyranyl, and morpholinyl, which phenyl or heterocycle is unsubstituted or substituted with 1-5 substituents each independently selected from:
- (a) —$C_{1-6}$alkyl, which is unsubstituted or substituted with 1-5 substituents each independently selected from:
  - (a) halo,
  - (b) hydroxy,
  - (c) —O—$C_{1-6}$alkyl,
  - (d) —$C_{3-6}$cycloalkyl,
  - (e) phenyl,
  - (f) —$CO_2R^9$, and
  - (g) —$NR^{10}R^{11}$,
- (b) halo,
- (c) hydroxy,
- (d) —O—$C_{1-6}$alkyl, which is unsubstituted or substituted with 1-6 fluoro,
- (e) —$C_{3-6}$cycloalkyl,
- (f) phenyl or heterocycle, wherein heterocycle is selected from: pyrrolidinyl, piperidinyl, piperazinyl, pyridyl, pyrimidinyl, pyrazinyl, thienyl, and morpholinyl, which phenyl or heterocycle is unsubstituted or substituted with 1-5 substituents each independently selected from:
  - (i) —$C_{1-6}$alkyl,
  - (ii) —O—$C_{1-6}$alkyl,
  - (iii) halo,
  - (iv) hydroxy, and
  - (v) trifluoromethyl,
- (g) —$CO_2R^9$,
- (h) —$(CO)R^9$,
- (i) —$NR^{10}R^{11}$,
- (j) —$CONR^{10a}R^{11a}$,
- (k) oxo
- (l) —$SR^{12}$,
- (m) —$S(O)R^{12}$,
- (n) —$SO_2R^{12}$,
- (o) —$SO_2NR^{10a}R^{11a}$, and
- (p) —CN, (4) halo,
(5) oxo,
(6) hydroxy,
(7) —O—$C_{1-6}$alkyl, which is unsubstituted or substituted with 1-5 substituents where the substituents are each independently selected from:
- (a) halo,
- (b) hydroxy,
- (c) —$C_{3-6}$cycloalkyl,
- (d) phenyl,
- (e) —$CO_2R^9$, and
- (f) —$NR^{10}R^{11}$, (8) —CN,
(9) —$CO_2R^9$,
(10) —$NR^{10}R^{11}$,
(11) —$SR^{12}$,
(12) —$S(O)R^{12}$,
(13) —$SO_2R^{12}$,
(14) —$SO_2NR^{10a}R^{11a}$,
(15) —$CONR^{10a}R^{11a}$,
(16) —$OCO_2R^9$,
(17) —$(NR^{10a})CO_2R^9$,
(18) —$O(CO)NR^{10a}R^{11a}$,
(19) —$(NR^9)(CO)NR^{10a}R^{11a}$,
(20) —(CO)—$(CO)NR^{10a}R^{11a}$, and
(21) —(CO)—$(CO)OR^9$;

or where $R^{3a}$ and $R^{3b}$ and the carbon atom(s) to which they are attached join to form a ring selected from cyclobutyl, cyclopentyl, cyclohexyl, cyclopentenyl, cyclohexenyl, azetidinyl, pyrrolidinyl, piperidinyl, azepanyl, tetrahydrofuranyl, tetrahydropyranyl, furanyl, dihydrofuranyl, dihydropyranyl, thienyl, dihydrothienyl, tetrahydrothienyl, dihydrothiopyranyl, tetrahydrothiopyranyl, imidazolyl, imidazolinyl, and piperazinyl, which ring is unsubstituted or substituted with 1-5 substituents independently selected from:
- (a) —$C_{1-6}$alkyl, which is unsubstituted or substituted with 1-3 substituents independently selected from:
  - (i) halo,
  - (ii) hydroxy,
  - (iii) —O—$C_{1-6}$alkyl,
  - (iv) —$C_{3-6}$cycloalkyl,
  - (v) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl, which phenyl or heterocycle is unsubstituted or substituted with 1-5 substituents each independently selected from:
(I) —$C_{1-6}$alkyl,
(II) —O—$C_{1-6}$alkyl,
(III) halo,
(IV) hydroxy,
(V) trifluoromethyl, and
(VI) —$OCF_3$,
(vi) —$CO_2R^9$,
(vii) —$NR^{10}R^{11}$,
(viii) —$SO_2R^{12}$,
(ix) —$CONR^{10a}R^{11a}$, and
(x) —$(NR^{10a})CO_2R^9$,
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:
(i) —$C_{1-6}$alkyl, which is unsubstituted or substituted with 1-6 fluoro,
(ii) halo,
(iii) hydroxy,
(iv) —O—$C_{1-6}$alkyl, which is unsubstituted or substituted with 1-6 fluoro, and
(v) —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo;
$A^1$, $A^2$ and $A^3$ are each independently selected from:
(1) a bond,
(2) —$CR^{13}R^{14}$—, wherein $R^{13}$ and $R^{14}$ are each independently selected from:
(a) hydrogen,
(b) $C_{1-6}$ alkyl, which is unsubstituted or substituted with 1-5 substituents each independently selected from:
(i) —$C_{3-6}$cycloalkyl,
(ii) —O—$C_{1-6}$alkyl,
(iii) halo,
(iv) hydroxy, and
(v) phenyl,
(c) hydroxy, and
(d) halo,
(3) —$NR^{10}$—,
(4) —$CR^{13}R^{14}$—$NR^{10}$—,
(5) —$CR^{13}R^{14}$—$CH_2$—,
(6) —$CH_2$—$CR^{13}R^{14}$—,
(7) —O—$CR^{13}R^{14}$—,
(8) —$CR^{13}R^{14}$—O—,
(9) —C≡C—,
(10) —$C(R^{13})$=$C(R^{14})$—, and
(11) —C(=O)—,
or where one or two of $A^1$, $A^2$ and $A^3$ are optionally absent;
0-1 of $A^4$, $A^5$, $A^6$ and $A^7$ is selected from:
(1) —O—,
(2) —C(=O)—
(3) —$N(R^{15})$—, wherein $R^{15}$ is selected from:
(i) hydrogen,
(ii) $C_{1-6}$ alkyl, which is unsubstituted or substituted with 1-5 substituents where the substituents are each independently selected from:
(a) hydroxy,
(b) —O—$C_{1-6}$alkyl,
(c) halo,
(d) —$C_{3-6}$cycloalkyl,
(e) trifluoromethyl, and
(f) phenyl,
where the remainder of $A^4$, $A^5$, $A^6$ and $A^7$ are each independently selected from:
(1) a bond, and
(2) —$CR^{13}R^{14}$—,
where one or both of $A^4$ and $A^7$ are optionally absent;
$E^1$ and $E^5$ are each independently selected from:
(1) =$C(R^4)$—,
(2) —$CR^4R^5$—,
(3) —C(=O)—,
(4) —C(=S)—,
(5) =N—,
(6) =$N^+(O^-)$—,
(7) —$N(R^4)$—,
(8) —O—,
(9) —S—, and
(10) —$SO_2$—;
$E^3$ and $E^4$ are each independently selected from:
(1) a bond,
(2) =$C(R^4)$—,
(3) —$CR^4R^5$—,
(4) —C(=O)—,
(5) =N—,
(6) =$N^+(O^-)$—,
(7) —$N(R^4)$—, and
(8) —O—,
where one or both of $E^3$ and $E^4$ are optionally absent;
$E^2$ is selected from:

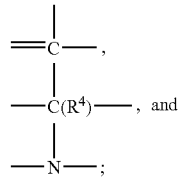

$G^1$ and $G^2$ are each independently selected from:
(1) =$C(R^4)$—,
(2) =N—, and
(3) =$N^+(O^-)$—;
$R^4$ and $R^5$ are each independently selected from:
(1) hydrogen;
(2) —$C_{1-4}$alkyl, which is unsubstituted or substituted with 1-5 substituents each independently selected from:
(a) halo,
(b) hydroxy, (c) —O—$C_{1-6}$alkyl,
(d) —$C_{3-6}$cycloalkyl,
(e) phenyl,
(f) —$CONR^{10a}R^{11a}$,
(g) —$CO_2R^9$, and
(h) —$NR^{10}R^{11}$,
(3) —$C_{3-6}$cycloalkyl,
(4) phenyl, which is unsubstituted or substituted with 1-3 substituents each independently selected from:
  (a) —$C_{1-4}$alkyl, which is unsubstituted or substituted with 1-3 fluoro,
  (b) halo,
  (c) hydroxy, and
  (d) —O—$C_{1-6}$alkyl, which is unsubstituted or substituted with 1-6 fluoro,
(5) halo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,
(13) —$OCO_2R^9$, and
(14) —$(NR^{10a})CO_2R^9$;

$R^6$ is selected from:
(1) hydrogen,
(2) —$C_{1-6}$alkyl or —$C_{3-6}$cycloalkyl which are unsubstituted or substituted with 1-7 substituents each independently selected from:
  (a) halo,
  (b) hydroxy,
  (c) —O—$C_{1-6}$alkyl,
  (d) —$C_{3-6}$cycloalkyl,
  (e) phenyl, which is unsubstituted or substituted with 1-5 substituents each independently selected from:
    (i) —$C_{1-6}$alkyl,
    (ii) —O—$C_{1-6}$alkyl,
    (iii) halo,
    (iv) hydroxy, and
    (v) trifluoromethyl,
  (f) —$CO_2R^9$,
  (g) —$NR^{10}R^{11}$,
  (h) —$CONR^{10}R^{11}$,
  (i) —$SO_2R^{12}$, and
  (j) trifluoromethyl
(3) phenyl or heterocycle, wherein heterocycle is selected from: pyridyl, pyrimidinyl, pyrazinyl, thienyl, and morpholinyl, which is unsubstituted or substituted with 1-5 substituents each independently selected from:
  (a) —$C_{1-6}$alkyl,
  (b) —O—$C_{1-6}$alkyl,
  (c) halo,
  (d) hydroxy, and
  (e) trifluoromethyl;

or a pharmaceutically acceptable salt thereof and individual enantiomers and diastereomers thereof.

2. The compound of claim 1 having the formula Ia:

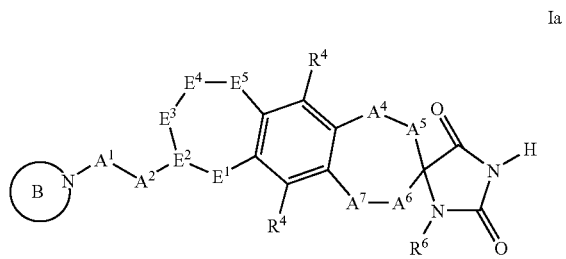

Ia or a pharmaceutically acceptable salt thereof and individual enantiomers and diastereomers thereof.

3. The compound of claim 1 having the formula Ib:

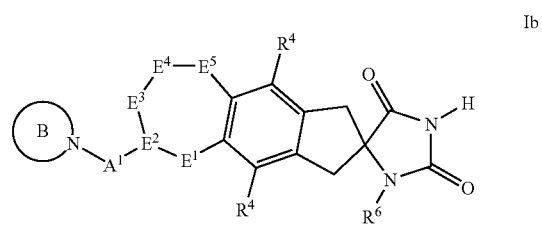

Ib or a pharmaceutically acceptable salt thereof and individual enantiomers and diastereomers thereof.

4. The compound of claim 1 having formula Ic:

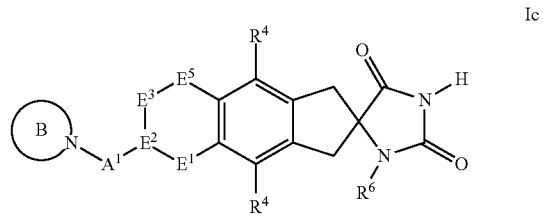

Ic or a pharmaceutically acceptable salt thereof and individual enantiomers and diastereomers thereof.

5. The compound of claim 1 having the formula Id:

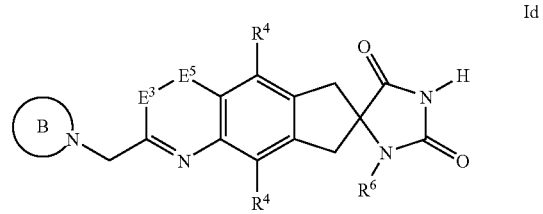

Id or a pharmaceutically acceptable salt thereof and individual enantiomers and diastereomers thereof.

6. The compound of claim 1 wherein B is selected from

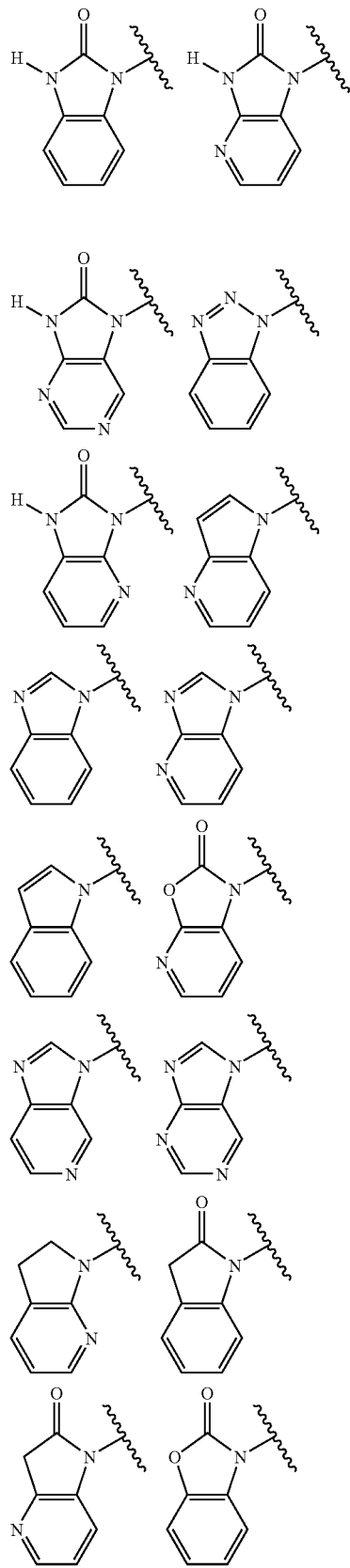

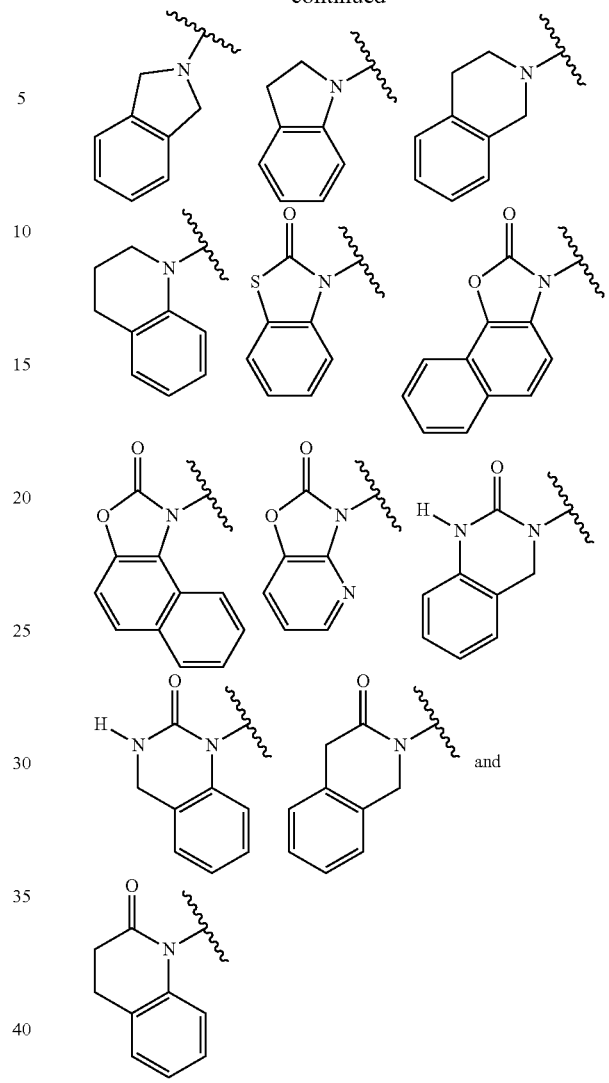

where B is unsubstituted or substituted with 1-5 substituents each independently selected from $R^1$, $R^2$, $R^{3a}$ and $R^{3b}$.

7. The compound of claim 1, wherein B is selected from 2-oxobenzimidazolinyl, indolyl, indolinyl, isoindolinyl, tetrahydroquinolinyl, tetrahydroisoquinolinyl, 2-oxoindolinyl, 2-oxobenzoxazolinyl, azaindolinyl, 2-oxoazabenzimidazolinyl, phthalimidyl, 2-oxotetrahydroquinolinyl, benzimidazolyl.

8. The compound of claim 1, wherein $R^1$, $R^2$, $R^{3a}$ and $R^{3b}$ are each independently selected from:
(1) —$C_{1-6}$alkyl, which is unsubstituted or substituted with 1-5 substituents each independently selected from:
 (a) fluoro,
 (b) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl,
 (c) —$CO_2R^9$,
 (d) —$CONR^{10a}R^{11a}$,
 (e) —O—$C_{1-6}$alkyl,
 (f) —O—$C_{3-6}$cycloalkyl, and
 (g) hydroxy, (2) phenyl or heterocycle, wherein heterocycle is selected from: pyridinyl, pyrimidinyl, pyrazinyl, thienyl, pyridazinyl, pyrrolidinyl, thiazolyl, isothiazolyl, 2-oxopyrrolidinyl, tetrahydrofuryl, piperidinyl, tetrahydrothienyl, and tetrahydrothiopyranyl, which phenyl or heterocycle is unsubstituted or substituted with 1-5 substituents each independently selected from:
- (a) —$C_{1-6}$alkyl, which is unsubstituted or substituted with 1-3 fluoro
- (b) halo,
- (c) —$CO_2R^9$,
- (d) —$(CO)R^9$,
- (e) —$CONR^{10a}R^{11a}$,
- (f) —O—$C_{1-6}$alkyl, which is unsubstituted or substituted with 1-3 fluoro,
- (g) hydroxy,
- (h) oxo,
- (i) —S—$C_{1-4}$alkyl,
- (j) —S(O)—$C_{1-4}$alkyl, and
- (k) —$SO_2$—$C_{1-4}$alkyl, (3) halo,
(4) hydroxy,
(5) —O—$C_{1-6}$alkyl, which is unsubstituted or substituted with 1-3 fluoro,
(6) —$NH_2$,
(7) —$C_{3-6}$cycloalkyl,
(8) —(CO)—(CO)$NR^{10a}R^{11a}$,
(9) —CN, and
(10) —$SO_2NR^{10a}R^{11a}$.

9. The compound of claim 1, wherein $R^1$ and $R^2$ are each independently selected from:
(1) —$C_{1-4}$alkyl, which is unsubstituted or substituted with 1-5 substituents each independently selected from:
- (a) fluoro,
- (b) phenyl,
- (c) —$CO_2R^9$,
- (d) —$CONR^{10a}R^{11a}$,
- (e) —O—$C_{3-6}$cycloalkyl, (2) phenyl or heterocycle, wherein heterocycle is selected from: pyridinyl, pyrimidinyl, pyrazinyl, pyridazinyl, pyrrolidinyl, thiazolyl, tetrahydrofuryl, piperidinyl, and tetrahydrothiopyranyl, which phenyl or heterocycle is unsubstituted or substituted with 1-5 substituents each independently selected from:
- (a) —$C_{1-4}$alkyl, which is unsubstituted or substituted with 1-3 fluoro
- (b) halo,
- (c) —$CO_2R^9$,
- (d) —$(CO)R^9$,
- (e) —$CONR^{10a}R^{11a}$,
- (f) —O—$C_{1-4}$alkyl, which is unsubstituted or substituted with 1-3 fluoro,
- (g) hydroxy,
- (h) oxo
- (i) —S—$C_{1-4}$alkyl,
- (j) —S(O)—$C_{1-4}$alkyl, and
- (k) —$SO_2$—$C_{1-4}$alkyl, (3) halo,
(4) hydroxy,
(5) —O—$C_{1-4}$alkyl, which is unsubstituted or substituted with 1-3 fluoro,
(6) —CN,
(7) —$C_{3-6}$cycloalkyl,
(8) —(CO)—(CO)$NR^{10a}R^{11a}$, and
(9) —$SO_2NR^{10a}R^{11a}$.

10. The compound of claim 1, wherein $R^{3a}$ and $R^{3b}$ and the carbon atom(s) to which they are attached join to form a ring selected from piperidinyl, cyclohexyl, cyclopentyl, pyrrolidinyl, tetrahydrofuranyl, tetrahydropyranyl, tetrahydrothienyl, and tetrahydrothiopyranyl, which ring is unsubstituted or substituted with 1-3 substituents independently selected from:
- (a) —$C_{1-6}$alkyl, which is unsubstituted or substituted with 1-3 substituents each independently selected from:
  - (i) halo, and
  - (ii) phenyl,
- (b) phenyl or heterocycle, wherein heterocycle is selected from: pyridinyl, pyrimidinyl and pyrazinyl,
- (c) —$CO_2R^9$, hydroxy, and
- (d) oxo.

11. The compound of claim 1, wherein $A^1$ is $CH_2$, a bond or —C(=O)—; $A^2$ is $CH_2$ or a bond; $A^3$ is a bond; $A^4$ is $CH_2$ or a bond; $A^5$ is $CH_2$; $A^6$ is $CH_2$; and $A^7$ is $CH_2$ or a bond.

12. The compound of claim 1, wherein $G^1$ is =C($R^4$)— and $G^2$ is =C($R^4$)—.

13. The compound of claim 1, wherein $R^4$ and $R^5$ are independently selected from:
(1) hydrogen;
(2) —$C_{1-4}$alkyl, which is unsubstituted or substituted with 1-3 substituents each independently selected from:
- (a) halo,
- (b) hydroxy,
- (c) —O—$C_{1-6}$alkyl,
- (d) —$C_{3-6}$cycloalkyl, and
- (e) phenyl, (3) —$C_{3-6}$cycloalkyl,
(4) phenyl, which is unsubstituted or substituted with 1-3 substituents each independently selected from:
- (a) —$C_{1-4}$alkyl, which is unsubstituted or substituted with 1-3 fluoro, and
- (b) halo, (5) halo,
(6) hydroxy,
(7) —O—$C_{1-6}$alkyl, which is unsubstituted or substituted with 1-3 fluoro,
(8) —CN, and
(9) —$NR^{10}R^{11}$.

14. The compound of claim 1, wherein $R^6$ is selected from:
(1) hydrogen,
(2) —$C_{1-4}$alkyl which is unsubstituted or substituted with 1-5 substituents each independently selected from:
- (a) halo,
- (b) hydroxy,
- (c) —$C_{3-6}$cycloalkyl, and
- (d) phenyl, (3) phenyl or heterocycle, wherein heterocycle is selected from: pyridyl, pyrimidinyl, and pyrazinyl.

15. The compound of claim 1, wherein $R^9$ is independently selected from:
(i) hydrogen,
(ii) —$C_{1-5}$alkyl, which is unsubstituted or substituted with 1-5 substituents, substituents each independently selected from:
- (I) halo,
- (II) hydroxy,
- (III) —O—$C_{1-6}$alkyl,
- (IV) —$C_{3-6}$cycloalkyl,
- (V) phenyl, which is unsubstituted or substituted with 1-4 substituents each independently selected from:
  - (1) —$C_{1-4}$alkyl,
  - (2) —O—$C_{1-4}$alkyl, and
  - (3) halo, (iii) —C$_{3-6}$cycloalkyl, and
(iv) phenyl or heterocycle, wherein heterocycle is selected from: pyridinyl, pyrimidinyl, pyrazinyl, thienyl, pyrrolidinyl, thiazolyl, oxazolyl, imidazolyl, triazolyl, tetrazolyl, indolinyl, indolyl, quinolinyl, isoquinolinyl, tetrahydroquinolinyl, isoindolinyl, tetrahydroisoquinolinyl, tetrahydrofuryl, piperidinyl, piperazinyl, and morpholinyl, which phenyl or heterocycle is unsubstituted or substituted with 1-5 substituents each independently selected from:
(I) halo,
(II) —C$_{1-4}$alkyl, which is unsubstituted or substituted with 1-3 halo,
(III) —O—C$_{1-4}$alkyl, which is unsubstituted or substituted with 1-3 halo,
(IV) —C$_{3-6}$cycloalkyl,
(V) oxo,
(VI) —CN, and
(VII) hydroxy.

16. The compound of claim 1, wherein R$^{10}$ and R$^{11}$ are each independently selected from:
(i) hydrogen,
(ii) —C$_{1-5}$alkyl, which is unsubstituted or substituted with 1-5 substituents each independently selected from:
(I) —O—C$_{1-4}$alkyl,
(II) halo,
(III) hydroxy, and
(IV) —OCF$_3$,
(iii) —C$_{4-6}$cycloalkyl,
(iv) phenyl, which is unsubstituted or substituted with 1-4 substituents each independently selected from:
(I) —C$_{1-4}$alkyl,
(II) —O—C$_{1-4}$alkyl,
(III) halo,
(IV) trifluoromethyl, and
(V) —OCF$_3$, and
(v) benzyl, which is unsubstituted or substituted with 1-4 substituents each independently selected from:
(I) —C$_{1-4}$alkyl,
(II) —O—C$_{1-4}$alkyl,
(III) halo, and
(IV) trifluoromethyl,
(vi) —COR$^9$, and
(vii) —SO$_2$R$^{12}$.

17. The compound of claim 1, wherein R$^{10a}$ and R$^{11a}$ are each independently selected from:
(i) hydrogen,
(ii) —C$_{1-4}$alkyl, which is unsubstituted or substituted with 1-4 substituents each independently selected from:
(I) halo, and
(II) hydroxy,
(iii) —C$_{5-6}$cycloalkyl,
(iv) phenyl, which is unsubstituted or substituted with 1-4 substituents each independently selected from:
(I) —C$_{1-4}$alkyl,
(II) —O—C$_{1-4}$alkyl,
(III) halo, and
(V) trifluoromethyl,
(v) benzyl, which is unsubstituted or substituted with 1-4 substituents each independently selected from:
(I) —C$_{1-4}$alkyl,
(II) —O—C$_{1-4}$alkyl,
(III) halo, and
(IV) trifluoromethyl,
or where R$^{10a}$ and R$^{11a}$ join to form a ring selected from azetidinyl, pyrrolidinyl, piperidinyl, piperazinyl, and morpholinyl, which ring is unsubstituted or substituted with 1-3 substituents each independently selected from:
(I) —C$_{1-4}$alkyl
(II) —O—C$_{1-4}$alkyl
(III) halo
(IV) hydroxy,
(V) phenyl,
(VI) benzyl, and
(VII) —COR$^9$.

18. The compound of claim 1, wherein R$^{12}$ is selected from:
(i) —C$_{1-4}$alkyl, which is unsubstituted or substituted with 1-3 fluoro,
(ii) —C$_{3-6}$cycloalkyl,
(iii) phenyl which is unsubstituted or substituted with 1-3 substituents each independently selected from:
(I) —C$_{1-4}$alkyl,
(II) —O—C$_{1-4}$alkyl,
(III) halo, and
(IV) trifluoromethyl,
(iv) benzyl, which is unsubstituted or substituted with 1-3 substituents each independently selected from:
(I) —C$_{1-4}$alkyl,
(II) —O—C$_{1-4}$alkyl,
(III) halo, and
(IV) trifluoromethyl.

19. A compound selected from:

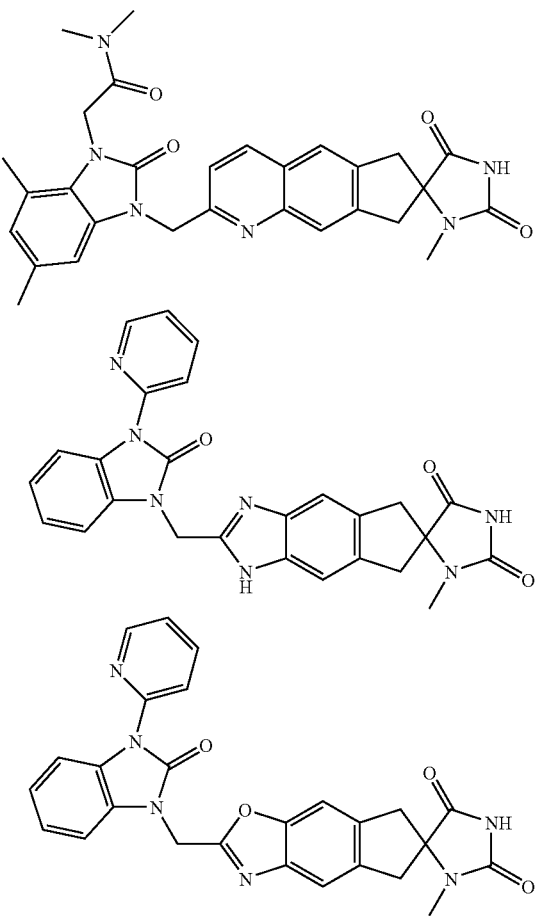

109
-continued
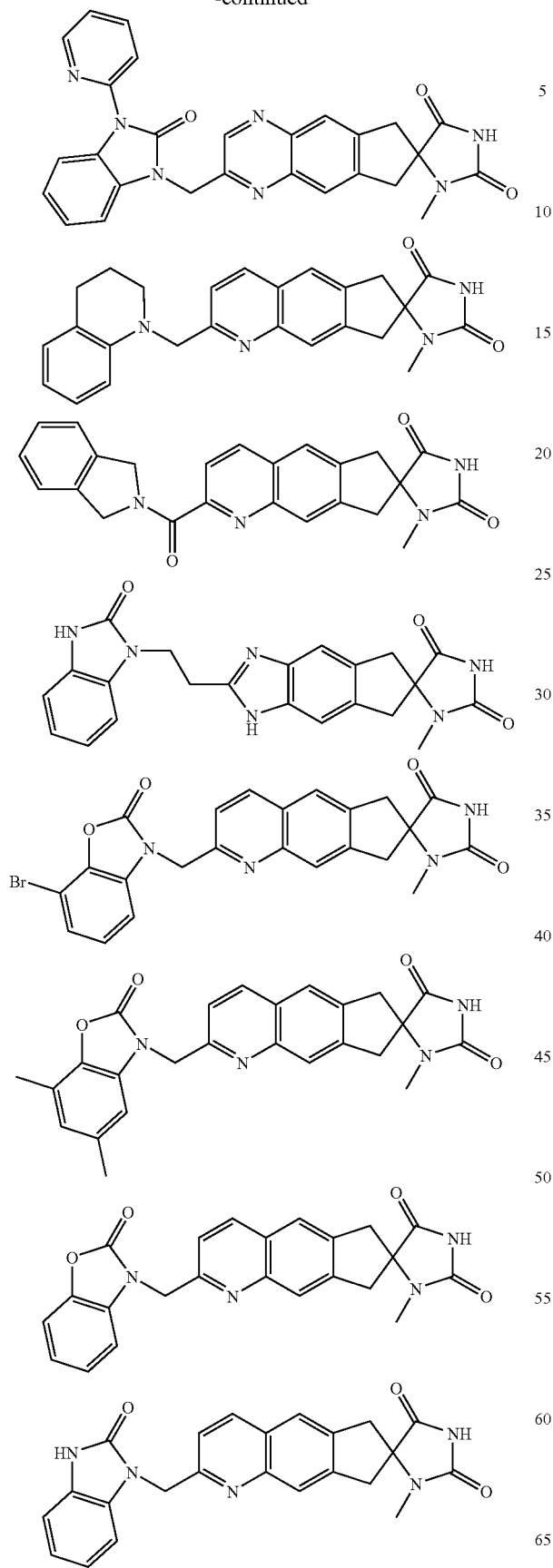
110
-continued
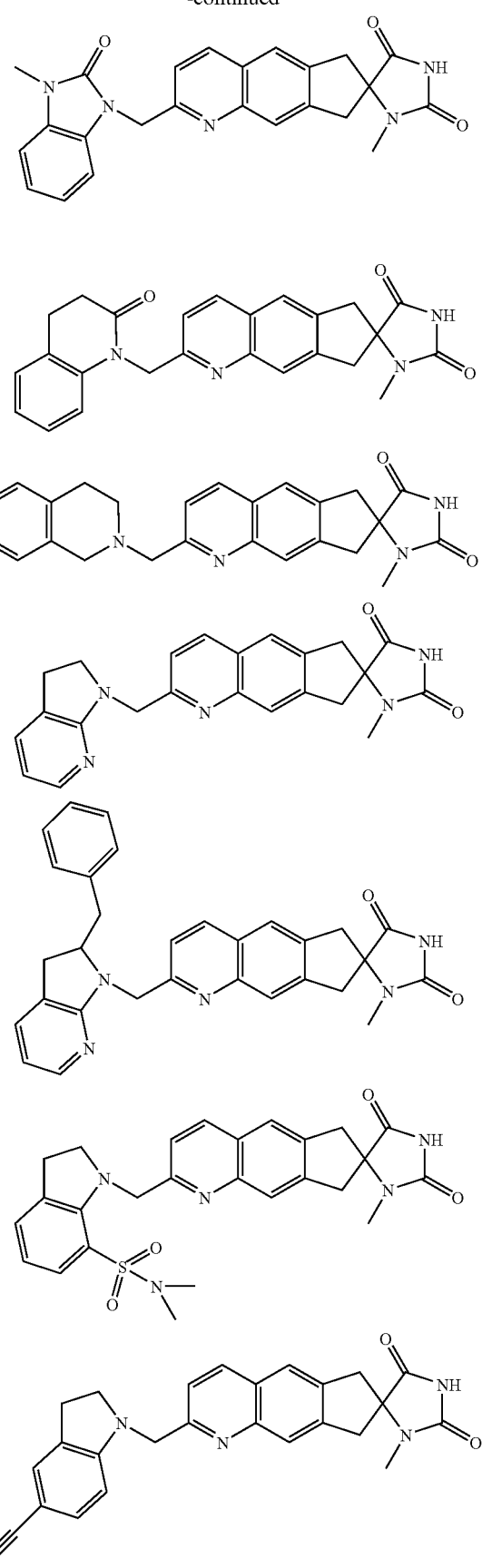

111
-continued
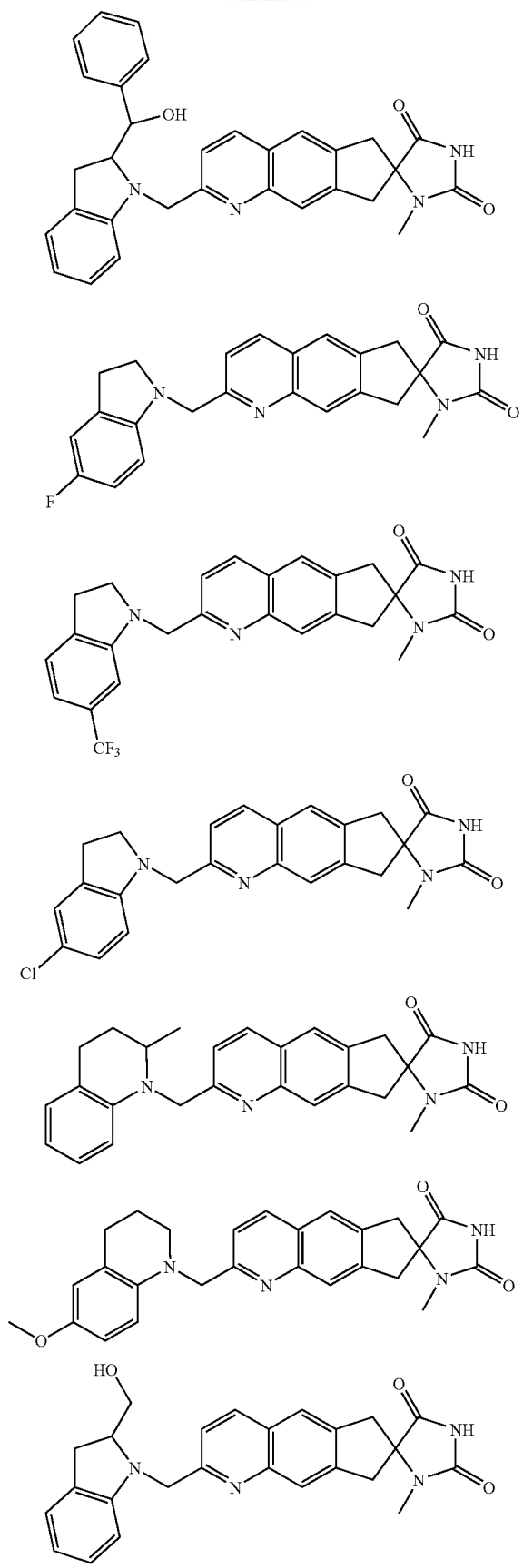
112
-continued
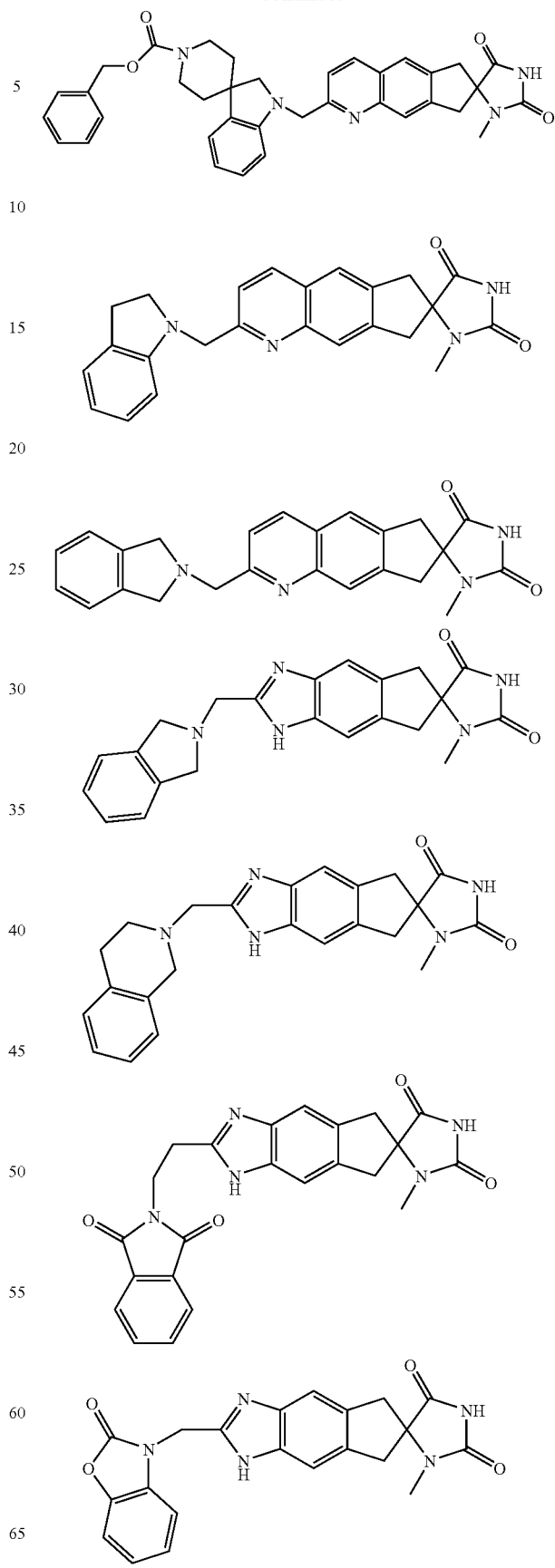

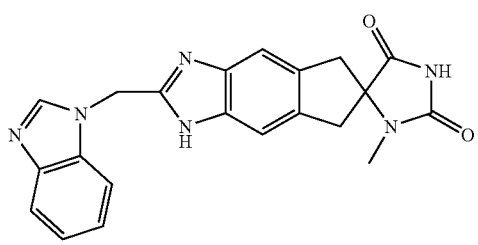
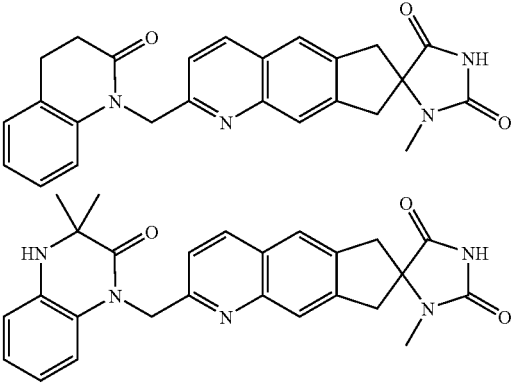
or a pharmaceutically acceptable salt and individual stereoisomers thereof.
20. A pharmaceutical composition which comprises an inert carrier and the compound of claim 1, or a pharmaceutically acceptable salt thereof and individual enantiomers and diastereomers thereof.
* * * * *

UNITED STATES PATENT AND TRADEMARK OFFICE
CERTIFICATE OF CORRECTION

| | | |
|---|---|---|
| PATENT NO. | : 8,071,771 B2 | Page 1 of 1 |
| APPLICATION NO. | : 12/085005 | |
| DATED | : December 6, 2011 | |
| INVENTOR(S) | : Bell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 702 days.

Signed and Sealed this

Seventh Day of February, 2012

David J. Kappos
*Director of the United States Patent and Trademark Office*